(12) United States Patent
Dominique et al.

(10) Patent No.: US 7,625,895 B2
(45) Date of Patent: Dec. 1, 2009

(54) DIPHENYL-DIHYDRO-IMIDAZOPYRIDINONES

(75) Inventors: Romyr Dominique, Wayne, NJ (US); Robert Alan Goodnow, Jr., Gillette, NJ (US); Qi Qiao, Bloomfield, NJ (US); Binh Thanh Vu, North Caldwell, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 60 days.

(21) Appl. No.: 12/050,235

(22) Filed: Mar. 18, 2008

(65) Prior Publication Data
US 2008/0255119 A1 Oct. 16, 2008

Related U.S. Application Data

(60) Provisional application No. 60/923,110, filed on Apr. 12, 2007.

(51) Int. Cl.
*A61K 31/437* (2006.01)
*C07D 471/04* (2006.01)
*A61K 31/5377* (2006.01)
*A61P 35/00* (2006.01)
*C07D 413/14* (2006.01)

(52) U.S. Cl. .................. 514/235.8; 514/300; 546/121; 544/121

(58) Field of Classification Search .................. 546/121; 544/121; 514/235.8, 300
See application file for complete search history.

(56) References Cited

U.S. PATENT DOCUMENTS

| 4,284,778 | A | * | 8/1981 | Kubo et al. ................. 546/115 |
| 6,531,605 | B1 | | 3/2003 | Hogan |
| 6,617,346 | B1 | | 9/2003 | Kong et al. |
| 6,734,302 | B2 | | 5/2004 | Kong et al. |

FOREIGN PATENT DOCUMENTS

| EP | 363 061 | 11/1990 |
| WO | WO 0078725 | 12/2000 |
| WO | WO 03/051359 | 6/2003 |
| WO | WO 2005/110996 | 11/2005 |
| WO | WO 2005/123691 | 12/2005 |
| WO | WO 2007/082805 | 7/2007 |
| WO | WO 2007/107543 | 9/2007 |

OTHER PUBLICATIONS

Wells et al, *J. Org. Chem.* (1972) 37, 2158-2161.
Hunter et al, *Can. J. Chem.* (1972) 50, 669-677.
McCapra et al, *Protochem and Photobiol.*, (1965) 4, 1111-1121.
Zupanc et al, *Bull. Soc. Chem. & Tech.* (1980-81) 27/28, 71-80.
H. Ansel et al, *Pharm. Dosage Forms and Drug Delivery Systems* (6th Ed) (1995) 108-109.
H. Ansel et al, *Pharm. Dosage Forms and Drug Delivery Systems* (6th Ed) (1995) pp. 196, 1456-1457.
Krogsgaard-Larsen et al, *Textbook of Drug Design and Development* (2d Ed. 1996) 152-191.
V. Percec et al, *J. Org. Chem.* (2001) 66, p. 2104.
*Modern Arne Chemistry*, (2002) 53-106.

* cited by examiner

*Primary Examiner*—D. Margaret Seaman
*Assistant Examiner*—Niloofar Rahmani
(74) *Attorney, Agent, or Firm*—George W. Johnston; Patricia S. Rocha-Tramaloni

(57) ABSTRACT

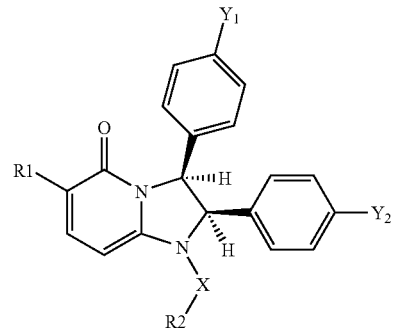

and the pharmaceutically acceptable salts and esters thereof, X, $R_1$, $R_2$, $Y_1$ and $Y_2$ are described herein inhibit the interaction of MDM2 protein with a p53-like peptide and hence have anti proliferative activity.

17 Claims, No Drawings

DIPHENYL-DIHYDRO-IMIDAZOPYRIDINONES

PRIORITY OF RELATED APPLICATION(S)

This application claims the benefit of U.S. Provisional Application No. 60/923,110, filed Apr. 12, 2007. The entire contents of the above-identified application is hereby incorporated by reference.

FIELD OF THE INVENTION

This invention is related to a compound of formula 1

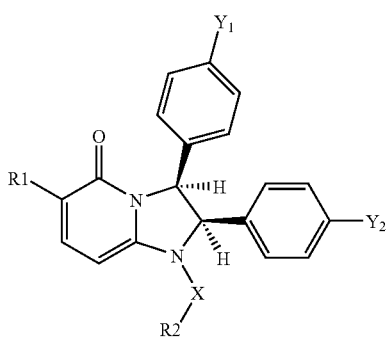

and the pharmaceutically acceptable salts thereof wherein X, $R_1$, $R_2$, $Y_1$ and $Y_2$ are as described herein.

These compounds inhibit the interaction of MDM2 protein with a p-53-like peptide and therefore exhibit antiproliferative activity.

BACKGROUND OF THE INVENTION p53 is a tumor suppressor protein that plays a central role in protection against development of cancer. It guards cellular integrity and prevents the propagation of permanently damaged clones of cells by the induction of growth arrest or apoptosis. At the molecular level, p53 is a transcription factor that can activate a panel of genes implicated in the regulation of cell cycle and apoptosis. p53 is a potent cell cycle inhibitor which is tightly regulated by MDM2 at the cellular level. MDM2 and p53 form a feedback control loop. MDM2 can bind p53 and inhibit its ability to transactivate p53-regulated genes. In addition, MDM2 mediates the ubiquitin-dependent degradation of p53. p53 can activate the expression of the MDM2 gene, thus raising the cellular level of MDM2 protein. This feedback control loop insures that both MDM2 and p53 are kept at a low level in normal proliferating cells. MDM2 is also a cofactor for E2F, which plays a central role in cell cycle regulation.

The ratio of MDM2 to p53 (E2F) is dysregulated in many cancers. Frequently occurring molecular defects in the p16INK4/p19ARF locus, for instance, have been shown to affect MDM2 protein degradation. Inhibition of MDM2-p53 interaction in tumor cells with wild-type p53 should lead to accumulation of p53, cell cycle arrest and/or apoptosis. MDM2 antagonists, therefore, can offer a novel approach to cancer therapy as single agents or in combination with a broad spectrum of other antitumor therapies. The feasibility of this strategy has been shown by the use of different macromolecular tools for inhibition of MDM2-p53 interaction (e.g. antibodies, antisense oligonucleotides, peptides). MDM2 also binds E2F through a conserved binding region as p53 and activates E2F-dependent transcription of cyclin A, suggesting that MDM2 antagonists might have effects in p53 mutant cells.

Wells et al. *J. Org. Chem.*, 1972, 37, 2158-2161, report synthesis of imidazolines. Hunter et al., *Can. J. Chem.*, 1972, Vol. 50, pgs. 669-77, report the preparation of a marine and isoamarine compounds which had previously been studied for chemiluminescence (McCapra et al. *Photochem. and Photobiol.* 1965, 4, 1111-1121). Zupanc et al. *Bull. Soc. Chem. & Tech.* (Yugoslavia) 1980-81, 27/28, 71-80, report the use of triaryl imidazolines as starting materials in the preparation of EDTA derivatives.

EP 363 061 to Matsumoto reports imidazoline derivatives useful as immunomodulators. The compounds were indicated to have low toxicity. Treatment and/or prevention of rheumatoid arthritis, multiple sclerosis, systemic lupus, erythemathodes, and rheumatic fever were implicated. WO 00/78725 to Choueiry et al. report a method for making substituted amidine compounds, and indicate that imidazoline-type compounds may be useful in the treatment of diabetes or related diseases involving impaired glucose disposal.

U.S. Pat. No. 6,617,346 B1 issued Sep. 9, 2003 and U.S. Pat. No. 6,734,302 B2 issued May 11, 2004 disclose related racemic cis-imidazolines.

SUMMARY OF THE INVENTION

The present invention provides a compound of formula 1

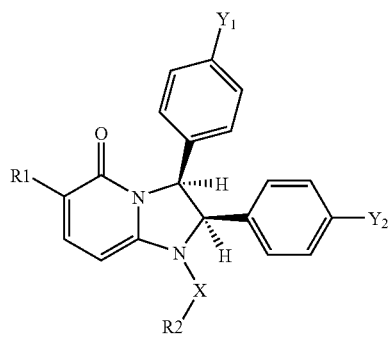

and the pharmaceutically acceptable salts and esters thereof wherein X, $R_1$, $R_2$, $Y_1$ and $Y_2$ are as herein described.

DETAILED DESCRIPTION OF THE INVENTION

The present invention provides chiral cis-imidazolines which are small molecule inhibitors of the MDM2-p53 interaction. In cell-free and cell-based assays, compounds of the present invention are shown to inhibit the interaction of MDM2 protein with a p53-like peptide with a potency that is approximately 100 fold greater than a p53-derived peptide. In cell-based assays, these compounds demonstrate mechanistic activity. Incubation of cancer cells with wild-type p53 leads to accumulation of p53 protein induction of p53-regulated p21 gene, and cell cycle arrest in G1 and G2 phase, resulting in potent antiproliferative activity against wild-type p53 cells in vitro. In contrast, these activities were not observed in cancer cells with mutant p53 at comparable compound concentrations. Therefore, the activity of MDM2 antagonists is likely linked to its mechanism of action. These compounds can be potent and selective anticancer agents.

The present invention provides at least one compound of formula 1

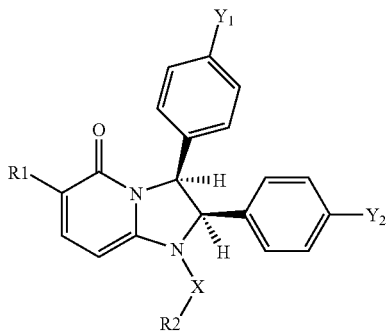

wherein
Y₁ and Y₂ are independently selected from the group consisting of halogen, trifluoromethyl, —NO₂, —C≡N, and —C≡CH;
X is selected from the group consisting of —SO₂, —C═O and —C═OCH₂;
R1 is selected from the group consisting of hydrogen, halogen, aryl, substituted aryl, heterocycle, substituted heterocycle, alkenyl and C═OR3 wherein R3 is alkoxy, amino, cycloamino, heterocycle or substituted heterocycle;
R2 is selected from the group consisting of substituted or unsubstituted cycloalkyl, aryl, heteroaryl and heterocycle; and the pharmaceutically acceptable salts and esters thereof.
Preferred compounds are compounds of formula I wherein Y₁ and Y₂ are each independently selected from —Cl and —Br and X is SO₂.
Further preferred are compounds wherein Y₁ and Y₂ are each independently selected from —Cl and —Br, X is SO₂ and R₂ is aryl which is disubstituted by halogen and CN.
Further preferred are compounds wherein Y₁ and Y₂ are each independently selected from —Cl and —Br, X is SO₂ and R₂ is aryl which is monosubstituted by carboxy alkoxy.
Further preferred are compounds wherein Y₁ and Y₂ are each independently selected from —Cl and —Br, X is SO₂, R₂ is aryl which is disubstituted by halogen and CN or monosubstituted by carboxy alkoxy and R₁ is hydrogen or —COR₃ where R₃ is a substituted or unsubstituted heterocycle.
Also preferred compounds are compounds in which the two hydrogen atoms of the imidazoline ring are in a cis configuration to each other. The compounds may be in a racemic form and may be optically active.
Especially preferred compounds are for example:
rac-5-[cis-2,3-Bis-(4-chloro-phenyl)-5-oxo-2,3-dihydro-5H-imidazo[1,2-a]pyridine-1-sulfonyl]-2-fluoro-benzonitrile;
3-[2R*,3S*-Bis-(4-chloro-phenyl)-5-oxo-2,3-dihydro-5H-imidazo[1,2-a]pyridine-1-sulfonyl]-benzonitrile-5-[2R*, 3S*-Bis-(4-chloro-phenyl)-5-oxo-2,3-dihydro-5H-imidazo[1,2-a]pyridine-1-sulfonyl]-2-fluoro-benzonitrile;
2R*,3S*-Bis-(4-chloro-phenyl)-1-(2-fluoro-benzenesulfonyl)-2,3-dihydro-1H-imidazo[1,2-a]pyridin-5-one;
rac-3-[cis-2,3-Bis-(4-chloro-phenyl)-5-oxo-2,3-dihydro-5H-imidazo[1,2-a]pyridine-1-sulfonyl]-benzonitrile;
rac-4-[-cis-2,3-Bis-(4-chloro-phenyl)-5-oxo-2,3-dihydro-5H-imidazo[1,2-a]pyridine-1-sulfonyl]-benzonitrile;
rac-cis-2,3-Bis-(4-chloro-phenyl)-1-(2-fluoro-benzenesulfonyl)-2,3-dihydro-1H-imidazo[1,2-a]pyridin-5-one;
rac-cis-2,3-Bis-(4-chloro-phenyl)-1-(2,4-difluoro-benzenesulfonyl)-2,3-dihydro-1H-imidazo[1,2-a]pyridin-5-one;
rac-cis-2,3-Bis-(4-chloro-phenyl)-1-(2,5-dimethoxy-benzenesulfonyl)-2,3-dihydro-1H-imidazo[1,2-a]pyridin-5-one;
rac-cis-1-(2-Chloro-benzoyl)-2,3-bis-(4-chloro-phenyl)-2, 3-dihydro-1H-imidazo[1,2-a]pyridin-5-one;
rac-cis-1-(2-Chloro-benzenesulfonyl)-2,3-bis-(4-chlorophenyl)-2,3-dihydro-1H-imidazo[1,2-a]pyridin-5-one;
rac-cis-2 3-Bis-(4-chloro-phenyl)-1-(thiophene-3-sulfonyl)-2,3-dihydro-1H-imidazo[1,2-a]pyridin-5-one;
rac-cis-2,3-Bis-(4-chloro-phenyl)-1-(1-methyl-1H-imidazole-4-sulfonyl)-2,3-dihydro-1H-imidazo[1,2-a]pyridin-5-one;
rac-cis-2,3-Bis-(4-chloro-phenyl)-1-(4-fluoro-benzenesulfonyl)-2,3-dihydro-1H-imidazo[1,2-a]pyridin-5-one;
rac-cis-1-Benzenesulfonyl-rac-cis-bis-(4-chloro-phenyl)-2, 3-dihydro-1H-imidazo[1,2-a]pyridin-5-one;
rac-cis-2,3-Bis-(4-chloro-phenyl)-1-(2,6-difluoro-benzenesulfonyl)-2,3-dihydro-1H-imidazo[1,2-a]pyridin-5-one;
rac-cis-2,3-Bis-(4-chloro-phenyl)-1-(thiophene-2-sulfonyl)-2,3-dihydro-1H-imidazo[1,2-a]pyridin-5-one;
rac-cis-1-(3-Chloro-2-fluoro-benzenesulfonyl)-2,3-bis-(4-chloro-phenyl)-2,3-dihydro-1H-imidazo[1,2-a]pyridin-5-one;
rac-cis-2,3-Bis-(4-chloro-phenyl)-1-(2-fluoro-5-methyl-benzenesulfonyl)-2,3-dihydro-1H-imidazo[1,2-a]pyridin-5-one;
rac-1-(2-Chloro-4-fluoro-benzenesulfonyl)-cis-2, 3-bis-(4-chloro-phenyl)-2,3-dihydro-1H-imidazo[1,2-a]pyridin-5-one;
rac-cis-2,3-Bis-(4-chloro-phenyl)-1-(4-methoxy-benzenesulfonyl)-2,3-dihydro-1H-imidazo[1,2-a]pyridin-5-one;
rac-cis-2,3-Bis-(4-chloro-phenyl)-1-(toluene-3-sulfonyl)-2, 3-dihydro-1H-imidazo[1,2-a]pyridin-5-one;
rac-cis-2,3-Bis-(4-chloro-phenyl)-1-(3-methoxy-benzenesulfonyl)-2,3-dihydro-1H-imidazo[1,2-a]pyridin-5-one;
rac-cis-1-(5-Chloro-2-fluoro-benzenesulfonyl)-2,3-bis-(4-chloro-phenyl)-2,3-dihydro-1H-imidazo[1,2-a]pyridin-5-one;
rac-cis-1-(4-Chloro-2-fluoro-benzenesulfonyl)-2,3-bis-(4-chloro-phenyl)-2,3-dihydro-1H-imidazo1,2-a]pyridin-5-one;
rac-cis-2,3-Bis-(4-chloro-phenyl)-1-(3,4-difluoro-benzenesulfonyl)-2,3-dihydro-1H-imidazo[1,2-a]pyridin-5-one;
rac-3-[cis-2,3-Bis-(4-chloro-phenyl)-5-oxo-2,3-dihydro-5H-imidazo[1 2-a]pyridine-1-sulfonyl]-benzoic acid methyl ester;
rac-cis-1-(5-Chloro-2-methoxy-benzenesulfonyl)-2,3-bis-(4-chloro-phenyl)-2,3-dihydro-1H-imidazo[1,2-a]pyridin-5-one;
rac-cis-1-(3-Chloro-benzenesulfonyl)-2,3-bis-(4-chlorophenyl)-2,3-dihydro-1H-imidazo[1,2-a]pyridin-5-one;
rac-cis-2,3-Bis-(4-chloro-phenyl)-1-(3-fluoro-benzenesulfonyl)-2,3-dihydro-1H-imidazo[1,2-a]pyridin-5-one;
rac-cis-2 3-Bis-(4-chloro-phenyl)-1-(toluene-2-sulfonyl)-2 3-dihydro-1H-imidazo[1,2-a]pyridin-5-one;
rac-cis-1-(4-Chloro-benzenesulfonyl)-2,3-bis-(4-chlorophenyl)-2,3-dihydro-1H-imidazo[1,2-a]pyridin-5-one;
rac-cis-2,3-Bis-(4-chloro-phenyl)-1-(2-fluoro-benzoyl)-2,3-dihydro-1H-imidazo[1,2-a]pyridin-5-one;
rac-cis-1-(3-Chloro-4-fluoro-benzenesulfonyl)-2,3-bis-(4-chloro-phenyl)-2,3-dihydro-1H-imidazo[1,2-a]pyridin-5-one;
rac-cis-2,3-Bis-(4-chloro-phenyl)-1-(4-fluoro-2-methyl-benzenesulfonyl)-2,3-dihydro-1H-imidazo[1,2-a]pyridin-5-one;

rac-cis-2,3-Bis-(4-chloro-phenyl)-1-(5-fluoro-2-methyl-benzenesulfonyl)-2,3-dihydro-1H-imidazo[1,2-a]pyridin-5-one;

rac-cis-2,3-Bis-(4-chloro-phenyl)-1-(3-methoxy-benzoyl)-2,3-dihydro-1H-imidazo[1,2-a]pyridin-5-one;

rac-cis-2,3-Bis-(4-chloro-phenyl)-1-(2-trifluoromethoxy-benzenesulfonyl)-2,3-dihydro-1H-imidazo[1,2-a]pyridin-5-one;

rac-cis-2,3-Bis-(4-chloro-phenyl)-1-isobutyryl-2,3-dihydro-1H-imidazo[1,2-a]pyridin-5-one;

2R*,3S*-Bis-(4-chloro-phenyl)-1-(2-fluoro-benzenesulfonyl)-2,3-dihydro-1H-imidazo[1,2-a]pyridin-5-one;

rac-cis-2,3-Bis-(4-chloro-phenyl)-1-cyclopropanesulfonyl-2,3-dihydro-1H-imidazo[1,2-a]pyridin-5-one;

rac-cis-1-(3-Chloro-benzoyl)-2,3-bis-(4-chloro-phenyl)-2,3-dihydro-1H-imidazo[1,2-a]pyridin-5-one;

rac-cis-2,3-Bis-(4-chloro-phenyl)-1-(3-trifluoromethoxy-benzenesulfonyl)-2,3-dihydro-1H-imidazo[1,2-a]pyridin-5-one;

rac-cis-2,3-Bis-(4-chloro-phenyl)-1-(3-fluoro-benzoyl)2 3-dihydro-1H-imidazo[1,2-a]pyridin-5-one;

rac-cis-2,3-Bis-(4-chloro-phenyl)-1-[2-(2,5-dimethoxy-phenyl)-acetyl]-2,3-dihydro-1H-imidazo[1,2-a]pyridin-5-one;

rac-cis-2,3-Bis-(4-chloro-phenyl)-1-(furan-2-carbonyl)-2,3-dihydro-1H-imidazo[1,2-a]pyridin-5-one;

rac-cis-2,3-Bis-(4-chloro-phenyl)-1-(2-methoxy-benzoyl)-2,3-dihydro-1H-imidazo[1,2-a]pyridin-5-one;

1-(2-Chloro-benzoyl)-2R*,3S*-bis-(4-chloro-phenyl)-2,3-dihydro-1H-imidazo[1,2-a]pyridin-5-one.

rac-cis-2,3-Bis-(4-chloro-phenyl)-1-cyclopentanecarbonyl-2,3-dihydro-1H-imidazo[1,2-a]pyridin-5-one;

rac-cis-1-(3-Chloro-2-methyl-benzenesulfonyl)-2,3-bis-(4-chloro-phenyl)-2,3-dihydro-1H-imidazo[1,2-a]pyridin-5-one;

rac-cis-2,3-Bis-(4-chloro-phenyl)-1-(2-fluoro-benzene-sulfonyl)-2,3-dihydro-6-iodo-1H-imidazo[1,2-a]pyridin-5-one;6-(4-Acetyl-piperazine-1-carbonyl)-2R*,3S*-bis-(4-chloro-phenyl)-1-(2-fluoro-benzenesulfonyl)-2,3-dihydro-1H-imidazo[1,2-a]pyridin-5-one 6-(4-Acetyl-piperazine-1-carbonyl)-2R*,3S*-bis-(4-chloro-phenyl)-1-(2-fluoro-benzenesulfonyl)-2,3-dihydro-1H-imidazo[1,2-a]pyridin-5-one;

rac-cis-2,3-Bis-(4-chloro-phenyl)-1-(2-fluoro-benzenesulfonyl)-6-[4-(2-morpholin-4-yl-2-oxo-ethyl)-piperazine-1-carbonyl]-2,3-dihydro-1H-imidazo[1,2-a]pyridin-5-one;

rac-cis-2,3-Bis-(4-chloro-phenyl)-1-(2-fluoro-benzenesulfonyl)-6-(morpholine-4-carbonyl)-2,3-dihydro-1H-imidazo[1,2-a]pyridin-5-one; N-(2-{4-[rac-cis-2,3-Bis-(4-chloro-phenyl)-1-(2-fluoro-benzenesulfonyl)-5-oxo-1,2,3,5-tetrahydro-imidazo[1,2-a]pyridine-6-carbonyl]-piperazin-1-yl}-ethyl)-methanesulfonamide;

rac-cis-2,3-Bis-(4-chloro-phenyl)-1-(2-fluoro-benzenesulfonyl)-6-[4-(2-morpholin-4-yl-ethyl)-piperazine-1-carbonyl]-2,3-dihydro-1H-imidazo[1,2-a]pyridin-5-one;

rac-cis-2,3-Bis-(4-chloro-phenyl)-1-(2-fluoro-benzenesulfonyl)-6-[4-(3-methanesulfonyl-propyl)-piperazine-1-carbonyl]-2,3-dihydro-1H-imidazo[2-a]pyridin-5-one;

rac-cis-2,3-Bis-(4-chloro-phenyl)-1-(2-fluoro-benzenesulfonyl)-6-(4-methyl-piperazine-1-carbonyl)-2,3-dihydro-1H imidazo[1,2-a]pyridin-5-one; rac-cis-2,3-Bis-(4-chloro-phenyl)-6-(4-ethanesulfonyl-piperazine-1-carbonyl)-1-(2-fluoro-benzenesulfonyl)-2,3-dihydro-1H-imidazo[1,2-a]pyridin-5-one; 1-[rac-cis-2,3-Bis-(4-chloro-phenyl)-1-(2-fluoro-benzenesulfonyl)-5-oxo-1,2,3,5-tetrahydro-imidazo[1,2-a]pyridin-6-yl]-2-[4-(3-methanesulfonyl-propyl)-piperazin-1-yl]-ethane-1,2-dione;

rac-cis-2,3-Bis-(4-chloro-phenyl)-1-(2-fluoro-benzene-sulfonyl)-5-oxo-1,2,3,5-tetrahydro-imidazo[1,2-a]pyridine-6-carboxylic acid methyl ester;

rac-cis-2,3-Bis-(4-chloro-phenyl)-1-(2-fluoro-benzene-sulfonyl)-5-oxo-1,2,3,5-tetrahydro-imidazo[1,2-a]pyridine-6-carboxylic acid methylamide;

6-(4-Acetyl-piperazine-1-carbonyl)-cis-2R*,3S*-bis-(4-chloro-phenyl)-1-(2-fluoro-benzenesulfonyl)-2,3-dihydro-1H-imidazo[1,2-]pyridin-5-one; rac-3-[cis-2,3-Bis-(4-chloro-phenyl)-6-(morpholine-4-carbonyl)-5-oxo-2,3-dihydro-5H-imidazo[1,2-a]pyridine-1-sulfonyl]-benzoic acid methyl ester; rac-3-{cis-2,3-Bis-(4-chloro-phenyl)-6-[4-(2-morpholin-4-yl-2-oxo-ethyl)-piperazine-1-carbonyl]-5-oxo-2,3-dihydro-5H-imidazo[1,2-a]pyridine-1-sulfonyl}-benzoic acid methyl ester;

rac-3-[cis-2,3-Bis-(4-chloro-phenyl)-6-(4-methyl-piperazine-1-carbonyl)-5-oxo-2,3-dihydro-5H-imidazo[1,2-a]pyridine-1-sulfonyl]-benzoic acid methyl ester;

rac-3-[cis-6-(4-Acetyl-piperazine-1-carbonyl)-2,3-bis-(4-chloro-phenyl)-5-oxo-2,3-dihydro-5H-imidazo[1,2-a]pyridine-1-sulfonyl]-benzoic acid methyl ester;

rac-3-[cis-2,3-Bis-(4-chloro-phenyl)-6-(4-ethanesulfonyl-piperazine-1-carbonyl)-5-oxo-2,3-dihydro-5H-imidazo[1,2-a]pyridine-1-sulfonyl]-benzoic acid methyl ester;

rac-3-{cis-2,3-Bis-(4-chloro-phenyl)-6-[4-(2-imidazol-1-yl-ethyl)-piperazine-1-carbonyl]-5-oxo-2,3-dihydro-5H-imidazo[1,2-a]pyridine-1-sulfonyl}-benzoic acid methyl ester;

3-{(2R*,3S*)Bis-(4-chloro-phenyl)-6-[4-(2-morpholin-4-yl-2-oxo-ethyl)-piperazin-1-ylmethyl]-5-oxo-2,3-dihydro-5H-imidazo[1,2-a]pyridine-1-sulfonyl}-benzonitrile;

rac-3-[cis-2,3-Bis-(4-chloro-phenyl)-6-(morpholine-4-carbonyl)-5-oxo-2,3-dihydro-5H-imidazo[1,2-a]pyridine-1-sulfonyl]-benzonitrile;

rac-3-[(6-(4-Acetyl-piperazine-1-carbonyl)-cis-2,3-bis-(4-chloro-phenyl)-5-oxo-2,3-dihydro-5H-imidazo[1,2-a]pyridine-1-sulfonyl]-benzonitrile;

rac-3-{cis-2,3-Bis-(4-chloro-phenyl)-5-oxo-6-[4-(3,3,3-trifluoro-propionyl)-piperazine-1-carbonyl]-2,3-dihydro-5-imidazo[1,2-a]pyridine-1-sulfonyl}-benzonitrile;

3-[2R*3S*-Bis-(4-chloro-phenyl)-6-(morpholine-4-carbonyl)-5-oxo-2,3-dihydro-5H-imidazo[1,2-a]pyridine-1-sulfonyl]-benzonitrile;

3-[2R*,3S*-Bis-(4-chloro-phenyl)-6-(morpholine-4-carbonyl)-5-oxo-2,3-dihydro-5H-imidazo[1,2-a]pyridine-1-sulfonyl]-benzonitrile;

rac-cis-1-Acetyl-2,3-bis-(4-chloro-phenyl)-6-(3,4-dimethoxy-phenyl)-2,3-dihydro-1H-imidazo[1,2-a]pyridin-5-one;

rac-cis-1-Acetyl-2,3-bis-(4-chloro-phenyl)-6-(4-methanesulfonyl-phenyl)-2,3-dihydro-1H-imidazo[1,2-a]pyridin-5-one;

rac-cis-1-Acetyl-2,3-bis-(4-chloro-phenyl)-6-(3-methanesulfonyl-phenyl)-2,3-dihydro-1H-imidazo[1,2-a]pyridin-5-one;

rac-cis-1-Acetyl-6-(1-benzyl-1H-pyrazol-4-yl)-2,3-bis-(4-chloro-phenyl)-2,3-dihydro-1H-imidazo1,2-a]pyridin-5-one;

rac-cis-2,3-Bis-(4-chloro-phenyl)-1-(2-fluoro-benzenesulfonyl)-6-(3-methanesulfonyl-phenyl)-2,3-dihydro-1H-imidazo[1,2-a]pyridin-5-one;

rac-cis-2,3-Bis-(4-chloro-phenyl)-1-(2-fluoro-benzenesulfonyl)-6-(2-methyl-propenyl)-2,3-dihydro-1H-imidazo[1,2-a]pyridin-5-one;

rac-3-[cis-2,3-Bis-(4-chloro-phenyl )-6-morpholin-4-ylmethyl-5-oxo-2,3-dihydro-5H-imidazo[1,2-a]pyridine-1-sulfonyl]-benzonitrile; rac-3-[cis-6-(4-Acetyl-piperazin-1-ylmethyl)-2,3-bis-(4-chloro-phenyl)-5-oxo-2,3-dihydro-5H-imidazo[1,2-a]pyridine-1-sulfonyl]-benzonitrile and rac-3-[cis-2,3-Bis-(4-chloro-phenyl)-5-oxo-2,3-dihydro-5H-imidazo[1,2-a]pyridine-1-sulfonyl]-benzoic acid.

"Effective amount" means an amount that is effective to prevent, alleviate or ameliorate symptoms of disease or prolong the survival of the subject being treated.

"Halogen" means fluorine, chlorine, bromine or iodine.

"Hetero atom" means an atom selected from N, O and S.

"$IC_{50}$" refers to the concentration of a particular compound required to inhibit 50% of a specific measured activity. $IC_{50}$ can be measured, inter alia, as is described subsequently.

"Alkyl" denotes a straight-chained or branched saturated aliphatic hydrocarbon.

"Cycloalkyl" means a non-aromatic, partially or completely saturated monovalent cyclic hydrocarbon radical containing 3 to 8 atoms. Preferred examples of cycloalkyl groups are cyclopropyl, cyclobutyl, and cyclopentyl.

"Lower alkyl" groups denote C1-C6 alkyl groups and include methyl, ethyl, propyl, isopropyl, butyl, t-butyl, 2-butyl, pentyl, hexyl, and the like. Generally, lower alkyl is preferably C1-C4 alkyl, and more preferably C1-C3 alkyl.

"Alkoxy" denotes —O-alkyl. "Lower alkoxy" denotes —O-lower alkyl.

"Aryl" means a monovalent, monocyclic or bicyclic, aromatic carbocyclic hydrocarbon radical, preferably a 6-10 member aromatic ring system. Preferred aryl groups include, but are not limited to, phenyl, naphthyl, tolyl, and xylyl.

"Heteroaryl" means an aromatic heterocyclic ring system containing up to two rings. Preferred heteroaryl groups include, but are not limited to, thienyl, furyl, indolyl, pyrrolyl, pyridinyl, pyrazinyl, oxazolyl, thiaxolyl, quinolinyl, pyrimidinyl, imidazole and tetrazolyl.

In the case of aryl or heteroaryl which are bicyclic it should be understood that one ring may be aryl while the other is heteroaryl and both being substituted or unsubstituted.

"Heterocycle" means a substituted or unsubstituted 5 to 8 membered, mono- or bicyclic, aromatic or non-aromatic hydrocarbon, wherein 1 to 3 carbon atoms are replaced by a hetero atom selected from nitrogen,oxygen or sulfur atom. Examples include pyrrolidin-2-yl; pyrrolidin-3-yl; piperidinyl, morpholin-4-yl and the like.

"Hetero atom" means an atom selected from N, O and S.

The compounds of formulas I or II or III as well as their salts have at least one asymmetric carbon atom and therefore may be present as racemic mixtures or different stereoisomers. The various isomers can be isolated by known separation methods, e.g., chromatography. The invention includes all stereoisomers.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, as well as the particular mode of administration. The amount of active ingredient which can be combined with a carrier material to produce a single dosage form will generally be that amount of a formula I or II or III compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, sachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

"Pharmaceutically acceptable ester" refers to a conventionally esterified compound of formula 1 having a carboxyl group, which esters retain the biological effectiveness and properties of the compounds of formula I and are cleaved in vivo (in the organism) to the corresponding active carboxylic acid.

Information concerning esters and the use of esters for the delivery of pharmaceutical compounds is available in Design of Prodrugs. Bundgaard H ed. (Elsevier 1985). See also, H. Ansel et. al., Pharmaceutical Dosage Forms and Drug Delivery Systems (6th Ed. 1995) at pp. 108-109; Krogsgaard-Larsen, et. al. Textbook of Drug Design and Development (2d Ed. 1996) at pp. 152-191.

"Pharmaceutically acceptable salt" refers to conventional acid-addition salts or base-addition salts that retain the biological effectiveness and properties of the compounds of the present invention and are formed from suitable nontoxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and, quaternary ammonium hydroxides, such as for example, tetramethylammonium hydroxide. Chemical modification of a pharmaceutical compound (i.e. drug) into a salt is a technique well known to pharmaceutical chemists to obtain improved physical and chemical stability, hygroscopicity, flowability and solubility of compounds. See, e.g., H. Ansel et. al., Pharmaceutical Dosage Forms and Drug Delivery Systems (6th Ed. 1995) at pp. 196 and 1456-1457.

"Pharmaceutically acceptable," such as pharmaceutically acceptable carrier, excipient, etc., means pharmacologically acceptable and substantially non-toxic to the subject to which the particular compound is administered.

In the specification where indicated the various groups may be substituted by 1-5 or, preferably, 1-3 substituents independently selected from the group consisting of lower alkyl lower-alkenyl, lower-alkynyl, dioxo-lower-alkylene (forming e.g. a benzodioxyl group), halogen, hydroxy, CN, $CF_3$, $NH_2$, N(H, lower-alkyl), N(lower-alkyl)$_2$ aminocarbonyl, carboxy, $NO_2$, lower-alkoxy, thio-lower-alkoxy, lower-alkylsufonyl, aminosulfonyl, lower-alkylcarbonyl, lower-alkylcarbonyloxy, lower-alkoxycarbonyl, lower-alkyl-carbonyl-NH, fluoro-lower-alkyl, fluoro-lower-alkoxy, lower-alkoxycarbonyl-lower-alkoxy, carboxy-lower-alkoxy, carbamoyl-lower-alkoxy, hydroxy-lower-alkoxy, $NH_2$-lower-alkoxy, N(H, lower-alkyl)-lower-alkoxy, N(lower-alkyl)$_2$-lower-alkoxy, benzyloxy-lower-alkoxy, mono- or di-lower alkyl substituted amino-sulfonyl and lower-alkyl which can optionally be substituted with halogen, hydroxy, $NH_2$, N(H, lower-alkyl) or N(lower-alkyl)$_2$. Preferred substituents for the aryl, heteroaryl and heterocycle rings are halogen, lower alkoxy, lower alkyl carboxy, carboxy lower alkoxy and CNCompounds of the present invention as exemplified advantageously show IC50s from about 0.050 µM to about 10 µM.

The compounds of the present invention are useful in the treatment or control of cell proliferative disorders, in particular oncological disorders. These compounds and formulations containing said compounds may be useful in the treatment or control of solid tumors, such as, for example, breast, colon, lung and prostate tumors.

A therapeutically effective amount of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as continuous infusion.

The present invention also provides pharmaceutical compositions comprising at least one compound of formula I, or a pharmaceutically acceptable salt or ester thereof, and a pharmaceutically acceptable carrier or excipient.

The compounds of the present invention can be prepared according to the following Scheme 1.

Scheme 1

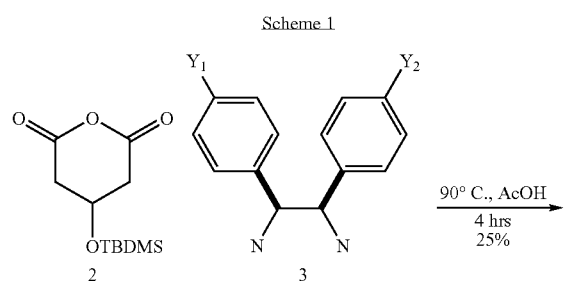

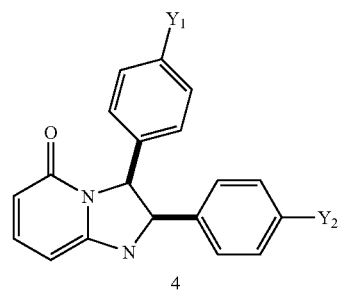

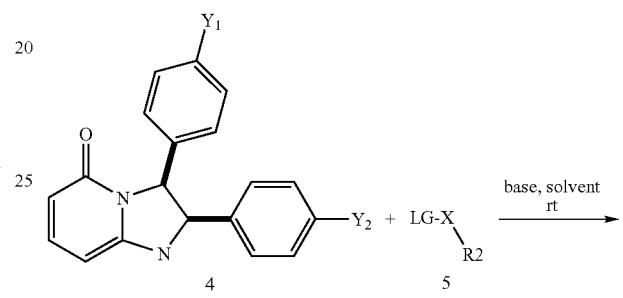

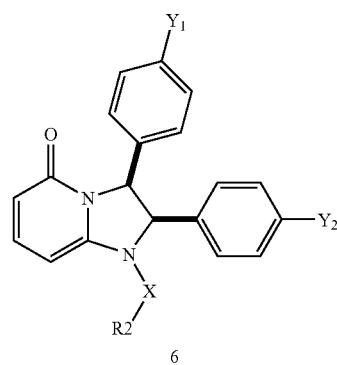

As shown in Scheme 1, the rac-cis-2,3-bis-substituted phenyl-2,8-dihydro-3H-imidazo[1,2-a]pyridin-5-one core (4) is synthesized by reaction of 4-trialkylsilyloxy-dihydro-pyran-2,6-dione (2) in acetic acid at 90° C. 4-tert-Butyldimethylsilyloxy-dihydro-pyran-2,6-dione (2) is preferred; it is possible to use acetyl-dihydro-pyran-2,6-dione for the ring forming reaction. The sulfonamide and amide derivatives of cis-2,3-bis-substituted phenyl-2,8-dihydro-3H-imidazo[1,2-a]pyridin-5-one (6) can be obtained by reaction with sulfonyl halides or acid halides, respectively in an aprotic solvent such as tetrahydrofuran (THF) in presence of an organic base such as di-isopropylethylamine (DIPEA) and a catalytic quantity of basic catalyst such as N-,N-dimethylaminopyridine.

The following diaryl-diamines are commercially available according to the Available Chemicals Directory.

| MOLSTRUCTURE | MDLNUMBER | SYSTEMATIC NAME |
| --- | --- | --- |
| (structure: (1S,2S)-1,2-diphenylethylenediamine, Chiral) | MFCD00082751 | (1S,2S)-(−)-1,2-DIPHENYLETHYLENEDIAMINE |
| (structure: (1R,2R)-1,2-diphenylethylenediamine, Chiral) | MFCD00082769 | (1R,2R)-(+)-1,2-DIPHENYLETHYLENEDIAMINE |
| (structure: meso-1,2-diphenylethylenediamine) | MFCD00274328 | MESO-1,2-DIPHENYLETHYLENEDIAMINE |
| (structure: (±)-1,2-diphenylethylenediamine) | MFCD00709169 | (+/−)-1,2-DIPHENYLETHYLENEDIAMINE |
| (structure: 1,2-bis(4-bromophenyl)... with Br and CN substituents) | MFCD00989104 | 1,2-BIS(4-BROMOPHENYL)ETHANEDIAMINE |
| (structure: 1,2-bis(4-methylphenyl)ethanediamine) | MFCD03413001 | 1,2-BIS(4-METHYLPHENYL)ETHANEDIAMINE |
| (structure: 1,2-bis(2,4-dichlorophenyl)ethanediamine) | MFCD05150369 | 1,2-BIS(2-,4-DICHLOROPHENYL)ETHANEDIAMINE |

| MOLSTRUCTURE | MDLNUMBER | SYSTEMATIC NAME |
|---|---|---|
| | MFCD05150370 | 1,2-BIS(1-NAPHTHYL)ETHYLENEDIAMINE |
| | MFCD05150371 | 1,2-BIS(4-CHLOROPHENYL)ETHANEDIAMINE |
| | MFCD06654173 | 1,2-BIS(2-HYDROXYPHENYL)ETHYLENEDIAMINE |
| | MFCD06654409 | 1,2-BIS(2-NAPHTHYL)ETHYLENEDIAMINE |
| | MFCD06658956 | 1,2-BIS(P-TOLYL)ETHYLENEDIAMINE |
| | MFCD06658957 | 1,2-BIS(4-FLUOROPHENYL)ETHYLENEDIAMINE |
| | MFCD06797063 | (1R,2R)-1,2-BIS(2,4,6-TRIMETHYLPHENYL)ETHYLENEDIAMINE |

-continued

| MOLSTRUCTURE | MDLNUMBER | SYSTEMATIC NAME |
|---|---|---|
| 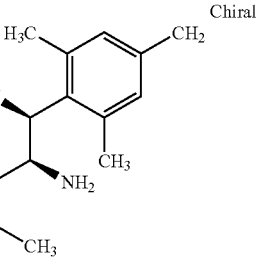 | MFCD06797064 | (1S,2S)-1,2-BIS(2,4,6-TRIMETHYLPHENYL)ETHYLENE-DIAMINE |
| 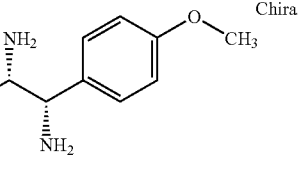 | MFCD08460191 | (S,S)-1,2-DI(4'-METHOXYPHENYL)-1,2-DIAMINOETHANE |
| 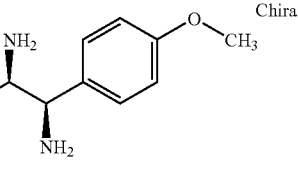 | MFCD08460192 | (1R,2R)-1,2-DI(4'-METHOXYPHENYL)-1,2-DIAMINOETHANE |

More than 100 sulfonyl chlorides of formula (7) are commercially available from suppliers such as Aldrich Chemical Company, Inc. (Milwaukee, Wis.), Lancaster Synthesis Ltd. (Lancashire, UK), TCI America (Portland, Oreg.), and Maybridge plc (Tintagel, Cornwall, UK). For the purposes of illustration, a number of commercially available sulfonyl chlorides are shown in the table below. Many other examples can be found by consulting the Available Chemicals Directory (MDL Information Systems, San Leandro, Calif.) or SciFinder (Chemical Abstracts Service, Columbus, Ohio).

| Name | Supplier |
|---|---|
| 1-Naphthalene-sulfonyl chloride | TCI America, Portland, OR |
| 2,4-Difluoro-benzene-sulfonyl chloride | Aldrich Chemical Company, Inc., Milwaukee, WI |
| 2,5-Dichloro-benzene-sulfonyl chloride | Aldrich Chemical Company, Inc., Milwaukee, WI |
| 2-Chloro-6-methylbenzene-sulfonyl chloride | Lancaster Synthesis Ltd., Lancashire, UK |
| 2-Chloro-benzene-sulfonyl chloride | Aldrich Chemical Company, Inc., Milwaukee, WI |
| 2-Mesitylene-sulfonyl chloride | Lancaster Synthesis Ltd., Lancashire, UK |
| 3-Chloro-2-methylbenzene-sulfonyl chloride | Maybridge plc, Tintagel, Cornwall, UK |
| 3-Nitro-benzene-sulfonyl chloride | Aldrich Chemical Company, Inc., Milwaukee, WI |
| 3-Pyridinesulfonyl chloride hydrochloride | Combi-Blocks, LLC, San Diego, CA |
| 4-Methoxy-2,3,6-trimethyl-benzene-sulfonyl chloride | Lancaster Synthesis Ltd., Lancashire, UK |
| 8-Quinoline-sulfonyl chloride | Maybridge plc, Tintagel, Cornwall, UK |
| O-Toluene-sulfonyl chloride | TCI America, Portland, OR |

Sulfonyl chlorides of formula (7) can also be made by reactions that are well known in the field of organic synthesis such as those outlined below

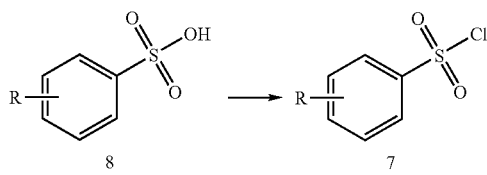

Scheme 2

For example, sulfonyl chlorides of formula (7) can be made from a sulfonic acid of formula (8) as shown in Scheme 2. The chlorination of a benzenesulfonic acid of formula (8) can be accomplished conveniently by treating it with a chlorinating agent such as thionyl chloride or phosphorus oxychloride or phosphorus pentachloride, in the optional additional presence of a catalytic amount of N,N-dimethylformamide, at a temperature between about 0 degrees and about 80 degrees depending on the reactivity of the chlorinating agent.

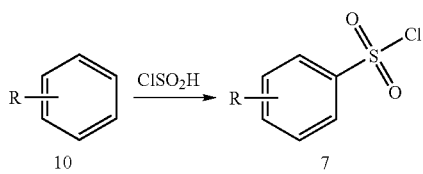

Scheme 3

Sulfonyl chlorides of formula (7) can be made by electrophilic aromatic substitution of an aromatic compound of formula (10) as shown in Scheme 3. As is known to one of average skill in the art, this process is suitable for the preparation of arylsulfonyl chlorides with particular substitution patterns, such as for example where there is an ortho/para directing substituent ortho or para to the site of introduction of the sulfonyl group. The reaction is conveniently carried out by treating the aromatic compound of formula (10) with chlorosulfonic acid in the absence of solvent and then heating the mixture at a temperature between about 70 degrees and about 100 degrees.

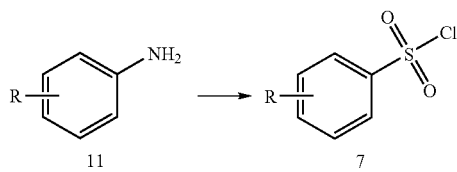

Scheme 4

Sulfonyl chlorides of formula (7) can also be made from anilines of formula (11) by a diazotization/sulfonylation reaction sequence as shown in Scheme 6. The diazotization reaction is conveniently carried out by treating the aniline of formula (11) or an acid addition salt thereof (such as the hydrochloride salt) in aqueous solution in the presence of a mineral acid such as hydrochloric acid or sulfuric acid with an alkali metal nitrite salt such as sodium nitrite at a temperature less than 10 degrees, preferably around 0 degrees. The diazonium salt obtained in this way can be converted directly to the sulfonyl chloride using a variety of reagents and conditions which are known in the field of organic synthesis. Examples of suitable reagents include sulfur dioxide and copper(I) chloride or copper(II) chloride in acetic acid/water, or thionyl chloride and copper(I) chloride or copper(II) chloride in water according to the procedure of P. J. Hogan (U.S. Pat. No. 6,531,605). For example, the sulfonylation reaction can be carried out by adding the solution of the diazonium salt, prepared as described above, to a mixture of sulfur dioxide and copper(II) chloride in a suitable inert solvent, such as glacial acetic acid, at a temperature around 0 degrees.

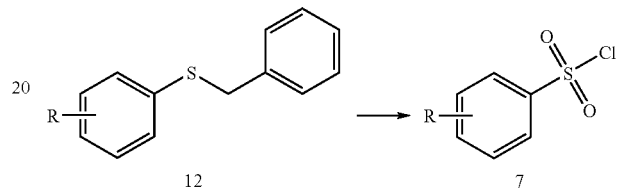

Scheme 5

Sulfonyl chlorides of formula (7) can also be made from an aryl benzyl sulfide of formula (12) by an oxidative chlorination reaction as shown in Scheme 5. The reaction is conveniently carried out by bubbling chlorine gas into a solution or suspension of the aryl benzyl sulfide of formula (12) in a suitable inert solvent such as a mixture of acetic acid and water at a temperature around room temperature.

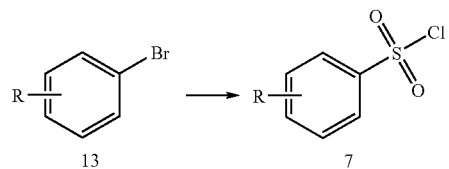

Scheme 6

Sulfonyl chlorides of formula (7) can also be made as shown in Scheme 6 from an aryl bromide of formula (13) by metal-halogen exchange, followed by reaction of the organometallic intermediate with sulfur dioxide to give an arylsulfonate salt, followed by reaction with sulfuryl chloride to give the arylsulfonyl chloride. The reaction can be carried out by treating the aryl bromide with an organometallic reagent such as n-butyl lithium or preferably sec-butyl lithium, in the optional additional presence of tetramethylethylenediamine (TMEDA) in a suitable inert solvent such as tetrahdyrofuran (THF) or diethyl ether at low temperature (for example, around −78 degrees) to give the aryllithium intermediate. This can then be reacted, without isolation, with a mixture of sulfur dioxide and a solvent such as diethyl ether, again at low temperature, such as for example between about −78 degrees and about −60 degrees. The resulting arylsulfonate salt can then be converted to the aryisulfonyl chloride, again without isolation of the intermediate, by treatment with sulfuryl chloride at a temperature around 0 degrees.

Scheme 7

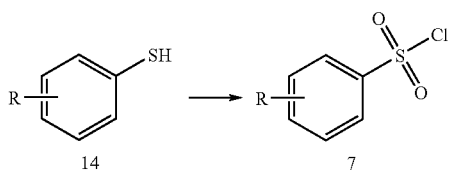

Sulfonyl chlorides of formula (7) can be made from an aryl thiol of formula (14) by oxidation using chlorine as shown in Scheme 7 For example, the reaction can be carried out by treating the aryl thiol of formula (14) with a solution of chlorine in an inert solvent such as glacial acetic acid at a temperature around 0 degrees.

Scheme 8

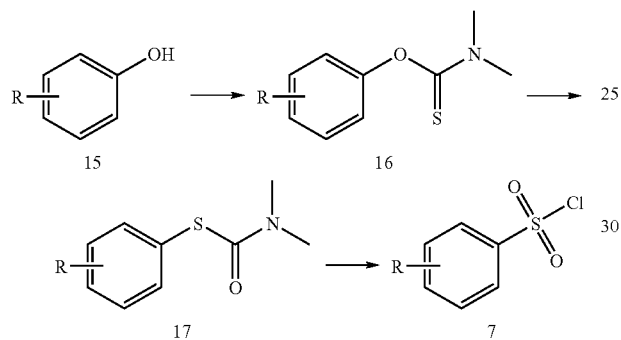

Sulfonyl chlorides of formula (7) can be made from a phenol of formula (15) through a sequence of reactions outlined in Scheme 8. The phenol of formula (15) can be converted to the O-aryl-N,N'-dialkylthiocarbamate of formula (16) by reaction with an N,N'-dialkylthiocarbamoyl chloride in an inert solvent in the presence of a base. The resulting O-aryl-N,N'-dialkylthiocarbamate of formula (16) can be rearranged to the S-aryl-N,N'-dialkylthiocarbamate of formula (17) by heating neat at high temperature such as at around 250 degrees. The S-aryl-N,N'-dialkylthiocarbamate of formula (17) can then be converted to the sulfonyl chloride of formula (7) by oxidation using chlorine in a suitable inert solvent such as a mixture of formic acid and water at a temperature around 0 degrees. An example of the use of this process for the preparation of sulfonyl chlorides can be seen in V. Percec et al. *J. Org. Chem.* 2001, 66 2104.

More than one thousands acid chlorides are listed as commercially available in the Available Chemicals Directory. Acid chlorides are also available by reaction of the corresponding acid with thionyl chloride or oxalyl chloride in presence of a catalytic quantity of dimethylformamide. Such preparations are well known to those skilled in the art. The preparation of acid chlorides with thionyl chlorides has been described in *Vogel's Textbook of Practical Organic Chemistry*, 5$^{th}$ edition B. S. Furniss et al. Longman Scientific and Technical (1989) pp 692-693.

Scheme 9

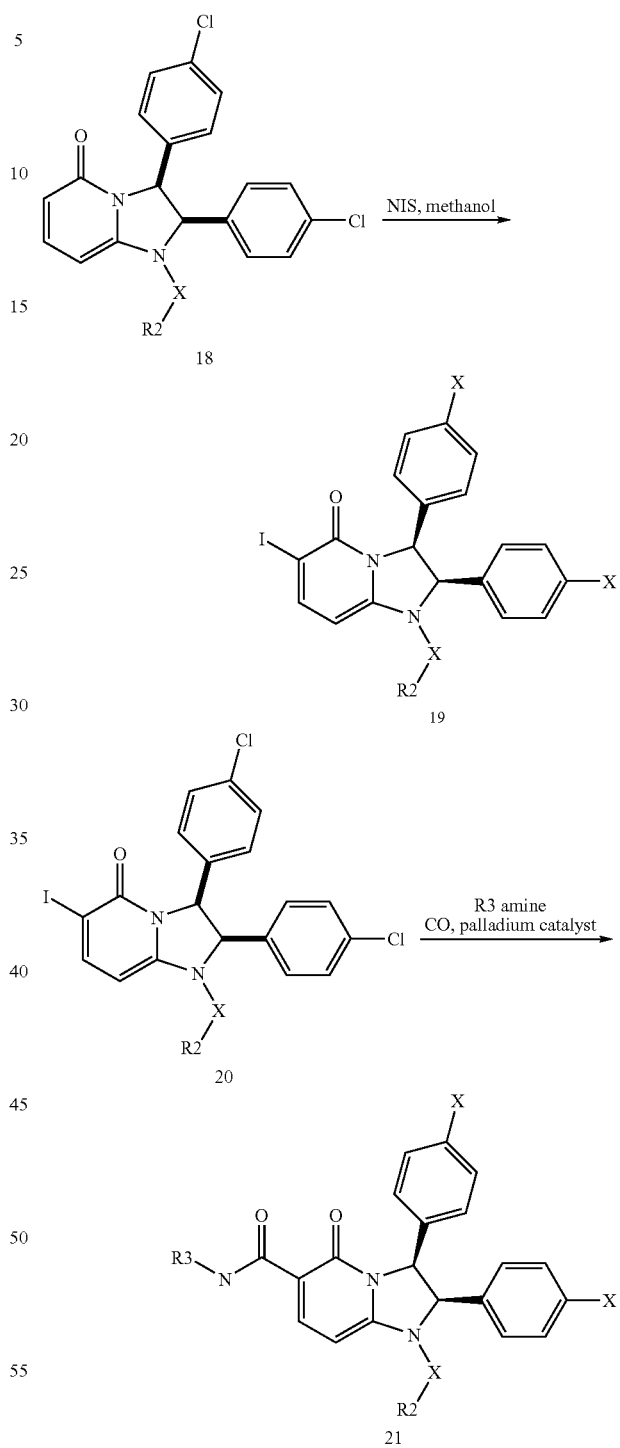

Formation of cis-2,3-bis-phenyl-6-iodo-1,2,3,8-tetrahydro-imidazo[1,2-a]pyridin-5-one derivatized at the N-1 position (19) is possible by treatment of the cis-2,3-bis-phenyl-1,2,3,8-tetrahydro-imidazo[1,2-a]pyridin-5-one (18) with N-iodo-succinimide (NIS) in protic solvents such as methanol. The 6 position is iodinated selectively. Other halogens may be added in this fashion (e.g., by reaction with N-bromosuccinimide), but iodination is preferred. The 6-amido derivatives (21) as shown in Scheme 9 may be formed by reaction of cis-2,3-bis-phenyl-6-iodo-1,2,3,8-tetrahydro-imidazo[1,2-a]pyridin-5-one derivatives (20) with carbon monoxide, preferably at 50 pounds per square inch and with primary or secondary amines under palladium catalytic systems, preferably palladium tetrakis-triphenyl phosphine (Pd (PPh3)$_4$) in presence of base, preferably DIPEA. The reaction mixture is heated, for example, at 60° C. for 1 hour.

It is possible to create the 6-aryl derivatives of the cis-2,3-bis-phenyl-6-iodo-1,2,3,8-tetrahydro-imidazo[1,2-a]pyridin-5-one core also derivatized at the N-1 position (23) by reaction of the 6-iodo derivative (22) with boronic acids under palladium catalyzed conditions according to Scheme 10 below.

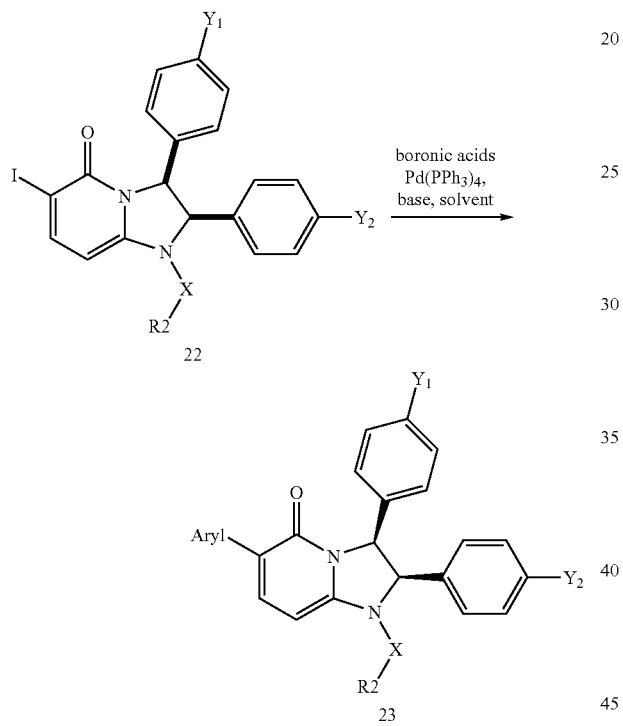

Scheme 10

The conditions of this method are disclosed in many publications which have been reviewed by A. Suzuki in an article entitled "The Suzuki reaction with arylboron compounds in arene chemistry" in *Modern Arene Chemistry* 2002, 53-106. In carrying out this reaction any of the conditions conventional in a Suzuki reaction can be utilized.

Generally these reactions are carried out in the presence of a metal catalyst such as a palladium catalyst utilizing any conventional organic solvent and a weak inorganic base. Among the preferred organic solvents are the polar aprotic solvents. Any conventional polar aprotic solvents can be utilized in preparing compounds of the invention. Suitable solvents are customary, especially higher-boiling, solvents, e.g. dimethoxyethane. The weak inorganic base can be a carbonate or bicarbonate, such as potassium carbonate or cesium carbonate.

Commercially Available Boronic Acids Used in this Procedure are Listed Below.

The Available Chemicals Database (ACD) indicates the availability of greater than seven hundred commercially available aryl boronic acids. Some boronic acids useful for the preparation of compounds of the invention are listed below.

| Boronic acid |
| --- |
| 3-CHLORO-PHENYLBORONIC ACID |
| 3-CHLORO-5-METHYLPHENYLBORONIC ACID |
| 3-CHLORO-6-METHOXYPHENYLBORONIC ACID |
| 3-CHLORO-4-FLUOROPHENYLBORONIC ACID |
| 3-CHLORO-4-METHYLPHENYLBORONIC ACID |
| 3-CHLORO-2-METHYLPHENYLBORONIC ACID |
| 4-CHLORO-3-METHYLPHENYLBORONIC ACID |
| 2,4-DI-CHLOROPHENYLBORONIC ACID |
| 4-CHLORO-2-METHYLPHENYLBORONIC ACID |
| 4-CHLORO-2-METHOXYLPHENYLBORONIC ACID |
| 4-CHLORO-2-ETHOXYLPHENYLBORONIC ACID |
| 4-CHLORO-3-AMINOPHENYLBORONIC ACID |
| 3-ISOPROPYLPHENYLBORONIC ACID |
| 2,5-DICHLOROPHENYLBORONIC ACID |
| THIOPHENE-3-BORONIC ACID |
| 2-METHYLPHENYLBORONIC ACID |
| 3-METHYLPHENYLBORONIC ACID |
| (2-HYDROXYMETHYLPHENYL)BORONIC ACID DEHYDRATE |
| (3-HYDROXYMETHYLPHENYL)BORONIC ACID DEHYDRATE |
| 4-HYDROXYPHENYL)BORONIC ACID DEHYDRATE |
| 2-METHOXYPHENYLBORONIC ACID |
| 3-METHOXYPHENYLBORONIC ACID |
| 2-TRIFLUOROMETHOXYPHENYLBORONIC ACID |
| 3-TRIFLUOROMETHOXYPHENYLBORONIC ACID |
| 6-FLUORO-2-METHOXYPHENYLBORONIC ACID |
| 2-FLUORO-3-METHOXYPHENYLBORONIC ACID |
| 5-FLUORO-2-METHOXYPHENYLBORONIC ACID |
| 3,4-DIMETHOXYPHENYLBORONIC ACID |
| 2,5-DIMETHOXYPHENYLBORONIC ACID |
| 5-BENZO[1,3]DIOXOLEBORONIC ACID |
| 2,3,4-TRIMETHOXYPHENYLBORONIC ACID |
| 1H-INDOLE-5-BORONIC ACID |
| QUINOLINE-8-BORONIC ACID |

These boronic acids are also available from other suppliers that may not necessarily be listed in the ACD.

| | | |
| --- | --- | --- |
| 3-Fluoro-6-(4,4,5,5-tetramethyl-[1,3,2]dioxaborolan-2-yl)pyridine | ATLANTIC SCIENTIFIC CO., INC., JERSEY CITY, NJ, | 791819-04-0 |
| Quinoline-2-boronic acid | LANCASTER | 745784-12-7 |
| 3-Chloro-6-(4,4,5,5-tetramethyl-[1,3,2]dioxaborolan-2-yl)pyridine | ATLANTIC SCIENTIFIC CO., INC., JERSEY CITY, NJ, | 652148-93-1 |
| 6-Chloropyridine-2-boronic acid pinacol ester | INTERCHIM, MONTLUCON, FRANCE | 652148-92-0 |
| Boronic acid, (2-methyl-4-pyrimidinyl)- | CHEMSTEP, TALENCE, FRANCE | 647853-31-4 |

| -continued | | |
|---|---|---|
| Boronic acid, (3-methoxy-2-pyridinyl)- | CHEMSTEP, TALENCE, FRANCE | 500707-34-6 |
| Boronic acid, (6-methoxy-2-pyridinyl)- | CHEMSTEP, TALENCE, FRANCE | 372963-51-4 |
| Boronic acid, (6-methyl-2-pyridinyl)- | CHEMSTEP, TALENCE, FRANCE | 372963-50-3 |
| Boronic acid, (5-methyl-2-pyridinyl)- | CHEMSTEP, TALENCE, FRANCE | 372963-49-0 |
| Boronic acid, (4-methyl-2-pyridinyl)- | CHEMSTEP, TALENCE, FRANCE | 372963-48-9 |
| Boronic acid, 2-pyridinyl- | CHEMSTEP, TALENCE, FRANCE | 197958-29-5 |

Phenyl boronic acids and boronic esters useful in the preparation of compounds of formula 25 may be commercially available or they can be made by reactions that are well known in the field of organic synthesis, such as those outlined below. Aryl boronic acids and aryl boronic esters are formed by treatment of aryl halides (24) with an organometallic reagent such as n-butyl lithium followed by treatment with boron triisopropoxide or 4,4,4',4',5,5,5',5'-octamethyl-2,2'-bi-1,3,2-dioxaborolane followed by acidic work-up as is well known to those skilled in the art.

It is possible to create the 6-aminomethyl analogs of the cis-2,3-bis-phenyl-6-iodo-1,2,3,8-tetrahydro-imidazo[1,2-a]pyridin-5-one core also derivatized at the N-1 position (28) as shown in Scheme 12. cis-2,3-Bis-phenyl-6-iodo-1,2,3,8-tetrahydro-imidazo[1,2-a]pyridin-5-one core also derivatized at the N-1 position (22) is reacted in an aprotic solvent, preferably 1,2-dimethoxy ethane, with 2,2-dimethylethenylboronic acid boronic acid, and inorganic based preferably cerium carbonate, and a palladium catalyst, preferably [1,1'-bis(diphenylphosphino)ferrocene]dichloropalladium(II) ($PdCl_2$(dppf)) with heated preferably 60° C. for one hour. The resultant olefin (26) is oxidized to the corresponding aldehyde with ozone in a solvent mixture such as methanol and dichloromethane. The work up of the ozonoloysis reaction provides 6-carbaldehyde (27). This aldehyde (27) is treated with excess amine in a solvent such as THF; further the reaction mixture is acidified with an acid such as acetic acid; finally the reductant sodium cyanoborohydride is added to this reaction mixture to effect transformation to the 6-aminomethyl analogs (28).

Scheme 11

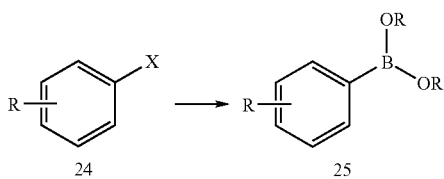

Scheme 12

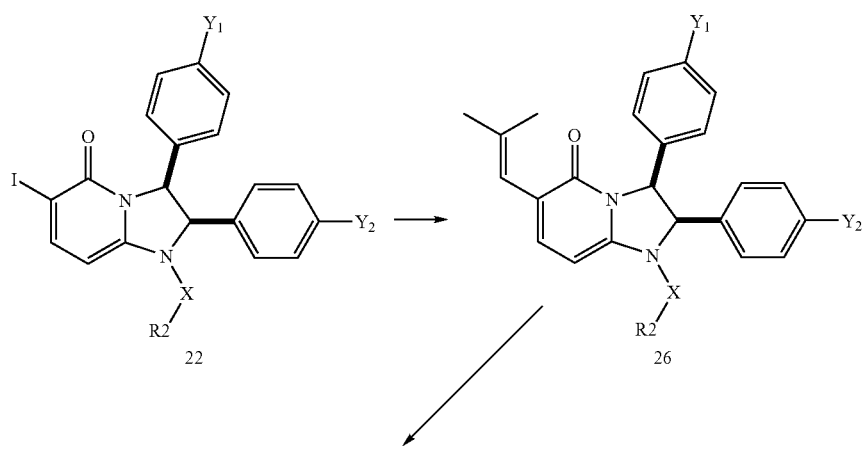

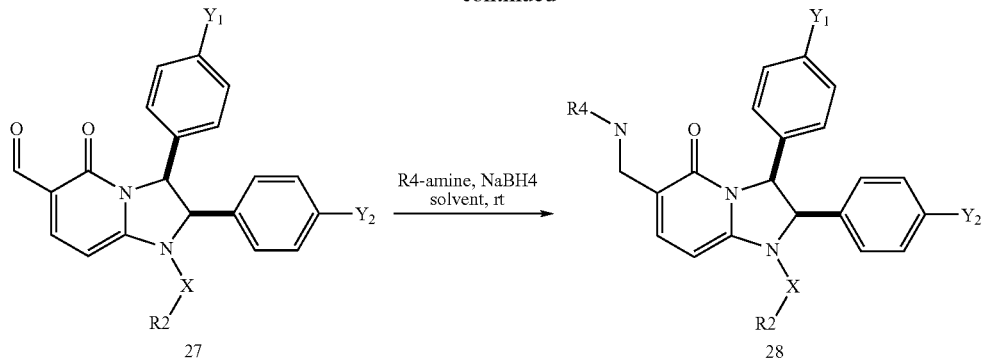

Transformation of functional groups contained within the moieties these structures such as ester to acids is conducted according to standard methods in organic chemistry, known to those skilled in the art.

If it is desired to prepare the optically active compounds of formula 1, the enantiomers of formula 1 can be separated using super critical fluid chiral chromatography. The chiral stationary phase Diacel ChiralPak OD or AD can be used. The absolute stereochemistry has yet to be determined for the compounds comprised in this invention.

The following examples and references are provided to aid the understanding of the present invention, the true scope of which is set forth in the appended claims.

EXAMPLES

Reagents were purchased from Aldrich, Sigma, Maybridge, Advanced ChemTech, and Lancaster or other suppliers as indicated below and used without further purification. LC/MS (liquid chromatography/mass spectroscopy) spectra were recorded using the following system. For measurement of mass spectra, the system consists of a Micromass Platform II spectrometer: ES Ionization in positive mode (mass range: 150-1200 amu). The simultaneous chromatographic analytical separation was achieved with the following HPLC system: ES Industries Chromegabond WR C-18 3 u 120 Å (3.2× 30mm) column cartridge; Mobile Phase A: Water (0.02% TFA) and Phase B: Acetonitrile (0.02% TFA); gradient 10% B to 90% B in 3 minutes; equilibration time of 1 minute; flow rate of 2 mL/minute.

Compounds were purified by HPLC Method A unless otherwise indicated.

HPLC Method A:

Samples that required purification were purified with a Waters mass-directed purification system utilizing a Waters 600 LC pump, Waters Xterra C18 column (5 μm, 19 mm×50 mm) and Micromass ZQ mass spectrometer, operating in positive ion electrospray ionization mode. Mobile phases A (0.1% formic acid in water) and B (0.1% formic acid in acetonitrile) were used in a gradient; 5% B to 30% B over 7 mins, held for 1 min, at a flow rate of 20 mL/min. Gradients in which formic acid was substituted with trifluoroacetic acid are also possible; gradients without use of acid modifiers are also possible.

Super critical fluid chromatography separations were performed using a Mettler-Toledo Multigram system with the following typical conditions: 100 bar, 30° C., 2.0 mL/min eluting a 12 mm Diacel OD column eluted with 40% MeOH or other percentage as appropriate the to the specific compound in super critical fluid $CO_2$. In the case of analytes with basic amino groups, 0.2% isopropyl amine was added to the methanol modifier.

LIST OF ABBREVIATIONS

DCE 1,2-dichloroethane
DCM dichloromethane
DIPEA diisopropylethylamine
DME dimethoxyethane
DMF N,N-dimethylformamide
DMSO dimethylsulfoxide
EtOAc ethyl acetate
FCC flash column chromatography
HPLC high pressure chromatography
MeOH methyl alcohol
MW microwave
$NaHCO_3$ sodium bicarbonate
NIS N-iodosuccinimide
NJP 1-methyl-2-pyrrolidinone
($PdCl_2$(dppf)) [1,1'-Bis(diphenylphosphino)ferrocene] dichloropalladium(II)
rt room temperature
TEA triethylamine
THF tetrahydrofuran
TBDMS tert-butyl dimethylsilyI

Example 1 rac-cis-2,3-bis-(4-chloro-phenyl)-2,3-dihydro-1H-imidazo[1,2-a]pyridin-5-one

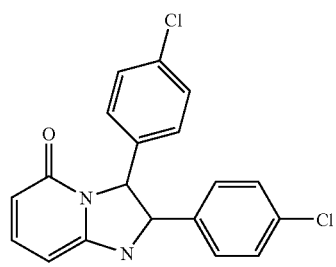

To a solution of 3-(tert-butyldimethylsilyloxy)-glutaric anhydride (4.36 g, 17.8 mmol) in acetic acid (50 mL), 1,2-bis-(4-chloro-phenyl)-1 2-diamine (5 g, 17.8 mmol) was added and stirred at 110° C. for 4 hrs.

The solvent was removed under reduced pressure. The residue was diluted with EtOAc. The pH was adjusted to basic with sat. NaHCO$_3$, and the aqueous was separated. The aqueous layer was extracted with EtOAc. The combined organic layers were washed with brine, dried with anhydrous Na$_2$SO$_4$, and concentrated under reduced pressure. FCC (5% MeOH/EtOAc) provides 1 as a solid (1.02 g, yield 16%)

$^1$H NMR (CDCl$_3$): δ 7.33 (dd, 1H), 7.13 (d, 2H), 7.05 (d, 2H), 6.95 (d, 2H), 6.64 (d, 2H), 5.96 (dd, 1H), 5.76 (d, 1H), 5.60 (d, 1H), 5.37 (dd, 1H), 4.89 (brs, 1H).

General Method for the Preparation of Analogs of 1: Method A

To a solution of 1 (50 mg, 0.14 mmol) in THF (2 mL), DIPEA (0.1 mL, 0.6 mmol) and DMAP (5 mg, 0.04 mmol) were added, followed by acetyl chloride, isocyanate, or sulfonyl chloride (80 μL, or 80 mg if solid), and stirred at rt overnight.

The reaction was diluted with EtOAc (6 mL), washed with water (3 mL), dried under reduced pressure.

Preparative HPLC provided the title compound.

Example 2

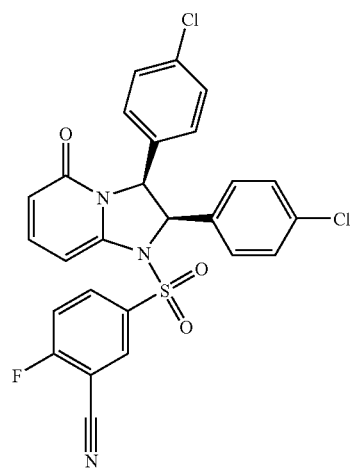

rac-5-[-cis-2,3-Bis-(4-chloro-phenyl)-5-oxo-2,3-dihydro-5H-imidazo[1,2-a]pyridine-1-sulfonyl]-2-fluoro-benzonitrile was prepared according to general method A by reaction of rac-cis-bis-(4-chloro-phenyl)-2,3-dihydro-1H-imidazo[1,2-a]pyridin-5-one with 3-cyano-4-fluorobenzenesulfonyl chloride. The compound was isolated by preparative HPLC. The expected product was characterized by LC/MS (M+H) where the mass was observed as 540.07, the expected mass is 539. LC/MS indicated a purity of 100% as measured by UV 214 nM.

Example 3

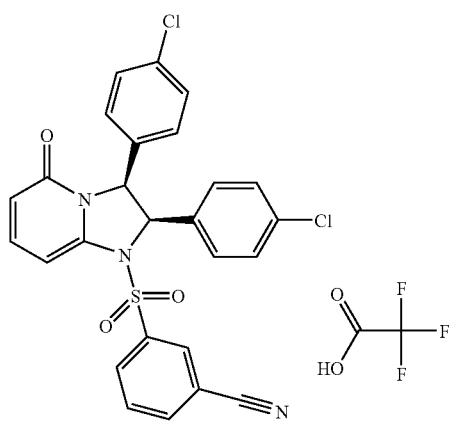

rac-3-[cis-2,3-Bis-(4-chloro-phenyl)-5-oxo-2,3-dihydro-5H-imidazo[1,2-a]pyridine-1-sulfonyl]-benzonitrile; compound was prepared according to general method A by reaction of rac-cis-bis-(4-chloro-phenyl)-2,3-dihydro-1H-imidazol[1,2-a]pyridin-5-one with 3-cyano-benzenesulfonyl chloride. The compound was isolated by preparative HPLC. The expected product was characterized by LC/MS (M+H) where the mass was observed as 521.99; the expected mass is 521. LC/MS indicated a purity of 100% as measured by UV 214 nM.

Example 4

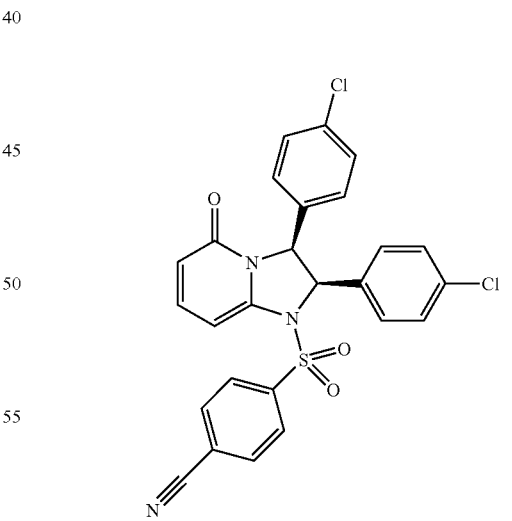

rac-4-[-cis-2,3-Bis-(4-chloro-phenyl)-5-oxo-2,3-dihydro-5H-imidazo[1,2-a]pyridine-1-sulfonyl]-benzonitrile was prepared according to general method A by reaction of rac-cis-bis-(4-chloro-phenyl)-2,3-dihydro-1H-imidazo[1,2-a] pyridin-5-one with 4-cyanobenzenesulfonyl chloride. The compound was isolated by preparative HPLC. The expected product was characterized by LC/MS (M+H) where the mass was observed as 521.91, the expected mass is 521. LC/MS indicated a purity of 100% as measured by UV 214 nM.

Example 5

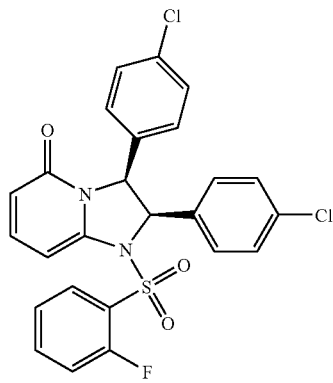

rac-cis-2,3-Bis-(4-chloro-phenyl)-1-(2-fluoro-benzenesulfonyl)-2,3-dihydro-1H-imidazo[1,2-a]pyridin-5-one was prepared according to general method A by reaction of rac-cis-bis-(4-chloro-phenyl)-2,3-dihydro-1H-imidazo[1,2-a]pyridin-5-one with 2-fluorobenzenesulfonyl chloride. The compound was isolated by preparative HPLC. The expected product was characterized by LC/MS (M+H) where the mass was observed as 514.92; the expected mass is 514. LC/MS indicated a purity of 100% as measured by UV 214 nM.

Example 6

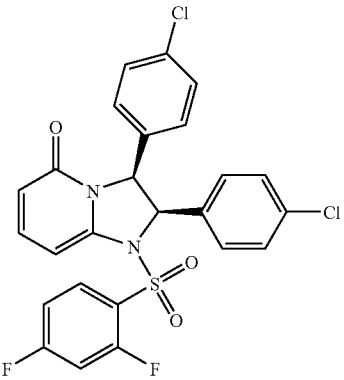

rac-cis-2,3-Bis-(4-chloro-phenyl)-1-(2,4-difluoro-benzenesulfonyl)-2,3-dihydro-1H-imidazo[1,2-a]pyridin-5-one was prepared according to general method A by reaction of rac-cis-bis-(4-chloro-phenyl)-2,3-dihydro-1H-imidazo[1,2-a]pyridin-5-one with 2,4-difluorobenzenesulfonyl chloride. The compound was isolated by preparative HPLC. The expected product was characterized by LC/MS (M+H) where the mass was observed as 533.08, the expected mass is 532. LC/MS indicated a purity of 100% as measured by UV 214 nM.

Example 7

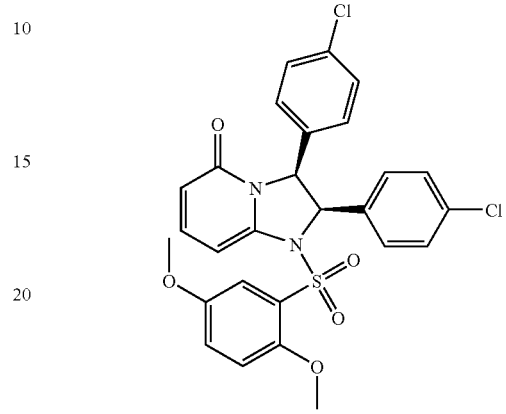

rac-cis-2,3-Bis-(4-chloro-phenyl)-1-(2,5-dimethoxy-benzenesulfonyl)-2,3-dihydro-1H-imidazo[1,2-a]pyridin-5-one was prepared according to general method A by reaction of rac-cis-bis-(4-chloro-phenyl)-2,3-dihydro-1H-imidazo[1,2-a]pyridin-5-one with 2,5-dimethoxybenzenesulfonyl chloride. The compound was isolated by preparative HPLC. The expected product was characterized by LC/MS (M+H) where the mass was observed as 557.09; the expected mass is 556.1 LC/MS indicated a purity of 100% as measured by UV 214 nM.

Example 8

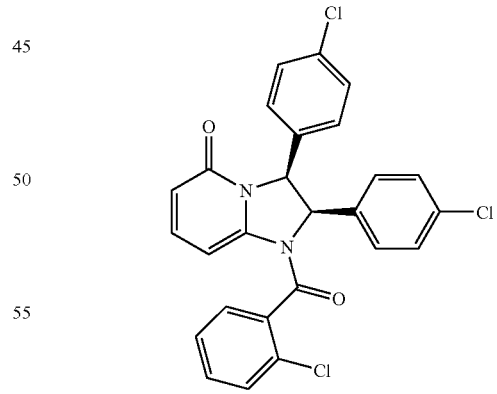

rac-cis-1-(2-Chloro-benzoyl)-2,3-bis-(4-chloro-phenyl)-2,3-dihydro-1H-imidazo[1,2-a]pyridin-5-one was prepared according to general method A by reaction of rac-cis-bis-(4-chloro-phenyl)-2,3-dihydro-1H-imidazo[1,2-a]pyridin-5-one with 2-chlorobenzoyl chloride. The compound was isolated by preparative HPLC. The expected product was characterized by LC/MS (M+H) where the mass was observed as 495.11; the expected mass is 494. LC/MS indicated a purity of 100% as measured by UV 214 nM.

Example 9

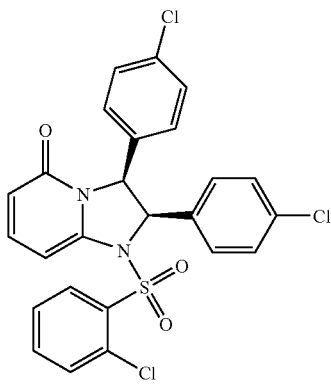

rac-cis-1-(2-Chloro-benzenesulfonyl)-2,3-bis-(4-chloro-phenyl)-2,3-dihydro-1H-imidazo[1,2-a]pyridin-5-one was prepared according to general method A by reaction of rac-cis-bis-(4-chloro-phenyl)-2,3-dihydro-1H-imidazo[1,2-a]pyridin-5-one with 2-chlorobenzenesulfonyl chloride. The compound was isolated by preparative HPLC. The expected product was characterized by LC/MS (M+H) where the mass was observed as 531.06; the expected mass is 530. LC/MS indicated a purity of 90.55% as measured by UV 214 nM.

Example 10

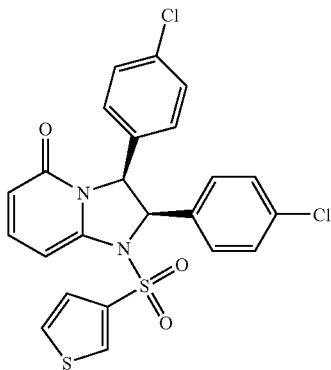

rac-cis-2,3-Bis-(4-chloro-phenyl)-1-(thiophene-3-sulfonyl)-2,3-dihydro-1H-imidazo[1,2-a]pyridin-5-one was prepared according to general method A by reaction of rac-cis-bis-(4-chloro-phenyl)-2,3-dihydro-1H-imidazo[1,2-a]pyridin-5-one with 3-thiophenesulfonyl chloride. The compound was isolated by preparative HPLC. The expected product was characterized by LC/MS (M+H) where the mass was observed as 503.06; the expected mass is 502. LC/MS indicated a purity of 100% as measured by UV 214 nM.

Example 11

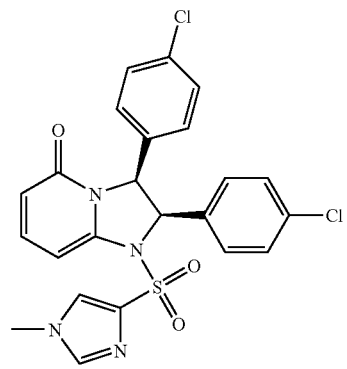

rac-cis-2,3-Bis-(4-chloro-phenyl)-1-(1-methyl-1H-imidazole-4-sulfonyl)-2,3-dihydro-1H-imidazo[1,2-a]pyridin-5-one was prepared according to general method A by reaction of rac-cis-bis-(4-chloro-phenyl)-2,3-dihydro-1H-imidazo[1,2-a]pyridin-5-one with 1-methyl-1H-imidazole-4-sulfonyl chloride. The compound was isolated by preparative HPLC. The expected product was characterized by LC/MS (M+H) where the mass was observed as 501.09; the expected mass is 500. LC/MS indicated a purity of 100% as measured by UV 214 nM.

Example 12

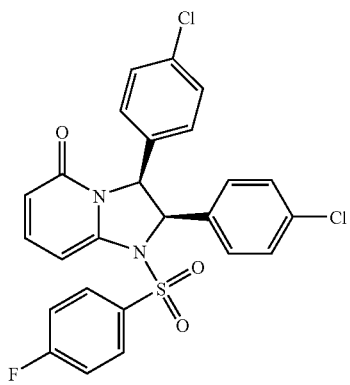

rac-cis-2,3-Bis-(4-chloro-phenyl)-1-(4-fluoro-benzenesulfonyl)-2,3-dihydro-1H-imidazo[1,2-a]pyridin-5-one was prepared according to general method A by reaction of rac-cis-bis-(4-chloro-phenyl)-2,3-dihydro-1H-imidazo[1,2-a]pyridin-5-one with 4-FLUORObenzenesulfonyl chloride. The compound was isolated by preparative HPLC. The expected product was characterized by LC/MS (M+H) where the mass was observed as 515.15; the expected mass is 514. LC/MS indicated a purity of 100% as measured by UV 214 nM.

Example 13

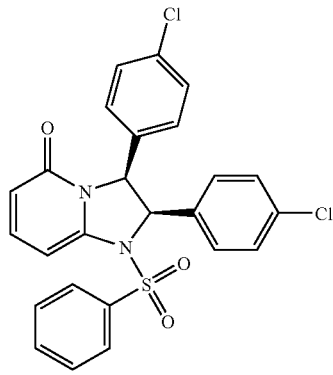

rac-cis-1-Benzenesulfonyl-rac-cis-bis-(4-chloro-phenyl)-2,3-dihydro-1H-imidazo[1,2-a]pyridin-5-one was prepared according to general method A by reaction of rac-cis-bis-(4-chloro-phenyl)-2,3-dihydro-1H-imidazo[1,2-a]pyridin-5-one with benzenesulfonyl chloride. The compound was isolated by preparative HPLC. The expected product was characterized by LC/MS (M+H) where the mass was observed as 497.15; the expected mass is 496. LC/MS indicated a purity of 93.66% as measured by UV 214 nM.

Example 14

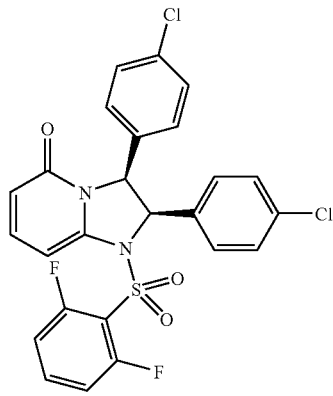

rac-cis-2,3-Bis-(4-chloro-phenyl)-1-(2,6-difluoro-benzenesulfonyl)-2,3-dihydro-1H-imidazo[1,2-a]pyridin-5-one was prepared according to general method A by reaction of rac-cis-bis-(4-chloro-phenyl)-2,3-dihydro-1H-imidazo[1,2-a]pyridin-5-one with 2,6-difluorobenzenesulfonyl chloride, The compound was isolated by preparative HPLC. The expected product was characterized by LC/MS (M+H) where the mass was observed as 533.06; the expected mass is 532. LC/MS indicated a purity of 100% as measured by UV 214 nM.

Example 15

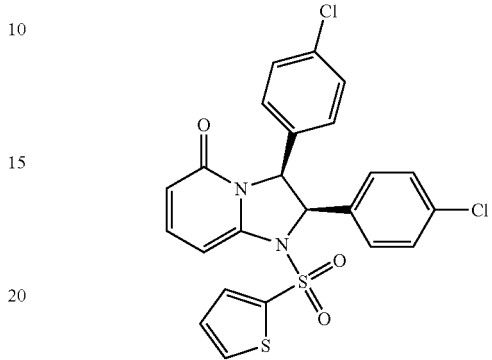

rac-cis-2,3-Bis-(4-chloro-phenyl)-1-(thiophene-2-sulfonyl)-2,3-dihydro-1H-imidazo[1,2-a]pyridin-5-one was prepared according to general method A by reaction of rac-cis-bis-(4-chloro-phenyl)-2,3-dihydro-1H-imidazo[1,2-a] pyridin-5-one with thiophene-2-sulfonyl chloride. The compound was isolated by preparative HPLC. The expected product was characterized by LC/MS (M+H) where the mass was observed as 503.04; the expected mass is 502. LC/MS indicated a purity of 100% as measured by UV 214 nM.

Example 16

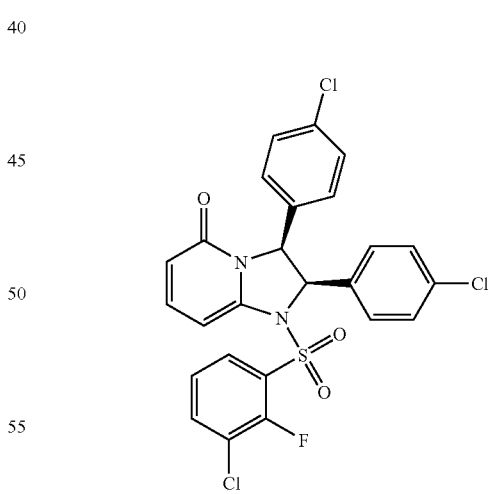

rac-cis-1-(3-Chloro-2-fluoro-benzenesulfonyl)-2,3-bis-(4-chloro-phenyl)-2,3-dihydro-1H-imidazo[1,2-a]pyridin-5-one was prepared according to general method A by reaction of rac-cis-bis-(4-chloro-phenyl)-2,3-dihydro-1H-imidazo[1,2-a]pyridin-5-one with 3-chloro-2-fluorobenzenesulfonyl chloride. The compound was isolated by preparative HPLC. The expected product was characterized by LC/MS (M+H)

where the mass was observed as 549.03; the expected mass is 548. LC/MS indicated a purity of 100% as measured by UV 214 nM.

Example 17

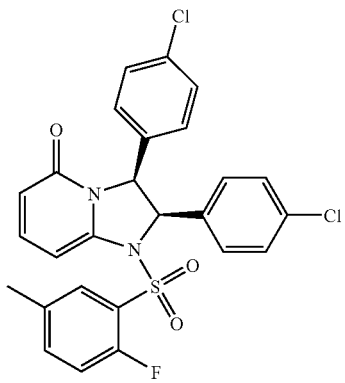

rac-cis-2,3-Bis-(4-chloro-phenyl)-1-(2-fluoro-5-methyl-benzenesulfonyl)-2,3-dihydro-1H-imidazo[1,2-a]pyridin-5-one was prepared according to general method A by reaction of rac-cis-bis-(4-chloro-phenyl)-2,3-dihydro-1H-imidazo[1,2-a]pyridin-5-one with 2-fluoro-5-methylbenzenesulfonyl chloride. The compound was isolated by preparative HPLC. The expected product was characterized by LC/MS (M+H) where the mass was observed as 529.07, the expected mass is 528. LC/MS indicated a purity of 100% as measured by UV 214 nM.

Example 18

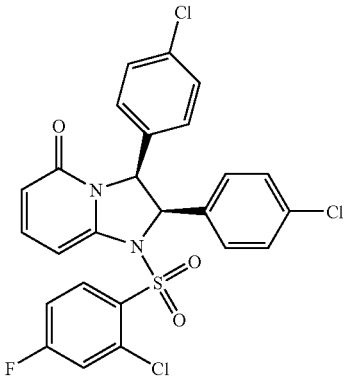

rac-1-(2-Chloro-4-fluoro-benzenesulfonyl)-cis-2,3-bis-(4-chloro-phenyl)-2,3-dihydro-1H-imidazo[1,2-a]pyridin-5-one was prepared according to general method A by reaction of rac-bis-(4-chloro-phenyl)-2,3-dihydro-1H-imidazo[1,2-a]pyridin-5-one with 2-chloro-4-fluorobnezenesulfonyl chloride. The compound was isolated by preparative HPLC. The expected product was characterized by LC/MS (M+H) where the mass was observed as 549.04; the expected mass is 548. LC/MS indicated a purity of 100% as measured by UV 214 nM.

Example 19

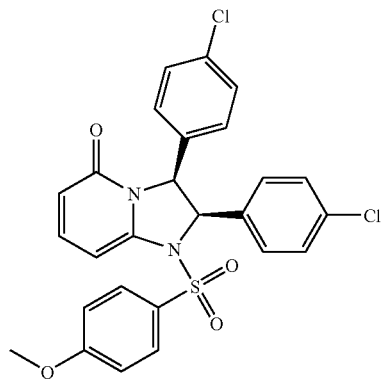

rac-cis-2,3-Bis-(4-chloro-phenyl)-1-(4-methoxy-benzenesulfonyl)-2,3-dihydro-1H-imidazo[1,2-a]pyridin-5-one was prepared according to general method A by reaction of rac-cis-bis-(4-chloro-phenyl)-2,3-dihydro-1H-imidazo[1,2-a]pyridin-5-one with 4-methoxybenzenesulfonyl chloride. The compound was isolated by preparative HPLC. The expected product was characterized by LC/MS (M+H) where the mass was observed as 527.14; the expected mass is 526.1. LC/MS indicated a purity of 94.09% as measured by UV 214 nM.

Example 20

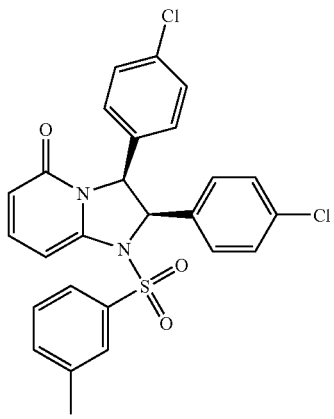

rac-cis-2,3-Bis-(4-chloro-phenyl)-1-(toluene-3-sulfonyl)-2,3-dihydro-1H-imidazo[1,2-a]pyridin-5-one was prepared according to general method A by reaction of rac-cis-bis-(4-chloro-phenyl)-2,3-dihydro-1H-imidazo[1,2-a]pyridin-5-one with m-toluenesulfonyl chloride. The compound was isolated by preparative HPLC. The expected product was characterized by LC/MS (M+H) where the mass was observed as 511.08; the expected mass is 510.1. LC/MS indicated a purity of 100% as measured by UV 214 nM.

Example 21

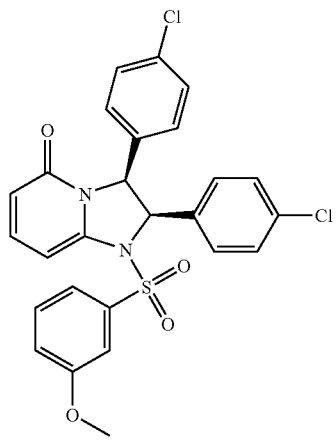

rac-cis-2,3-Bis-(4-chloro-phenyl)-1-(3-methoxy-benzenesulfonyl)-2,3-dihydro-1H-imidazo[1,2-a]pyridin-5-one was prepared according to general method A by reaction of rac-cis-bis-(4-chloro-phenyl)-2,3-dihydro-1H-imidazo[1,2-a]pyridin-5-one with 3-methoxybenzenesulfonyl chloride. The compound was isolated by preparative HPLC. The expected product was characterized by LC/MS (M+H) where the mass was observed as 527.07; the expected mass is 526.1 LC/MS indicated a purity of 100% as measured by UV 214 nM.

Example 22

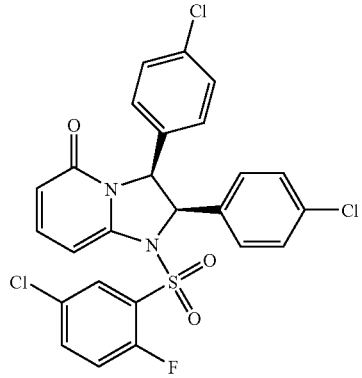

rac-cis-1-(5-Chloro-2-fluoro-benzenesulfonyl)-2,3-bis-(4-chloro-phenyl)-2,3-dihydro-1H-imidazo[1,2-a]pyridin-5-one was prepared according to general method A by reaction of rac-cis-bis-(4-chloro-phenyl)-2,3-dihydro-1H-imidazo[1,2-a]pyridin-5-one with 5-chloro-2-fluorobenzenesulfonyl chloride. The compound was isolated by preparative HPLC. The expected product was characterized by LC/MS (M+H) where the mass was observed as 549.06; the expected mass is 548. LC/MS indicated a purity of 100% as measured by UV 214 nM.

Example 23

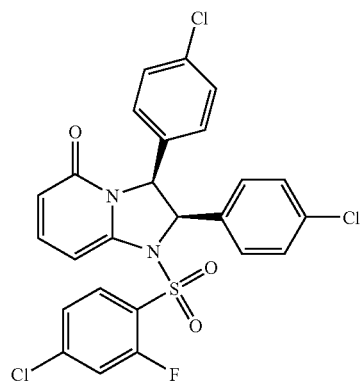

rac-cis-1-(4-Chloro-2-fluoro-benzenesulfonyl)-2,3-bis-(4-chloro-phenyl)-2,3-dihydro-1H-imidazo[1,2-a]pyridin-5-one was prepared according to general method A by reaction of rac-cis-bis-(4-chloro-phenyl)-2,3-dihydro-1H-imidazo[1,2-a]pyridin-5-one with 4-chloro-2-fluorobenzenesulfonyl chloride. The compound was isolated by preparative HPLC. The expected product was characterized by LC/MS (M+H) where the mass was observed as 549.04; the expected mass is 548. LC/MS indicated a purity of 100% as measured by UV 214 nM.

Example 24

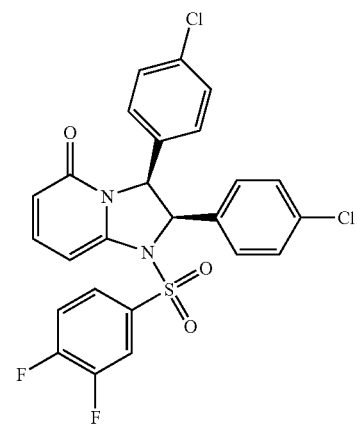

rac-cis-2,3-Bis-(4-chloro-phenyl)-1-(3,4-difluoro-benzenesulfonyl)-2,3-dihydro-1H-imidazo[1,2-a]pyridin-5-one was prepared according to general method A by reaction of rac-cis-bis-(4-chloro-phenyl)-2,3-dihydro-1H-imidazo[1,2-a]pyridin-5-one with 3,4-difluorobenzenesulfonyl chloride. The compound was isolated by preparative HPLC. The expected product was characterized by LC/MS (M+H) where the mass was observed as 533.05; the expected mass is 532. LC/MS indicated a purity of 94.77% as measured by UV 214 nM.

Example 25

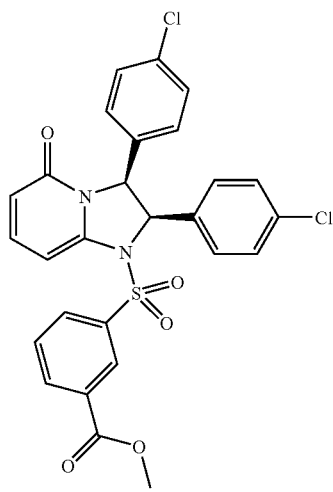

rac-3-[cis-2,3-Bis-(4-chloro-phenyl)-5-oxo-2,3-dihydro-5H-imidazo[1,2-a]pyridine-1-sulfonyl]-benzoic acid methyl ester was prepared according to general method A by reaction of rac-cis-bis-(4-chloro-phenyl)-2,3-dihydro-1H-imidazo[1,2-a]pyridin-5-one with 3-chlorosulfonyl-benzoic acid methyl ester. The compound was isolated by preparative HPLC. The expected product was characterized by LC/MS (M+H) where the mass was observed as 554.9; the expected mass is 554. LC/MS indicated a purity of 91.42% as measured by UV 214 nM.

Example 26

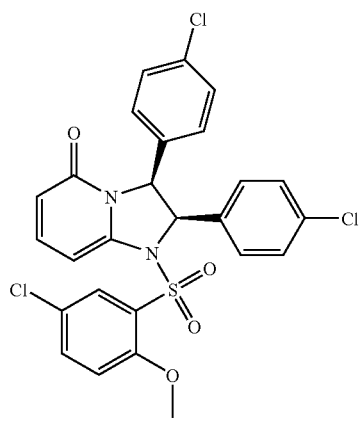

rac-cis-1-(5-Chloro-2-methoxy-benzenesulfonyl)-2,3-bis-(4-chloro-phenyl)-2,3-dihydro-1H-imidazo[1,2-a]pyridin-5-one was prepared according to general method A by reaction of rac-cis-bis-(4-chloro-phenyl)-2,3-dihydro-1H-imidazo[1,2-a]pyridin-5-one with 5-chloro-2-methoxybenzenesulfonyl chloride. The compound was isolated by preparative HPLC. The expected product was characterized by LC/MS (M+H) where the mass was observed as 561.04; the expected mass is 560. LC/MS indicated a purity of 100% as measured by UV 214 nM.

Example 27

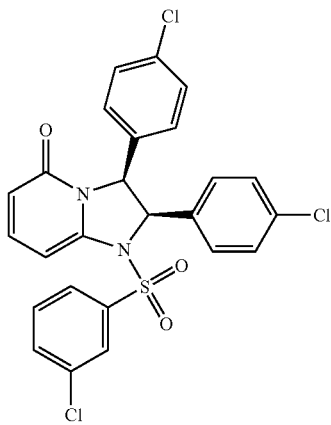

rac-cis-1-(3-Chloro-benzenesulfonyl)-2,3-bis-(4-chloro-phenyl)-2,3-dihydro-1H-imidazo[1,2-a]pyridin-5-one was prepared according to general method A by reaction of rac-cis-bis-(4-chloro-phenyl)-2,3-dihydro-1H-imidazo[1,2-a]pyridin-5-one with 3-chlorobenzenesulfonyl chloride. The compound was isolated by preparative HPLC. The expected product was characterized by LC/MS (M+H) where the mass was observed as 531.05, the expected mass is 530. LC/MS indicated a purity of 89.59% as measured by UV 214 nM.

Example 28

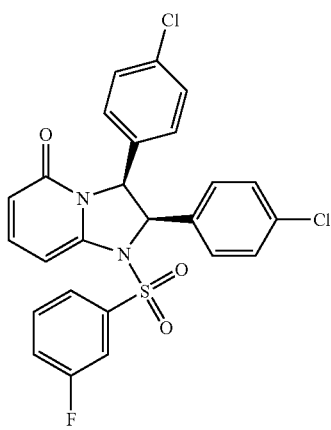

rac-cis-2,3-Bis-(4-chloro-phenyl)-1-(3-fluoro-benzenesulfonyl)-2,3-dihydro-1H-imidazo[1,2-a]pyridin-5-one was prepared according to general method A by reaction of rac-cis-bis-(4-chloro-phenyl)-2,3-dihydro-1H-imidazo[1,2-a]pyridin-5-one with 3-fluorobenzenesulfonyl chloride. The compound was isolated by preparative HPLC. The expected product was characterized by LC/MS (M+H) where the mass was observed as 515.12; the expected mass is 514. LC/MS indicated a purity of 50.76% as measured by UV 214 nM.

Example 29

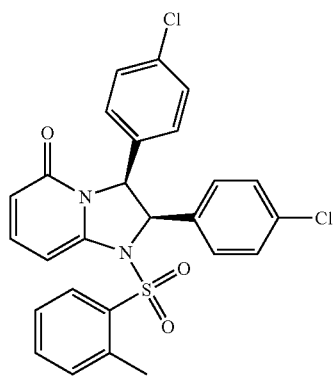

rac-cis-2,3-Bis-(4-chloro-phenyl)-1-(toluene-2-sulfonyl)-2,3-dihydro-1H-imidazo[1,2-a]pyridin-5-one was prepared according to general method A by reaction of rac-cis-bis-(4-chloro-phenyl)-2,3-dihydro-1H-imidazo[1,2-a]pyridin-5-one with o-toluensulfonyl chloride. The compound was isolated by preparative HPLC. The expected product was characterized by LC/MS (M+H) where the mass was observed as 511.07; the expected mass is 510.1. LC/MS indicated a purity of 100% as measured by UV 214 nM.

Example 30

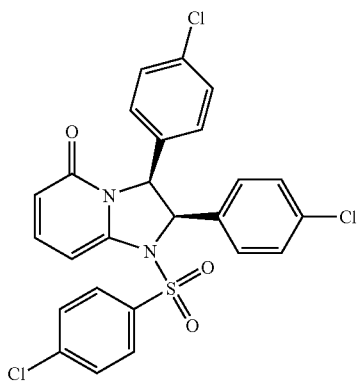

rac-cis-1-(4-Chloro-benzenesulfonyl)-2,3-bis-(4-chloro-phenyl)-2,3-dihydro-1H-imidazo[1,2-a]pyridin-5-one was prepared according to general method A by reaction of rac-cis-bis-(4-chloro-phenyl)-2,3-dihydro-1H-imidazo[1,2-a]pyridin-5-one with 4-chlorobenzenesulfonyl chloride. The compound was isolated by preparative HPLC. The expected product was characterized by LC/MS (M+H) where the mass was observed as 531.05; the expected mass is 530. LC/MS indicated a purity of 74.86% as measured by UV 214 nM.

Example 31

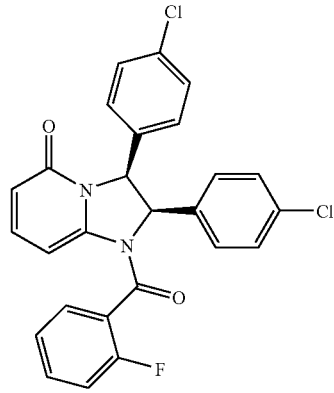

rac-cis-2,3-Bis-(4-chloro-phenyl)-1-(2-fluoro-benzoyl)-2,3-dihydro-1H-imidazo[1,2-a]pyridin-5-one was prepared according to general method A by reaction of rac-cis-bis-(4-chloro-phenyl)-2,3-dihydro-1H-imidazo[1,2-a]pyridin-5-one with 2-fluorobenzoyl chloride. The compound was isolated by preparative HPLC. The expected product was characterized by LC/MS (M+H) where the mass was observed as 479.18; the expected mass is 478.1. LC/MS indicated a purity of 100% as measured by UV 214 nM.

Example 32

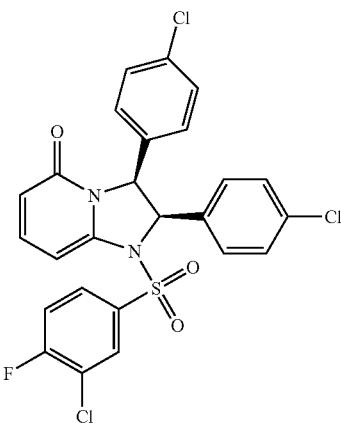

rac-cis-1-(3-Chloro-4-fluoro-benzenesulfonyl)-2,3-bis-(4-chloro-phenyl)-2,3-dihydro-1H-imidazo[1,2-a]pyridin-5-one was prepared according to general method A by reaction of rac-cis-bis-(4-chloro-phenyl)-2,3-dihydro-1H-imidazo[1,2-a]pyridin-5-one with 3-chloro-4-fluorobenzenesulfonyl chloride. The compound was isolated by preparative HPLC. The expected product was characterized by LC/MS (M+H)

where the mass was observed as 549.05; the expected mass is 548. LC/MS indicated a purity of 93.31% as measured by UV 214 nM.

Example 33

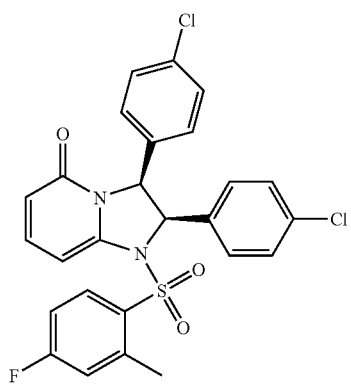

rac-cis-2,3-Bis-(4-chloro-phenyl)-1-(4-fluoro-2-methyl-benzenesulfonyl)-2,3-dihydro-1H-imidazo[1,2-a]pyridin-5-one was prepared according to general method A by reaction of rac-cis-bis-(4-chloro-phenyl)-2,3-dihydro-1H-imidazo[1,2-a]pyridin-5-one with 4-fluoro-2-methylbenzenesulfonyl chloride. The compound was isolated by preparative HPLC. The expected product was characterized by LC/MS (M+H) where the mass was observed as 529.06; the expected mass is 528. LC/MS indicated a purity of 100% as measured by UV 214 nM.

Example 34

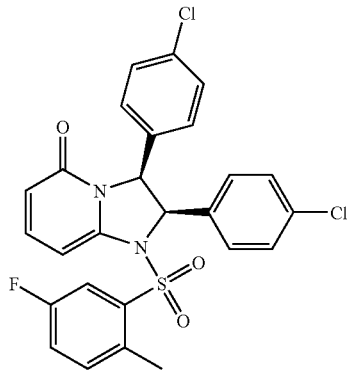

rac-cis-2,3-Bis-(4-chloro-phenyl)-1-(5-fluoro-2-methyl-benzenesulfonyl)-2,3-dihydro-1H-imidazo[1,2-a]pyridin-5-one was prepared according to general method A by reaction of rac-cis-bis-(4-chloro-phenyl)-2,3-dihydro-1H-imidazo[1,2-a]pyridin-5-one with 5-fluoro-2-methylbenzenesulfonyl chloride. The compound was isolated by preparative HPLC. The expected product was characterized by LC/MS (M+H) where the mass was observed as 529.06; the expected mass is 528. LC/MS indicated a purity of 100% as measured by UV 214 nM.

Example 36

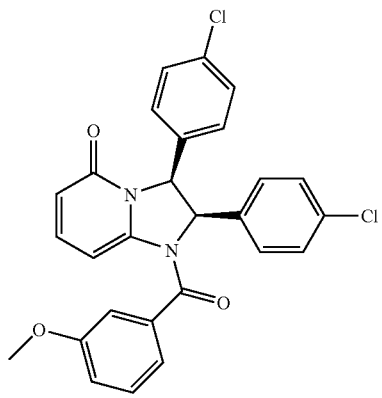

rac-cis-2,3-Bis-(4-chloro-phenyl)-1-(3-methoxy-benzoyl)-2,3-dihydro-1H-imidazo[1,2-a]pyridin-5-one was prepared according to general method A by reaction of rac-cis-bis-(4-chloro-phenyl)-2,3-dihydro-1H-imidazo[1,2-a]pyridin-5-one with 3-methoxybenzoyl chloride. The compound was isolated by preparative HPLC. The expected product was characterized by LC/MS (M+H) where the mass was observed as 491.21; the expected mass is 490.1. LC/MS indicated a purity of 100% as measured by UV 214 nM.

Example 36

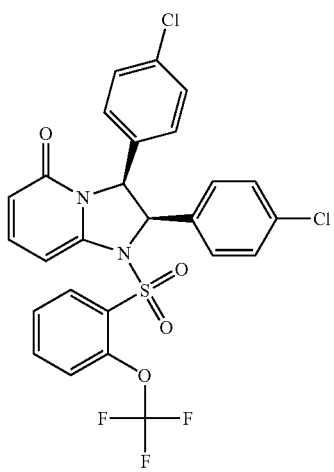

rac-cis-2,3-Bis-(4-chloro-phenyl)-1-(2-trifluoromethoxy-benzenesulfonyl)-2,3-dihydro-1H-imidazo[1,2-a]pyridin-5-one was prepared according to general method A by reaction of rac-cis-bis-(4-chloro-phenyl)-2,3-dihydro-1H-imidazo[1,2-a]pyridin-5-one with 2-(trifluoromethoxy)benzenesulfonyl chloride. The compound was isolated by preparative HPLC. The expected product was characterized by LC/MS (M+H)

where the mass was observed as 581; the expected mass is 580. LC/MS indicated a purity of 100% as measured by UV 214 nM.

Example 37

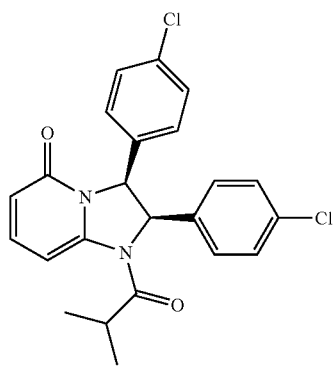

rac-cis-2,3-Bis-(4-chloro-phenyl)-1-isobutyryl-2,3-dihydro-1H-imidazo[1,2-a]pyridin-5-one was prepared according to general method A by reaction of rac-cis-bis-(4-chlorophenyl)-2,3-dihydro-1H-imidazo[1,2-a]pyridin-5-one with isobutyryl chloride. The compound was isolated by preparative HPLC. The expected product was characterized by LC/MS (M+H) where the mass was observed as 427.2. the expected mass is 426.1. LC/MS indicated a purity of 100% as measured by UV 214 nM.

Example 38

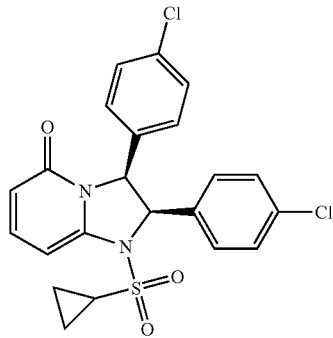

rac-cis-2,3-Bis-(4-chloro-phenyl)-1-cyclopropanesulfonyl-2,3-dihydro-1H-imidazo[1,2-a]pyridin-5-one was prepared according to general method A by reaction of rac-cis-bis-(4-chloro-phenyl)-2,3-dihydro-1H-imidazo[1,2-a]pyridin-5-one with cyclopropanesulfonyl chloride The compound was isolated by preparative HPLC. The expected product was characterized by LC/MS (M+H) where the mass was observed as 461.16; the expected mass is 460. LC/MS indicated a purity of 100% as measured by UV 214 nM.

Example 39

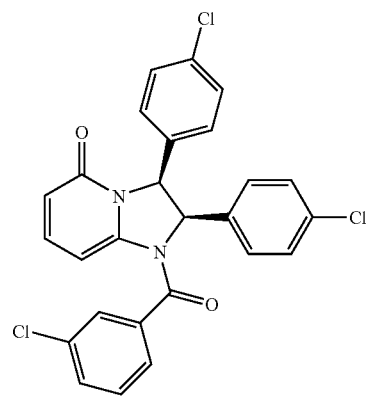

rac-cis-1-(3-Chloro-benzoyl)-2,3-bis-(4-chloro-phenyl)-2,3-dihydro-1H-imidazo[1,2-a]pyridin-5-one was prepared according to general method A by reaction of rac-cis-bis-(4-chloro-phenyl)-2,3-dihydro-1H-imidazo[1,2-a]pyridin-5-one with 3-chlorobenzoyl chloride. The compound was isolated by preparative HPLC. The expected product was characterized by LC/MS (M+H) where the mass was observed as 495.11; the expected mass is 494. LC/MS indicated a purity of 100% as measured by UV 214 nM.

Example 40

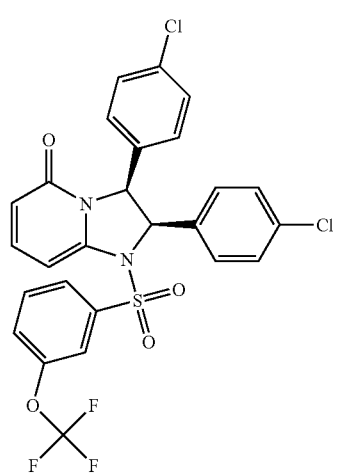

rac-cis-2,3-Bis-(4-chloro-phenyl)-1-(3-trifluoromethoxy-benzenesulfonyl)-2,3-dihydro-1H-imidazo[1,2-a]pyridin-5-one was prepared according to general method A by reaction of rac-cis-bis-(4-chloro-phenyl)-2,3-dihydro-1H-imidazo[1, 2-a]pyridin-5-one with 3-(trifluoromethoxy)benzenesulfonyl chloride. The compound was isolated by preparative HPLC. The expected product was characterized by LC/MS (M+H)

where the mass was observed as 581.01; the expected mass is 580. LC/MS indicated a purity of 100% as measured by UV 214 nM.

Example 41

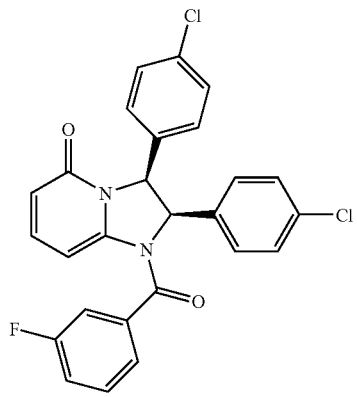

rac-cis-2,3-Bis-(4-chloro-phenyl)-1-(3-fluoro-benzoyl)-2,3-dihydro-1H-imidazo[1,2-a]pyridin-5-one was prepared according to general method A by reaction of rac-cis-bis-(4-chloro-phenyl)-2,3-dihydro-1H-imidazo[1,2-a]pyridin-5-one with 3-fluorobenzoyl chloride. The compound was isolated by preparative HPLC. The expected product was characterized by LC/MS (M+H) where the mass was observed as 479.19; the expected mass is 478.1. LC/MS indicated a purity of 100% as measured by UV 214 nM.

Example 42

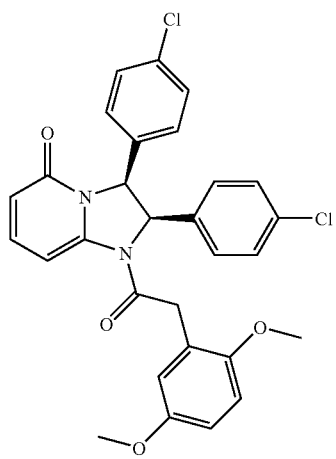

rac-cis-2,3-Bis-(4-chloro-phenyl)-1-[2-(2,5-dimethoxy-phenyl)-acetyl]-2,3-dihydro-1H-imidazo[1,2-a]pyridin-5-one was prepared according to general method A by reaction of rac-cis-bis-(4-chloro-phenyl)-2,3-dihydro-1H-imidazo[1, 2-a]pyridin-5-one with (2,5-dimethoxypenyl)acetyl chloride. The compound was isolated by preparative HPLC. The expected product was characterized by LC/MS (M+H) where the mass was observed as 535.21 the expected mass is 534.1. LC/MS indicated a purity of 100% as measured by UV 214 nM.

Example 43

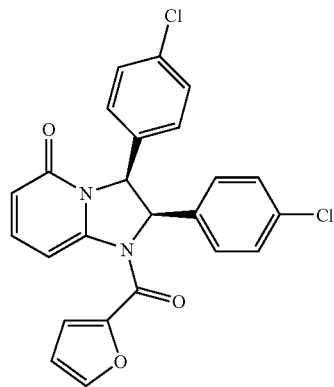

rac-cis-2,3-Bis-(4-chloro-phenyl)-1-(furan-2-carbonyl)-2,3-dihydro-1H-imidazo[1,2-a]pyridin-5-one was prepared according to general method A by reaction of rac-cis-bis-(4-chloro-phenyl)-2,3-dihydro-1H-imidazo[1,2-a]pyridin-5-one with 2-furoyl chloride. The compound was isolated by preparative HPLC. The expected product was characterized by LC/MS (M+H) where the mass was observed as 451.17; the expected mass is 450.1. LC/MS indicated a purity of 100% as measured by UV 214 nM.

Example 44

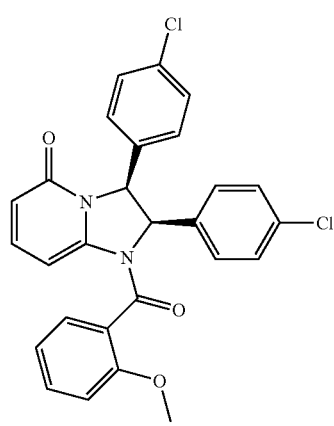

rac-cis-2,3-Bis-(4-chloro-phenyl)-1-(2-methoxy-benzoyl)-2,3-dihydro-1H-imidazo[1,2-a]pyridin-5-one was prepared according to general method A by reaction of rac-cis-bis-(4-chloro-phenyl)-2,3-dihydro-1H-imidazo[1,2-a]pyridin-5-one with 2-methoxybenzoyl chloride. The compound was isolated by preparative HPLC. The expected product was characterized by LC/MS (M+H) where the mass was observed as 491.17; the expected mass is 490.1. LC/MS indicated a purity of 100% as measured by UV 214 nM.

Example 45

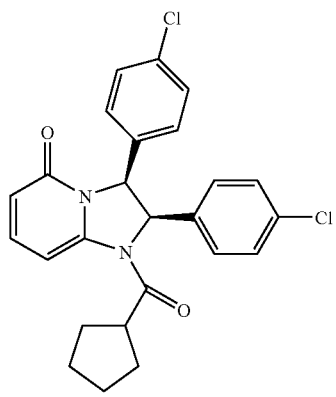

rac-cis-2,3-Bis-(4-chloro-phenyl)-1-cyclopentanecarbonyl-2,3-dihydro-1H-imidazo[1,2-a]pyridin-5-one was prepared according to general method A by reaction of rac-cis-bis-(4-chloro-phenyl)-2,3-dihydro-1H-imidazo[1,2-a]pyridin-5-one with cyclopentanecarbonyl chloride. The compound was isolated by preparative HPLC. The expected product was characterized by LC/MS (M+H) where the mass was observed as 453.23, the expected mass is 452.1. LC/MS indicated a purity of 100% as measured by UV 214 nM.

Example 46

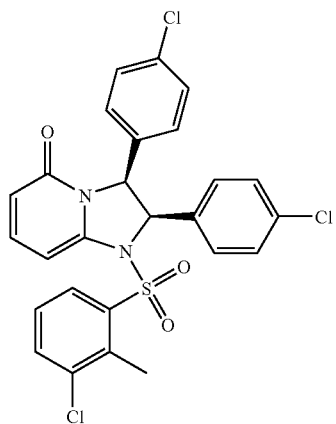

rac-cis-1-(3-Chloro-2-methyl-benzenesulfonyl)-2,3-bis-(4-chloro-phenyl)-2,3-dihydro-1H-imidazo[1,2-a]pyridin-5-one was prepared according to general method A by reaction of rac-cis-bis-(4-chloro-phenyl)-2,3-dihydro-1H-imidazo[1,2-a]pyridin-5-one with 3-chloro-2-methylbenzenesulfonyl chloride. The compound was isolated by preparative HPLC. The expected product was characterized by LC/MS (M+H) where the mass was observed as 545.04; the expected mass is 544. LC/MS indicated a purity of 100% as measured by UV 214 nM.

Example 47

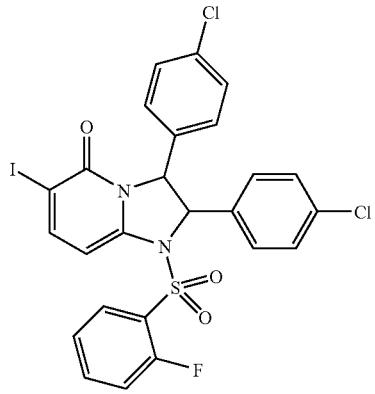

rac-cis-2,3-Bis-(4-chloro-phenyl)-1-(2-fluoro-benzenesulfonyl)-2,3-dihydro-6-iodo-1H-imidazo[1,2-a]pyridin-5-one Method B: To a solution of rac-cis-2,3-Bis-(4-chloro-phenyl)-1-(2-fluoro-benzenesulfonyl)-2,3-dihydro-1H-imidazo[1,2-a]pyridin-5-one (Example 8) (569 mg, 1.1 mmol) in MeOH (10 mL) and DCM (10 mL), N-iodosuccinimide (NIS) (373 mg, 1.7 mmol) was added and stirred at rt for 4 hrs.

The solvent was removed under reduced pressure, the residue was triturated with 50% EtOAc/Hexane, filtered, and the residue was washed twice with hexane. Dried on vacuum for 4 hrs. (504 mg, 71% yield).

$^1$H NMR (CDCL$_3$): δ 7.95 (d, 1H), 7.73-7.67 (m, 2H), 7.31-7.23 (m, 2H), 7.07 (d, 2H), 7.02 (d, 2H), 6.79 (d, 2H). 6.58 (m, 2H), 6.33 (d, 1H), 5.86 (d, 1H), 5.75 (d, 1H).

Example 48 rac-3-[cis-2,3-Bis-(4-chloro-phenyl)-5-oxo-2,3-dihydro-6-iodo-5H-imidazo[1,2-a]pyridine-1-sulfonyl]-benzonitrile

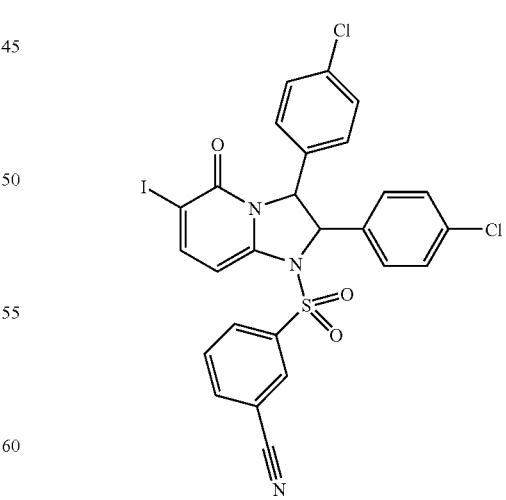

The titled compound was prepared according to general method B by reaction of rac-3-[cis-2,3-Bis-(4-chloro-phenyl)-5-oxo-2,3-dihydro-5H-imidazo[1,2-a]pyridine-1-sulfonyl]-benzonitrile with NIS.

¹H NMR (CDCL3): δ 8.07 (d, 1H), 8.00-7.92 (m 3H), 7.71 (dd, 1H), 7.10-7.05 (m, 4H), 6.81 (m, 2H), 6.59 (d, 1H), 6.52 (m, 2H), 5.72 (d, 1H), 5.27 (d, 1H).

Example 49 rac-3-[cis-2,3-Bis-(4-chloro-phenyl)-5-oxo-2,3-dihydro-6-iodo-5H-imidazo[1,2-a]pyridine-1-sulfonyl]-benzoic acid methyl ester

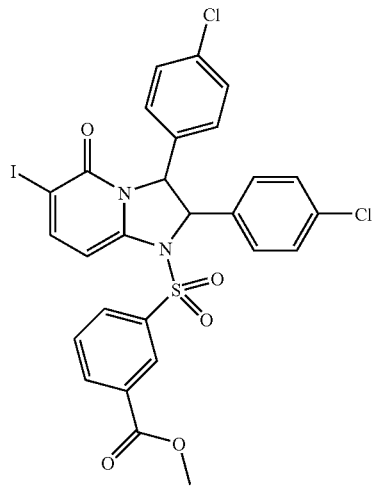

The titled compound was prepared according to general method B by reaction of rac-3-[cis-2,3-bis-(4-chloro-phenyl)-5-oxo-2,3-dihydro-5H-imidazo[1,2-a]pyridine-1-sulfonyl]-benzoic acid methyl ester with NIS.

¹H NMR (CDCl₃): δ 8.36-8.32 (m, 2H), 8.04 (d, 1H), 7.91 (m, 1H), 7.65 (dd, 1H), 7.05 (m, 4H), 6.81 (d, 2H), 6.63 (d, 1H), 6.50 (d, 2H), 5.67 (d, 1H), 5.24 (d, 1H), 3.98 (s, 3H).

Method C: To a solution of Iodide (0.094 mmol, 1 equiv.) in THF (2 mL) in a sealable tube, Pd(PPh₃)₄ (0.028 mmol, 0.3 equiv.) was added, followed by DIPEA (1.4 mmol, 15 equiv.) and amine (0.468 mmol, 5 equiv.). The reaction tube was charged with 50 psi carbon monoxide, and heated at 65° C. for one hour.

The solvent was removed under reduced pressure. Preparative HPLC provided the title compounds.

Example 50

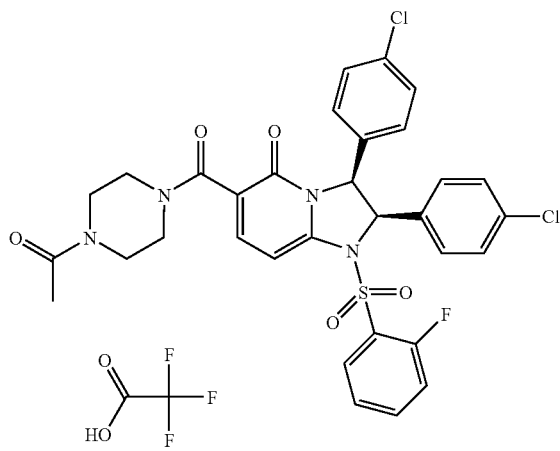

rac-cis-6-(4-Acetyl-piperazine-1-carbonyl)-2,3-bis-(4-chloro-phenyl)-1-(2-fluoro-benzenesulfonyl)-2,3-dihydro-1H-imidazo[1,2-a]pyridin-5-one one was prepared according to general method C by reaction of rac-cis-2,3-bis-(4-chloro-phenyl)-1-(2-fluoro-benzenesulfonyl)-6-iodo-2,3-dihydro-1H-imidazo[1,2-a]pyridin-5-one with N-acetyl-piperazine. The compound was isolated by preparative HPLC. The expected product was characterized by LC/MS (M+H) where the mass was observed as 669.13; the expected mass is 668. LC/MS indicated a purity of 100% as measured by UV 214 nM.

Example 51

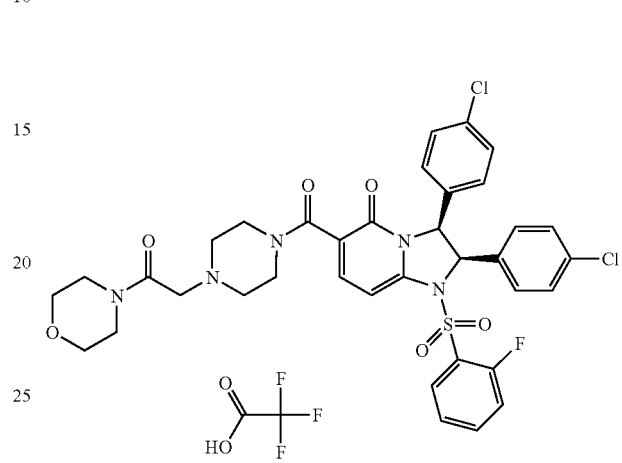

rac-cis-2,3-Bis-(4-chloro-phenyl)-1-(2-fluoro-benzenesulfonyl)-6-[4-(2-morpholin-4-yl-2-oxo-ethyl)-piperazine-1-carbonyl]-2,3-dihydro-1H-imidazo[1,2-a]pyridin-5-one was prepared according to general method C by reaction of rac-cis-2,3-bis-(4-chloro-phenyl)-1-(2-fluoro-benzenesulfonyl)-6-iodo-2,3-dihydro-1H-imidazo[1,2-a]pyridin-5-one with 4-[2-(piperzin-1-yl)-acetyl]morpholine. The compound was isolated by preparative HPLC. The expected product was characterized by LC/MS (M+H) where the mass was observed as 754.3; the expected mass is 753. LC/MS indicated a purity of 100% as measured by UV 214 nM.

Example 52

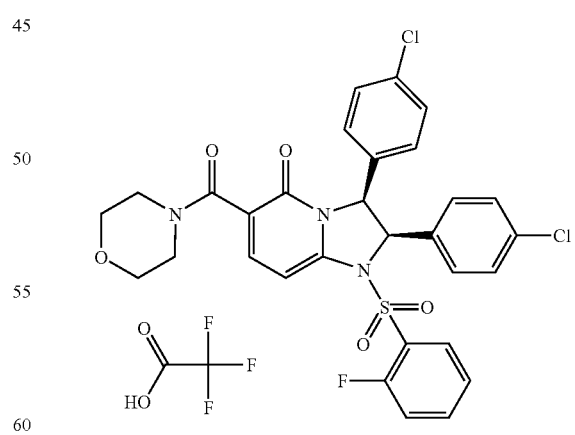

rac-cis-2,3-Bis-(4-chloro-phenyl)-1-(2-fluoro-benzenesulfonyl)-6-(morpholine-4-carbonyl)-2,3-dihydro-1H-imidazo[1,2-a]pyridin-5-one was prepared according to general method C by reaction of rac-cis-2,3-Bis-(4-chloro-phenyl)-1-(2-fluoro-benzenesulfonyl)-6-iodo-2,3-dihydro-1H-imidazo[1,2-a]pyridin-5-one with morpholine. The compound was isolated by preparative HPLC. The expected product was characterized by LC/MS (M+H) where the mass was observed as 627.86; the expected mass is 627. LC/MS indicated a purity of 89% as measured by UV 214 nM.

Example 53

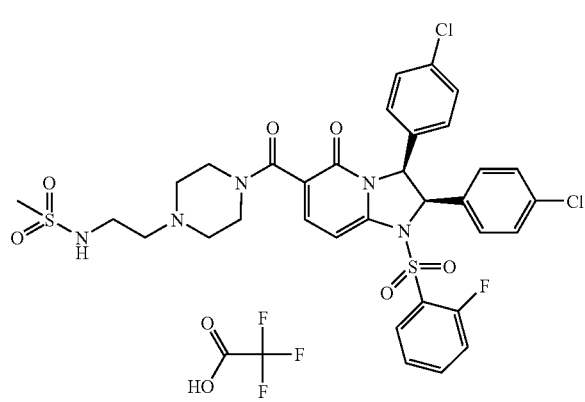

N-(2-{4-[rac-cis-2,3-Bis-(4-chloro-phenyl)-1-(2-fluoro-benzenesulfonyl)-5-oxo-1,2,3,5-tetrahydro-imidazo[1,2-a]pyridine-6-carbonyl]-piperazin-1-yl}-ethyl)-methane-sulfonamide was prepared according to general method C by reaction of rac-cis-2,3-Bis-(4-chloro-phenyl)-1-(2-fluoro-benzenesulfonyl)-6-iodo-2,3-dihydro-1H-imidazo[1,2-a]pyridin-5-one with N-(2-Piperazin-1-yl-ethyl)-methanesulfonamide. The compound was isolated by preparative HPLC The expected product was characterized by LC/MS (M+H) where the mass was observed as 748.2; the expected mass is 747. LC/MS indicated a purity of 100% as measured by UV 214 nM.

Example 54

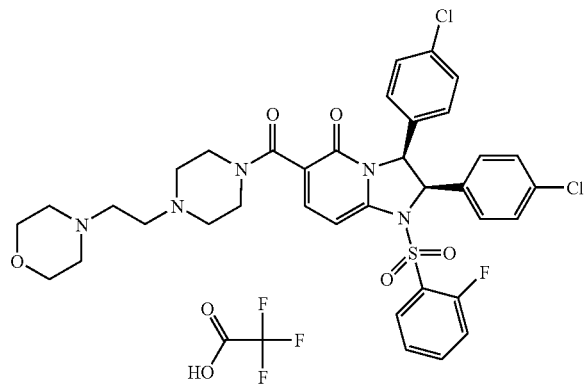

rac-cis-2,3-Bis-(4-chloro-phenyl)-1-(2-fluoro-benzenesulfonyl)-6-[4-(2-morpholin-4-yl-ethyl)-piperazine-1-carbonyl]-2,3-dihydro-1H-imidazo[1,2-a]pyridin-5-one was prepared according to general method C by reaction of rac-cis-2,3Bis-(4-chloro-phenyl)-1-(2-fluoro-benzenesulfonyl)-6-iodo-2,3-dihydro-1H-imidazo[1,2-a]pyridin-5-one with 1-[2-(morpholine-4-yl)-ethyl]-piperazine. The compound was isolated by preparative HPLC. The expected product was characterized by LC/MS (M+H) where the mass was observed as 740.3; the expected mass is 739. LC/MS indicated a purity of 100% as measured by UV 214 nM.

Example 55

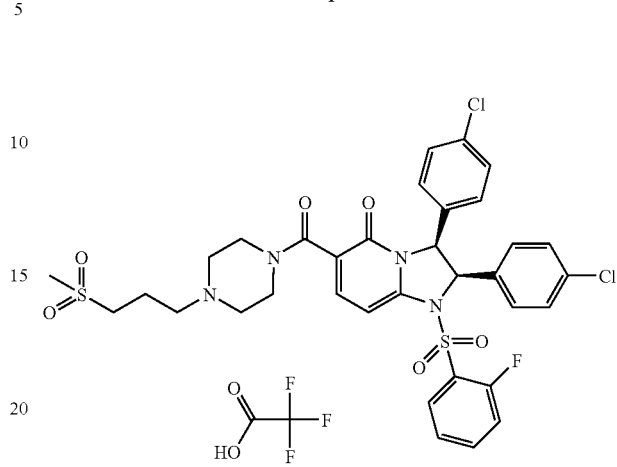

rac-cis-2,3-Bis-(4-chloro-phenyl)-1-(2-fluoro-benzenesulfonyl)-6-[4-(3-methanesulfonyl-propyl)-piperazine-1-carbonyl]-2,3-dihydro-1H-imidazo[1,2-a]pyridin-5-one was prepared according to general method C by reaction of rac-cis-2,3-bis-(4-chloro-phenyl)-1-(2-fluoro-benzenesulfonyl)-6-iodo-2,3-dihydro-1H-imidazo[1,2-a]pyridin-5-one with 1-(3-Methanesulfonyl-propyl)-piperazine. The compound was isolated by preparative HPLC. The expected product was characterized by LC/MS (M+H) where the mass was observed as 747.12; the expected mass is 746. LC/MS indicated a purity of 100% as measured by UV 214 nM.

Example 56

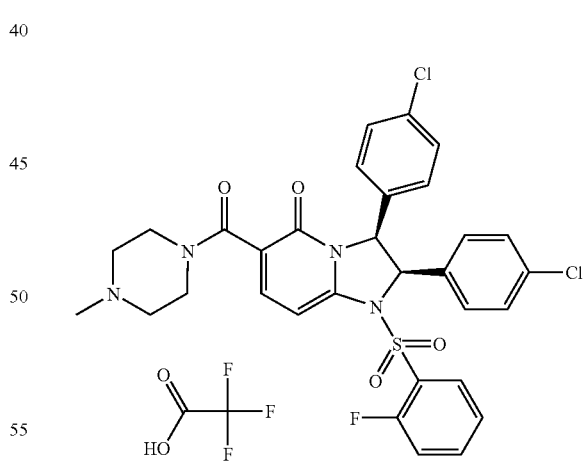

rac-cis-2,3-Bis-(4-chloro-phenyl)-1-(2-fluoro-benzenesulfonyl)-6-(4-methyl-piperazine-1-carbonyl)-2,3-dihydro-1H-imidazo[1,2-a]pyridin-5-one was prepared according to general method C by reaction of rac-cis-2,3-bis-(4-chloro-phenyl)-1-(2-fluoro-benzenesulfonyl)-6-iodo-2,3-dihydro-1H-imidazo[1,2-a]pyridin-5-one with N-methyl-piperazine. The compound was isolated by preparative HPLC. The expected product was characterized by LC/MS (M+H) where the mass was observed as 640.96; the expected mass is 640. LC/MS indicated a purity of 100% as measured by UV 214 nM.

Example 57

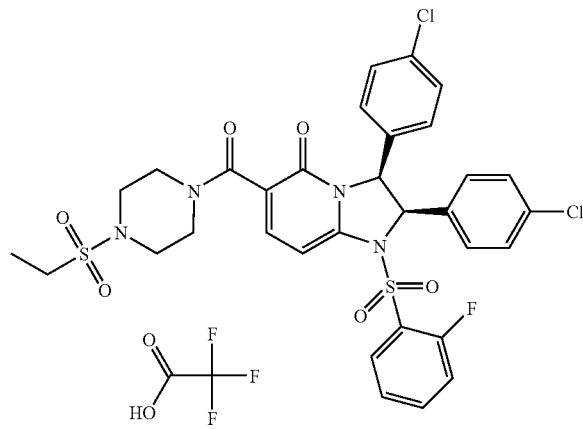

rac-cis-2,3-Bis-(4-chloro-phenyl)-6-(4-ethanesulfonyl-piperazine-1-carbonyl)-1-(2-fluoro-benzenesulfonyl)-2,3-dihydro-1H-imidazo[1,2-a]pyridin-5-one was prepared according to general method C by reaction of rac-cis-2,3-bis-(4-chloro-phenyl)-1-(2-fluoro-benzenesulfonyl)-6-iodo-2,3-dihydro-1H-imidazo[1,2-a]pyridin-5-one with 1-ethanesulfonyl-piperazine. The compound was isolated by preparative HPLC. The expected product was characterized by LC/MS (M+H) where the mass was observed as 719.18; the expected mass is 718. LC/MS indicated a purity of 88% as measured by UV 214 nM.

Example 58

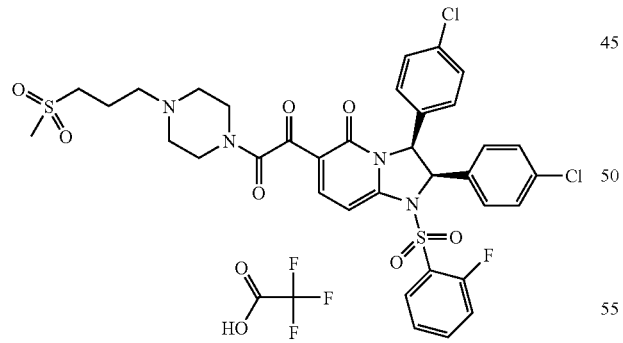

1-[rac-cis-2,3-Bis-(4-chloro-phenyl)-1-(2-fluoro-benzenesulfonyl)-5-oxo-1,2,3,5-tetrahydro-imidazo[1,2-a]pyridin-6-yl]-2-[4(3-methanesulfonyl-propyl)-piperazin1-yl]-ethane-1,2-dione was prepared according to general method C by reaction of rac-cis-2,3-bis-(4-chloro-phenyl)-1-(2-fluoro-benzenesulfonyl)-6-iodo-2,3-dihydro-1H-imidazo[1,2-a]pyridin-5-one with 1-(3-ethanesulfonyl-propyl)-piperazine, The compound was isolated by preparative HPLC. The expected product was characterized by LC/MS (M+H) where the mass was observed as 775.23; the expected mass is 774. LC/MS indicated a purity of 82% as measured by UV 214 nM.

Example 59

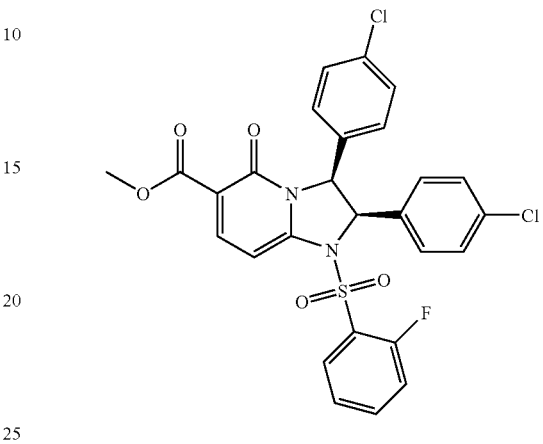

rac-cis-2,3-Bis-(4-chloro-phenyl)-1-(2-fluoro-benzenesulfonyl)-5-oxo-1,2,3,5-tetrahydro-imidazo[1,2-a]pyridine-6-carboxylic acid methyl ester was prepared according to general method C by reaction of rac-cis-2,3-bis-(4-chloro-phenyl)-1-(2-fluoro-benzenesulfonyl)-6-iodo-2,3-dihydro-1H-imidazo[1,2-a]pyridin-5-one with methanol. The compound was isolated by preparative HPLC. The expected product was characterized by LC/MS (M+H) where the mass was observed as 572.93; the expected mass is 572. LC/MS indicated a purity of 92% as measured by UV 214 nM.

Example 60

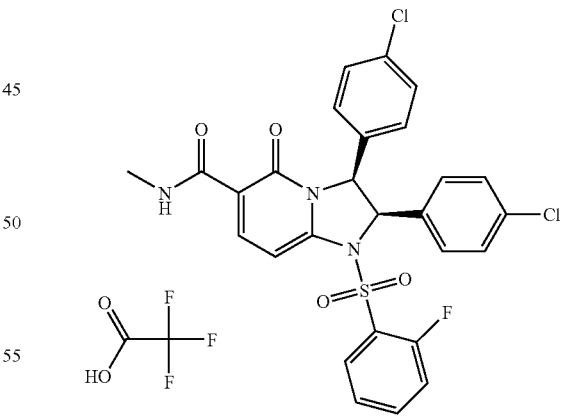

rac-cis-2,3-Bis-(4-chloro-phenyl)-1-(2-fluoro-benzenesulfonyl)-5-oxo-1,2,3,5-tetrahydro-imidazo[1,2-a]pyridine-6-carboxylic acid methylamide was prepared according to general method C by reaction of rac-cis-2,3-bis-(4-chloro-phenyl)-1-(2-fluoro-benzenesulfonyl)-6-iodo-2,3-dihydro-1H-imidazo[1,2-a]pyridin-5-one with methylamine. The compound was isolated by preparative HPLC. The expected product was characterized by LC/MS (M+H) where the mass was observed as 571.9; the expected mass is 571. LC/MS indicated a purity of 100% as measured by UV 214 nM.

Example 61

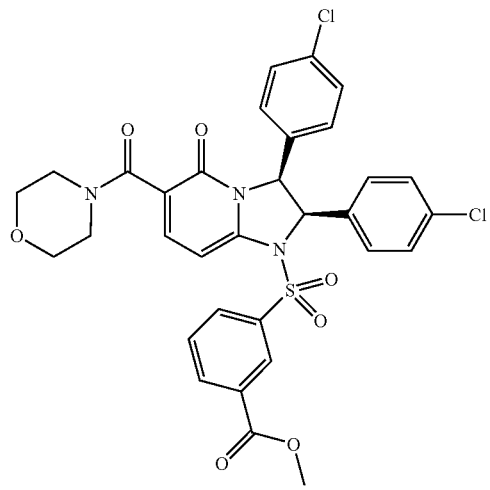

rac-3-[cis-2,3-Bis-(4-chloro-phenyl)-6-(morpholine-4-carbonyl)-5-oxo-2,3-dihydro-5H-imidazo[1,2-a]pyridine-1-sulfonyl]-benzoic acid methyl ester was prepared according to general method C by reaction of rac-3-[cis-2,3-bis-(4-chloro-phenyl)-5-oxo-2,3-dihydro-6-iodo-5H-imidazo[1,2-a]pyridine-1-sulfonyl)-benzoic acid methyl ester with morpholine. The compound was isolated by preparative HPLC. The expected product was characterized by LC/MS (M+H) where the mass was observed as 668.38; the expected mass is 667. LC/MS indicated a purity of 100% as measured by UV 214 nM.

Example 62

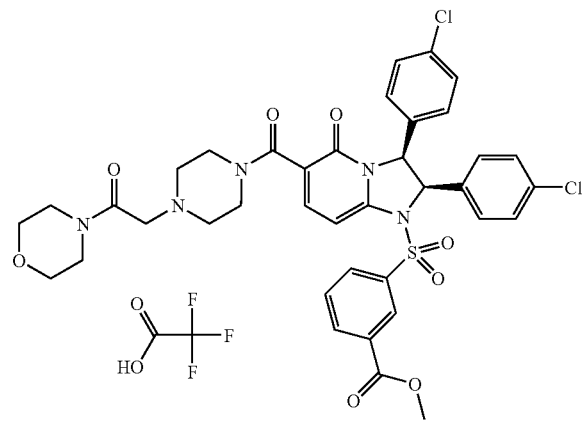

rac-3-{cis-2,3-Bis-(4-chloro-phenyl)-6-[4-(2-morpholin-4-yl-2-oxo-ethyl)-1-carbonyl]-5-oxo-2,3-dihydro-5H-imidazo[1,2-a]pyridine-1-sulfonyl}-benzoic acid methyl ester was prepared according to general method C by reaction of rac-3-[cis-2,3-Bis-(4-chloro-phenyl)-5-oxo-2,3-dihydro-6-iodo-5H-imidazo[1,2-a]pyridine-1-sulfonyl]-benzoic acid methyl ester with 1-morpholin-4-yl-2-piperazin-1-yl-ethanone. The compound was isolated by preparative HPLC. The expected product was characterized by LC/MS (M+H) where the mass was observed as 794.14; the expected mass is 793. LC/MS indicated a purity of 100% as measured by UV 214 nM.

Example 63

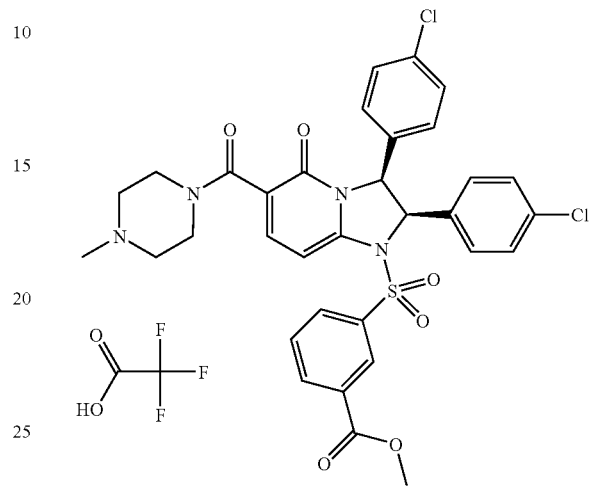

rac-3-[cis-2,3-Bis-(4-chloro-phenyl)-6-(4-methyl-piperazine-1-carbonyl)-5-oxo-2,3-dihydro-5H-imidazo[1,2-a]pyridine-1-sulfonyl]-benzoic acid methyl ester was prepared according to general method C by reaction of rac-3-[cis-2,3-bis-(4-chloro-phenyl)-5-oxo-2,3-dihydro-6-iodo-5H-imidazo[1,2-a]pyridine-1-sulfonyl]-benzoic acid methyl ester with N-methyl-piperazine. The compound was isolated by preparative HPLC. The expected product was characterized by LC/MS (M+H) where the mass was observed as 681.02; the expected mass is 680. LC/MS indicated a purity of 100% as measured by UV 214 nM.

Example 64

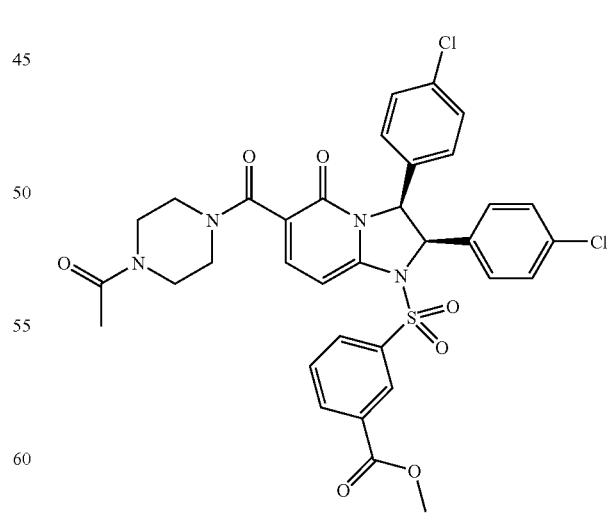

rac-3-[cis-6-(4-Acetyl-piperazine-1-carbonyl)-2,3-bis-(4-chloro-phenyl)-5-oxo-2,3-dihydro-5H-imidazo[1,2-a]pyridine-1-sulfonyl]-benzoic acid methyl ester was prepared according to general method C by reaction of rac-3-[cis-2,3- bis-(4-chloro-phenyl)-5-oxo-2,3-dihydro-6-iodo-5H-imidazo[1,2-a]pyridine-1-sulfonyl]-benzoic acid methyl ester with N-acetyl-piperazine. The compound was isolated by preparative HPLC. The expected product was characterized by LC/MS (M+H) where the mass was observed as 709.03; the expected mass is 708. LC/MS indicated a purity of 100% as measured by UV 214 nM.

Example 65

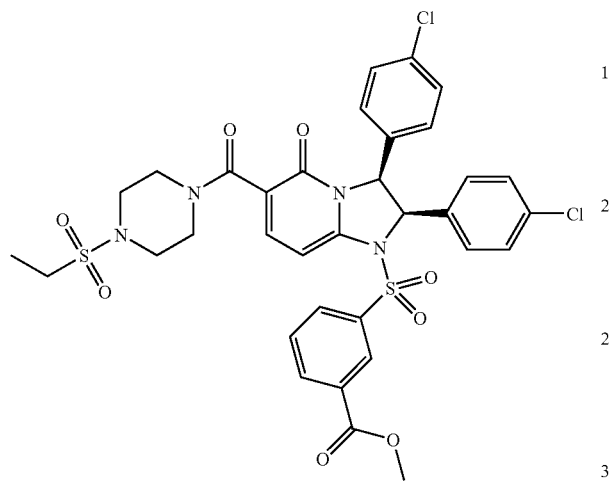

rac-3-[cis-2,3-Bis-(4-chloro-phenyl)-6-(4-ethanesulfonyl-piperazine-1-carbonyl)-5-oxo-2,3-dihydro-5H-imidazo[1,2-a]pyridine-1-sulfonyl]-benzoic acid methyl ester was prepared according to general method C by reaction of rac-3-[cis-2,3-Bis-(4-chloro-phenyl)-5-oxo-2,3-dihydro-6-iodo-5H-imidazo[1,2-a]pyridine-1-sulfonyl]-benzoic acid methyl ester with 1-Ethanesulfonyl-piperazine. The compound was isolated by preparative HPLC. The expected product was characterized by LC/MS (M+H) where the mass was observed as 759.11; the expected mass is 758. LC/MS indicated a purity of 100% as measured by UV 214 nM.

Example 66

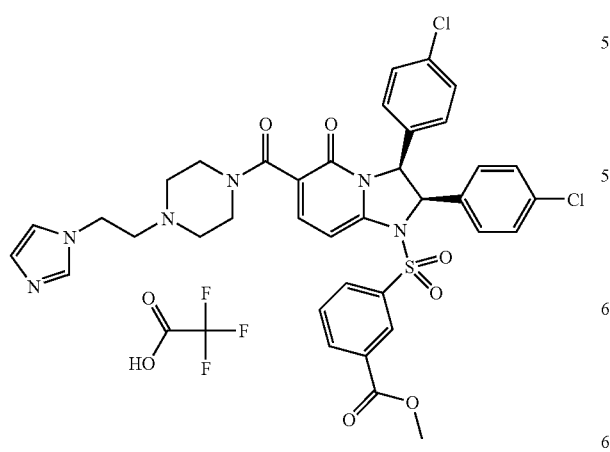

rac-3-{cis-2,3-Bis-(4-chloro-phenyl)-6-[4-(2-imidazo-1-yl-ethyl)-piperazine-1-carbonyl]-5-oxo-2,3-dihydro-5H-imidazo[1,2-a]pyridine-1-sulfonyl}-benzoic acid methyl ester was prepared according to general method C by reaction of rac-3-[cis-2,3-bis-(4-chloro-phenyl)-5-oxo-2,3-dihydro-6-iodo-5H-imidazo[1,2-a]pyridine-1-sulfonyl]-benzoic acid methyl ester with 1-(2-imidazol-1-yl-ethyl)-piperazine. The compound was isolated by preparative HPLC The expected product was characterized by LC/MS (M+H) where the mass was observed as 761.25; the expected mass is 760. LC/MS indicated a purity of 100% as measured by UV 214 nM.

Example 67

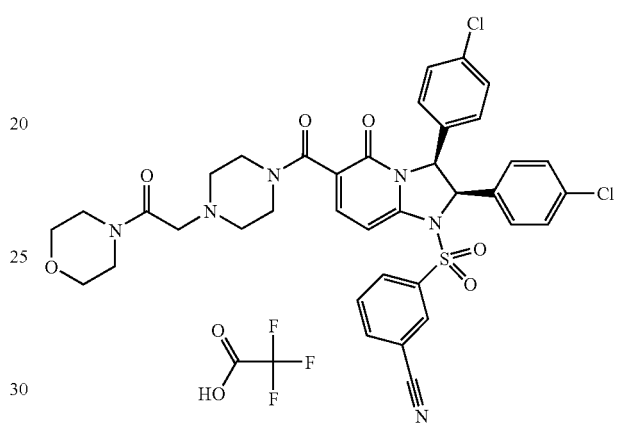

rac-3-{cis-2,3-Bis-(4-chloro-phenyl)-6-[4-(2-morpholin-4-yl-2-oxo-ethyl)-piperazin-1-ylmethyl]-5-oxo-2,3-dihydro-5H-imidazo[1,2-a]pyridine-1-sulfonyl}-benzonitrile was prepared according to general method C by reaction of rac-3-[cis-2,3-bis-(4-chloro-phenyl)-5-oxo-2,3-dihydro-6-iodo-5H-imidazo[1,2-a]pyridine-1-sulfonyl]-benzonitrile with 1-Morpholin-4-yl-2-piperazin-1-yl-ethanone. The compound was isolated by preparative HPLC. The expected product was characterized by LC/MS (M+H) where the mass was observed as 747.1; the expected mass is 746. LC/MS indicated a purity of 100% as measured by UV 214 nM.

Example 68

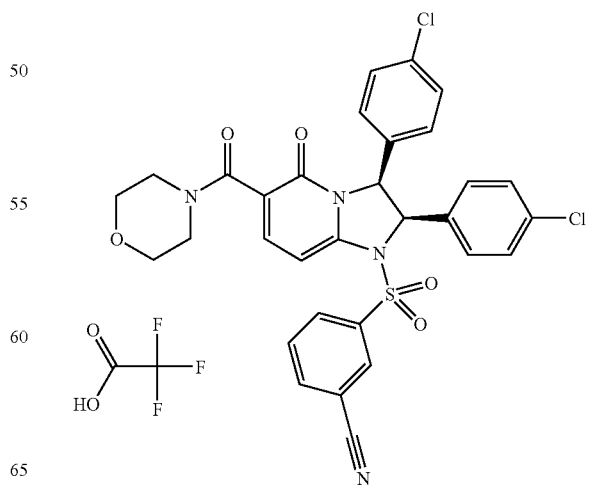

rac-3-[cis-2,3-Bis-(4-chloro-phenyl)-6-(morpholine-4-carbonyl)-5-oxo-2,3-dihydro-5H-imidazo[1,2-a]pyridine-1-sulfonyl]-benzonitrile was prepared according to general method C by reaction of rac-3-[cis-2,3-bis-(4-chloro-phenyl)-5-oxo-2,3-dihydro-6-iodo-5H-imidazo[1,2-a]pyridine-1-sulfonyl]-benzonitrile with morpholine. The compound was isolated by preparative HPLC. The expected product was characterized by LC/MS (M+H) where the mass was observed as 635.03; the expected mass is 634. LC/MS indicated a purity of 100% as measured by UV 214 nM.

Example 69

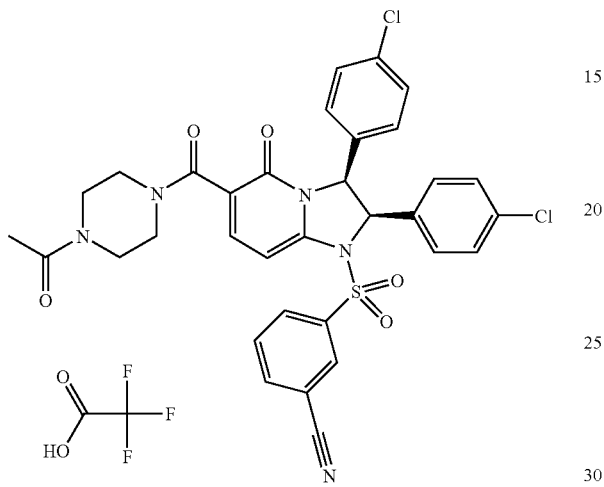

rac-3-[(6-(4-Acetyl-piperazine-1-carbonyl)-cis-2,3-bis-(4-chloro-phenyl)-5-oxo-2,3-dihydro-5H-imidazo[1,2-a]pyridine-1-sulfonyl]-benzonitrile was prepared according to general method C by reaction of rac-3-[cis-2,3-bis-(4-chloro-phenyl)-5-oxo-2,3-dihydro-6-iodo-5H-imidazo[1,2-a]pyridine-1-sulfonyl]-benzonitrile with N-acetyl-piperazine. The compound was isolated by preparative HPLC. The expected product was characterized by LC/MS (M+H) where the mass was observed as 676.1; the expected mass is 675. LC/MS indicated a purity of 100 % as measured by UV 214 nM.

Example 70

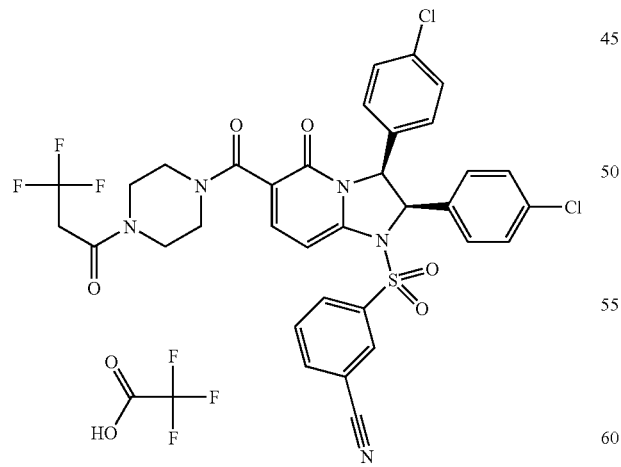

rac-3-{cis-2,3-Bis-(4-chloro-phenyl)-5-oxo-6-[4-(3,3,3-trifluoro-propionyl)-piperazine-1-carbonyl]-2,3-dihydro-5H-imidazo[1,2-a]pyridine-1-sulfonyl}-benzonitrile was prepared according to general method C by reaction of rac-3-[cis-2,3-bis-(4-chloro-phenyl)-5-oxo-2,3-dihydro-6-iodo-5H-imidazo[1,2-a]pyridine-1-sulfonyl]-benzonitrile with 3,3,3-trifluoro-1-piperazin-1-yl-propane-1-one. The compound was isolated by preparative HPLC. The expected product was characterized by LC/MS (M+H) where the mass was observed as 744.17; the expected mass is 743. LC/MS indicated a purity of 100% as measured by UV 214 nM.

Example 71 rac-cis-2,3-Bis-(4-chloro-phenyl)-1-acetyl-2,3-dihydro-6-iodo-1H-imidazo[1,2-a]pyridin-5-one Step 1 Preparation of rac-cis-2,3-Bis-(4-chloro-phenyl)-1-acetyl-2,3-dihydro-6-iodo-1H-imidazo[1,2-a]pyridin-5-one

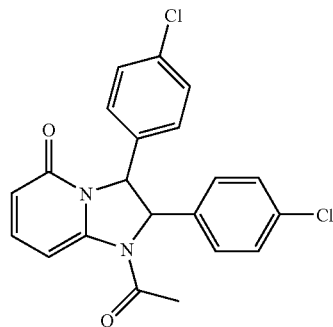

To a solution of rac-cis-2,3-bis-(4-chloro-phenyl)-2,3-dihydro-1H-imidazo[1,2-a]pyridin-5-one (3.012 g, 8.44 mmol) in DCM (100 mL) cooled in an ice bath, DIPEA (3.12 g, 4.2 mL, 25.31 mmol) and DMAP (20 mg, 0.16 mmol) were added, followed by acetyl chloride (1.325 g, 1.2 mL, 16.87 mmol). The reaction was stirred at rt for 4 hrs, MeOH (10 mL) was added to quench the reaction. The solvent was removed under reduced pressure.

FCC (10% MeOH/DCM) provided rac-cis-2,3-Bis-(4-chloro-phenyl)-1-acetyl-2,3-dihydro-1H-imidazo[1,2-a]pyridin-5-one as a solid (3.0 g, yield 89%).

$^1$H NMR (CDCl$_3$): δ 7.48 (dd, 1H), 7.12 (d, 2H), 7.09 (d, 1H), 7.04 (m, 2H), 6.79 (d, 2H), 6.63 (m, 2H), 6.24 (d, 1H), 5.95 (d, 1H), 5.68 (d, 1H), 1.96 (s, 3H).

Step 2: Preparation of rac-cis-2,3-Bis-(4-chloro-phenyl)-1-acetyl-2,3-dihydro-6-iodo-1H-imidazo[1,2-a]pyridin-5-one

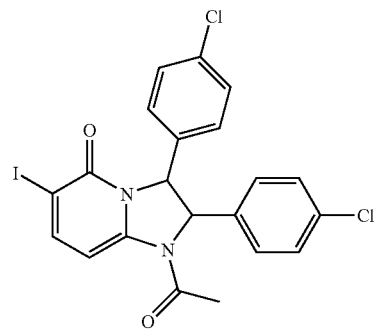

To a solution of rac-cis-2,3-Bis-(4-chloro-phenyl)-1-acetyl-2,3-dihydro-1H-imidazo[1,2-a]pyridin-5-one (3.0 g, 7.52 mmol) in MeOH (100 mL), NIS (2.0 g, 9.02 mmol) was added and stirred at rt for 3 hrs.

The solvent was removed under reduced pressure.

FCC (5% MeOH/DCM) provided a brown solid. (2.6 g, yield 66%).

$^1$H NMR (CDCl$_3$): δ 8.04 (d, 1H), 7.11 (d, 2H), 7.01 (m, 2H), 6.98 (d, 1H), 6.78 (d, 2H), 6.35 (m, 2H), 5.99 (d, 1H), 5.71 (d, 1H), 1.93 (s, 3H).

Method D: To a solution of rac-cis-2,3-bis-(4-chloro-phenyl)-1-acetyl-2,3-dihydro-6-iodo-1H-imidazo[1,2-a]pyridin-5-one (45 mg, 0.086 mmol) in DME (2 mL), boronic acid (80 mg), and Cs$_2$CO$_3$ (100 mg), PdCl$_2$(dppf) (10 mg) were added, and heated at 60° C. for one hour.

The reaction was diluted with EtOAc (6 mL), washed with water (3 mL), dried under reduced pressure.

Preparative HPLC provided the title compound.

Example 72

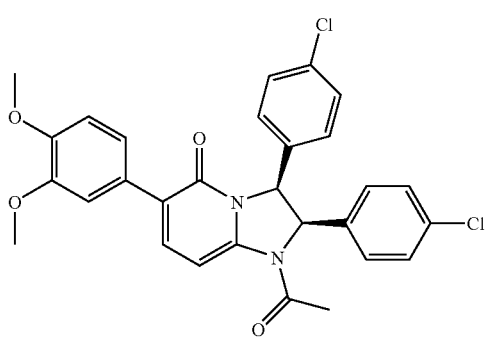

rac-cis-1-Acetyl-2,3-bis-(4-chloro-phenyl)-6-(3,4-dimethoxy-phenyl)-2,3-dihydro-1H-imidazo[1,2-a]pyridin-5-one was prepared according to general method D by reaction of rac-cis-1-acetyl-2,3-bis-(4-chloro-phenyl)-2,3-dihydro-6-iodo-1H-imidazo[1 2-a]pyridin-5-one with 3,4-dimethoxyphenylboronic acid The compound was isolated by preparative HPLC. The expected product was characterized by LC/MS (M+H) where the mass was observed as 535.16; the expected mass is 534.1. LC/MS indicated a purity of 100% as measured by UV 214 nM.

Example 73

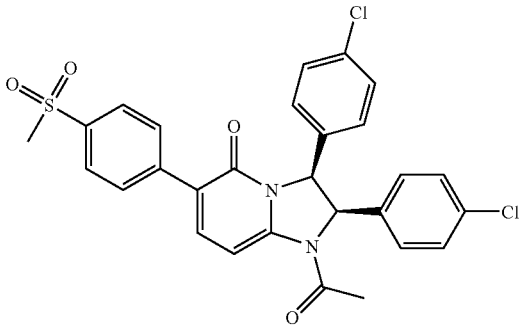

rac-cis-1-Acetyl-2,3-bis-(4-chloro-phenyl)-6-(4-methanesulfonyl-phenyl)-2,3-dihydro-1H-imidazo[1,2-a]pyridin-5-one was prepared according to general method D by reaction of rac-cis-1-acetyl-2,3-bis-(4-chloro-phenyl)-2,3-dihydro-6-iodo-1H-imidazo[1,2-a]pyridin-5-one with 4-(methylsulfonyl)phenylboronic acid. The compound was isolated by preparative HPLC. The expected product was characterized by LC/MS (M+H) where the mass was observed as 553.09; the expected mass is 552.1. LC/MS indicated a purity of 100% as measured by UV 214 nM.

Example 74

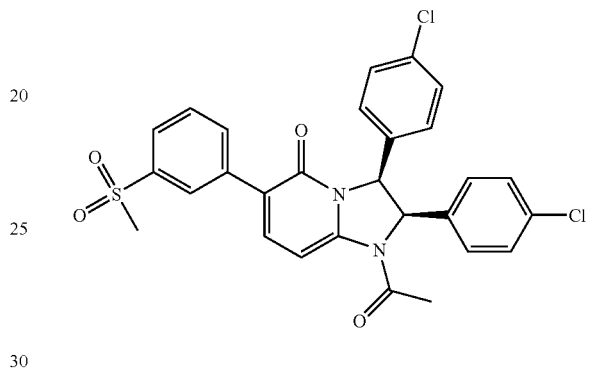

rac-cis-1-Acetyl-2,3-bis-(4-chloro-phenyl)-6-(3-methanesulfonyl-phenyl)-2,3-dihydro-1H-imidazo[1,2-a]pyridin-5-one was prepared according to general method D by reaction of rac-cis-1-acetyl-2,3-bis-(4-chloro-phenyl)-2,3-dihydro-6-iodo-1H-imidazo[1,2-a]pyridin-5-one with 3-(methylsulfonyl)phenylboronic acid The compound was isolated by preparative HPLC. The expected product was characterized by LC/MS (M+H) where the mass was observed as 553.11; the expected mass is 552.1. LC/MS indicated a purity of 100% as measured by UV 214 nM.

Example 75

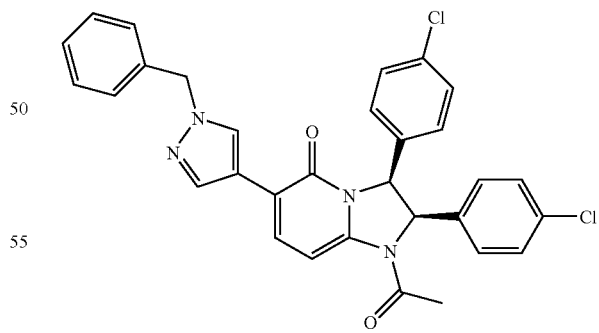

rac-cis-1-Acetyl-6-(1-benzyl-1H-pyrazol-4-yl)-2,3-bis-(4-chloro-phenyl)-2,3-dihydro-1H-imidazo[1,2-a]pyridin-5-one was prepared according to general method D by reaction of rac-cis-1-acetyl-2,3-bis-(4-chloro-phenyl)-2,3-dihydro-6-iodo-1H-imidazo[1,2-a]pyridin-5-one with 1-benzyl-1H-pyrazole-4-boronic acid. The compound was isolated by preparative HPLC. The expected product was characterized by LC/MS (M+H) where the mass was observed as 555.17; the expected mass is 554.1. LC/MS indicated a purity of 100% as measured by UV 214 nM.

Example 76

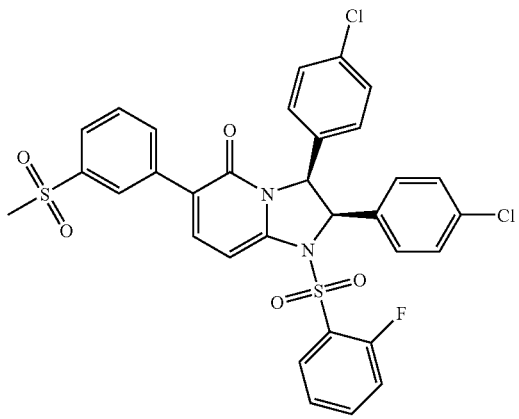

rac-cis-2,3-Bis-(4-chloro-phenyl)-1-(2-fluoro-benzene-sulfonyl)-6-(3-methanesulfonyl-phenyl)-2,3-dihydro-1H-imidazo[1,2-a]pyridin-5-one was prepared according to general method D by reaction of rac-cis-2,3-bis-(4-chloro-phenyl)-1-(2-fluoro-benzenesulfonyl)-2,3-dihydro-6-iodo-1H-imidazo[1,2-a]pyridin-5-one with 3-(methylsulfonyl)phenylboronic acid. The compound was isolated by preparative HPLC. The expected product was characterized by LC/MS (M+H) where the mass was observed as 669.0; the expected mass is 668. LC/MS indicated a purity of 100% as measured by UV 214 nM.

Example 77

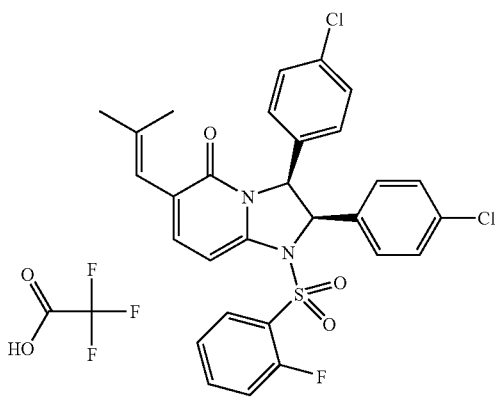

rac-cis-2,3-Bis-(4-chloro-phenyl)-1-(2-fluoro-benzene-sulfonyl)-6-(2-methyl-propenyl)-2,3-dihydro-1H-imidazo[1,2-a]pyridin-5-one was prepared according to general method D by reaction of rac-cis-2,3-bis-(4-chloro-phenyl)-1-(2-fluoro-benzenesulfonyl)-2,3-dihydro-6-iodo-1H-imidazo[1,2-a]pyridin-5-one with 2,2-dimethylethenylboronic acid. The compound was isolated by preparative HPLC. The expected product was characterized by LC/MS (M+H) where the mass was observed as 569.06; the expected mass is 568. LC/MS indicated a purity of 100% as measured by UV 214 nM.

Example 78 rac-3-[cis-2,3-Bis-(4-chloro-phenyl)-6-(2-methyl-propenyl)-5-oxo-2,3-dihydro-5H-imidazo[1,2-a]pyridine-1-sulfonyl]-benzonitrile

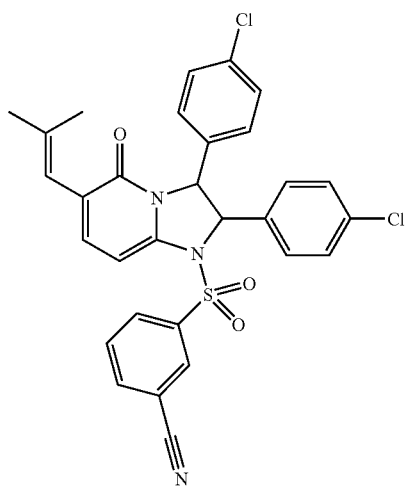

The titled compound was prepared according to general method D by reaction of rac-3-[cis-2,3-bis-(4-chloro-phenyl)-5-oxo-2,3-dihydro-6-iodo-5H-imidazo[1,2-a]pyridine-1-sulfonyl]-benzonitrile with 2,2-dimethylethenylboronic acid. The compound was isolated by FCC (2.5% MeOH/DCM). The expected product was characterized by $^1$H NMR $^1$H NMR (400 MHz, CDCl$_3$): δ 8.02-7.95 (m, 3H), 7.69 (dd, 1H), 7.42 (d, 1H), 7.10-7.03 (m, 4H), 6.84 (d, 2H), 6.75 (d, 1H), 6.52 (d, 2H), 6.08 (s, 1H), 5.71 (d, 1H), 5.24 (d, 1H) 1.86 (s, 3H), 1.83 (s, 3H).

Example 79 rac-3-[cis-2,3-Bis-(4-chloro-phenyl)-6-formyl-5-oxo-2,3-dihydro-5H-imidazo[1,2-a]pyridine-1-sulfonyl]-benzonitrile

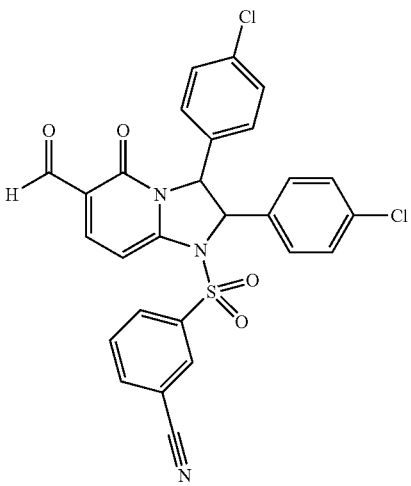

To a solution of rac-3-[cis-2,3-Bis-(4-chloro-phenyl)-6-(2-methyl-propenyl)-5-oxo-2,3-dihydro-5H-imidazo[1,2-a]pyridine-1-sulfonyl]-benzonitrile (134 mg, 0.24 mmol) in 10% methanolic DCM (20 mL) cooled at −78° C., 2 mg Sudan III was added as a dye.

A stream of $O_3$ was passed through the solution until Sudan III was faded. $N_2$ was bubbled through for 3 minutes to remove excess $O_3$. Pyridine (0.3 mL) and dimethylsulfide (1.5 mL) were added and stored at −4° C. overnight.

The solvent was removed under reduced pressure.

FCC (5% MeOH/DCM) provided an oil. (103 mg yield 81%).

$^1$H NMR (400 MHz, $CDCl_3$): δ 10.05 (s, 1H), 8.25 (d, 1H), 7.98-7.91 (m, 3H), 7.70 (dd, 1H), 7.11-7.08 (m, 4H), 6.87 (d, 1H), 6.75 (m, 2H), 6.59 (m, 2H), 5.86 (d, 1H), 5.49 (d, 1H).

Method E: To a solution of an aldehyde shown below (35 mg, 0.064 mmol) in THF (5 mL), amine (5 equiv.,) was added, followed by AcOH (10 μL) and stirred for 5 minutes. NaC-NBH$_3$ (3 equiv,) was added and stirred for 1 hour. The reaction was diluted with EtOAc (200 mL), washed with NaHCO$_3$, dried with Na$_2$SO$_4$, and filtered; the filtrated was concentrated under reduced pressure gave an oil.

Preparative HPLC provided the title compound.

Example 80

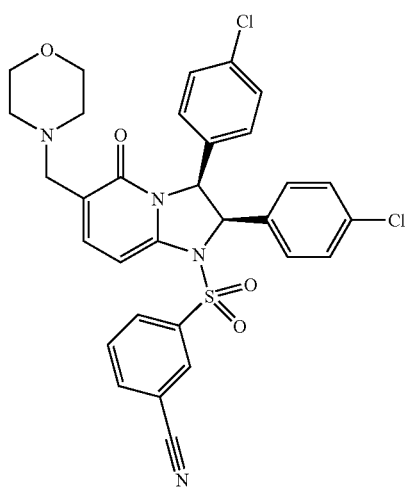

rac-3-[cis-2,3-Bis-(4-chloro-phenyl)-6-morpholin-4-ylmethyl-5-oxo-2,3-dihydro-5H-imidazo[1,2-a]pyridine-1-sulfonyl]-benzonitrile was prepared according to general method E by reaction of rac-3-[cis-2,3-bis-(4-chloro-phenyl)-6-formyl-5-oxo-2,3-dihydro-5H-imidazo[1,2-a]pyridine-1-sulfonyl]-benzonitrile with Morpholine. The compound was isolated by preparative HPLC. The expected product was characterized by LC/MS (M+H) where the mass was observed as 621.06; the expected mass is 620. LC/MS indicated a purity of 100% as measured by UV 214 nM.

Example 81

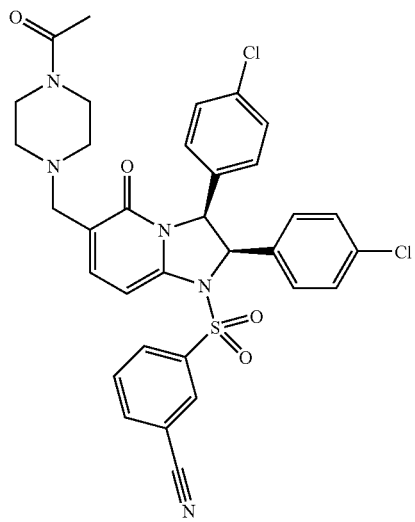

rac-3-[cis-6-(4-Acetyl-piperazin-1-ylmethyl)-2,3-bis-(4-chloro-phenyl)-5-oxo-2,3-dihydro-5H-imidazo[1,2-a]pyridine-1-sulfonyl]-benzonitrile was prepared according to general method E by reaction of rac-3-[cis-2,3-bis-(4-chloro-phenyl)-6-formyl-5-oxo-2,3-dihydro-5H-imidazo[1 2-a] pyridine-1-sulfonyl]-benzonitrile with N-acetyl-piperazine. The compound was isolated by preparative HPLC. The expected product was characterized by LC/MS (M+H) where the mass was observed as 662.12; the expected mass is 661. LC/MS indicated a purity of 100% as measured by UV 214 nM.

Example 82

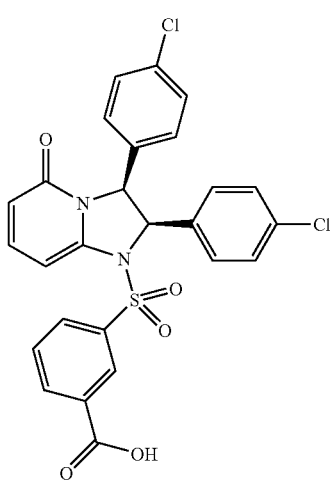

rac-3-[cis-2,3-Bis-(4-chloro-phenyl)-5-oxo-2,3-dihydro-5H-imidazo[1,2-a]pyridine-1-sulfonyl]-benzoic acid To a solution of rac-3-[cis-2,3-bis-(4-chloro-phenyl)-5-oxo-2,3-dihydro-5H-imidazo[1,2-a]pyridine-1-sulfonyl]-benzoic acid methyl ester (62 mg 0.112 mmol) in THF (5 mL), 2N NaOH solution (112 µl, 2 equiv.) was added and stirred at rt overnight.

From HPLC, starting material was consumed, 2N HCl solution (150 µl) was added to quench the reaction. The reaction was concentrated under reduced pressure to dryness.

The compound was isolated by preparative HPLC. The expected product was characterized by LC/MS (M+H) where the mass was observed as 540.96; the expected mass is 540. LC/MS indicated a purity of 100% as measured by UV 214 nM.

Method F: Separation and Isolation of Enantiomerically Pure Analogs

Supercritical fluid chromatography was used to resolve racemic mixtures into single enantiomers as described at the beginning of experimental methods section.

Example 83

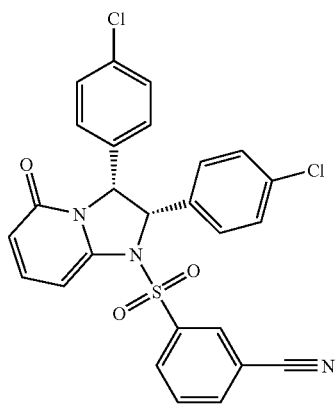

Single Enantiomer: 1$^{st}$ Eluted Enantiomer of Racemic Mixture Generated in Example 3

3-[2R*,3S*-bis-(4-chloro-phenyl)-5-oxo-2,3-dihydro-5H-imidazo[1,2-a]pyridine-1-sulfonyl]-benzonitrile was prepared first according to general method A by reaction of rac-cis-bis-(4-chloro-phenyl)-2,3-dihydro-1H-imidazo[1,2-a]pyridin-5-one with 3-cyano-benzenesulfonyl chloride. The racemic mixture was purified by preparative HPLC. The mixture was then separated into enantiomers by dissolving in DMSO and injecting 33 mg quantities on to a preparative SFC (Daicel OD 3×25 cm 35% MeOH 70 ml/mn 220 nM). The first eluted compound was collected as example 83. The expected product was characterized by LC/MS (M+H) where the mass was observed as 521.89; the expected mass is 521.

LC/MS indicated a purity of 10% as measured by UV 214 nM. [α]$_D$−183 (c 1.0, DMSO)

Example 84 and Example 85

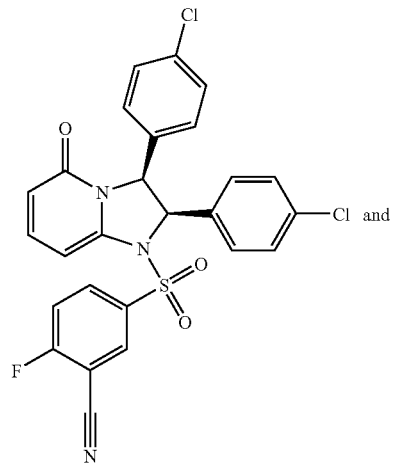

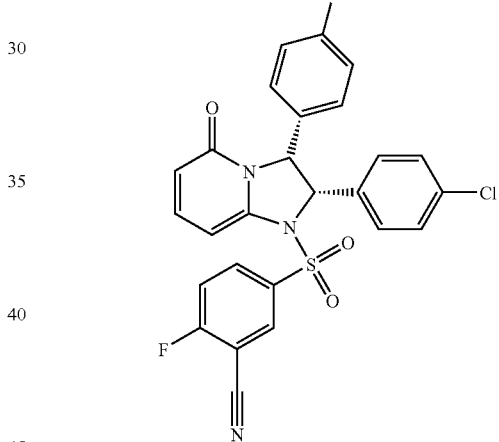

Single Enantiomers: 1$^{st}$ and 2$^{nd}$ Eluted Enantiomers of Racemic Mixture Generated in Example 2

The two entiomers of 5-[cis-2,3-bis-(4-chloro-phenyl)-5-oxo-2,3-dihydro-5H-imidazo[1,2-a]pyridine-1-sulfonyl]-2-fluoro-benzonitrile (Example 84 and 85) was prepared first according to general method A by reaction of racemic cis-2,3-bis-(4-chloro-phenyl)-2,3-dihydro-1H-imidazo[1,2-a]pyridin-5-one with 3-cyano-4-fluorobenzenesulfonyl chloride. The compound was isolated by dissolving in DMSO and injecting on to a preparative SFC (Daicel OD 3×25 cm 35% MeOH 70 ml/mn 220 nM). The second eluted compound was Example 84, 5-[(2R*,3S*)-2,3-Bis-(4-chloro-phenyl)-5-oxo-2,3-dihydro-5H-imidazo[1,2-a]pyridine-1-sulfonyl]-2-fluoro-benzonitrile. The expected product was characterized by LC/MS (M+H) where the mass was observed as 539.8; the expected mass is 539. LC/MS indicated a purity of 100% as measured by UV 214 nM. [α]$_D$+109.0 (c 1.0, DMSO). The first eluted compound was Example 85, 5-[(2R*,3S*)-2,3-

Bis-(4-chloro-phenyl)-5-oxo-2,3-dihydro-5H-imidazo[1,2-a]pyridine-1-sulfonyl]-2-fluoro-benzonitrile.

Example 86

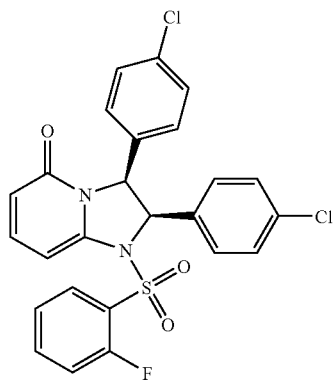

Single Enantiomer. 1st Eluted of Example 5

2R*3S*-bis-(4-chloro-phenyl)-1-(2-fluoro-benzenesulfonyl)-2,3-dihydro-1H-imidazo[1,2-a]pyridin-5-one was prepared first according to general method A by reaction of rac-cis-bis-(4-chloro-phenyl)-2,3-dihydro-1H-imidazo[1,2-a]pyridin-5-one with 2-fluorobenzenesulfonyl chloride. The racemic mixture was then purified by preparative HPLC. The mixture was then separated into enantiomers by dissolving in DMSO and injecting on to a preparative SFC (Daicel OD 3×25 cm 35% MeOH 70 ml/mn 220 nM). The first eluted product was collected as Example 86 and was characterized by LC/MS (M+H) where the mass was observed as 514.9; the expected mass is 514. LC/MS indicated a purity of 100% as measured by UV 214 nM. $[\alpha]_D$ –118.0 (c 1.0, DMSO).

Example 87

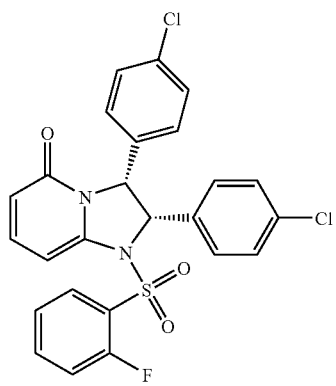

Single Enantiomer: 2nd Eluted Compound of Racemic Mixture Derived from Example 5

2R*,3S*-bis-(4-chloro-phenyl)-1-(2-fluoro-benzenesulfonyl)-2,3-dihydro-1H-imidazo[1,2-a]pyridin-5-one was prepared according to general method A by reaction of rac-cis-bis-(4-chloro-phenyl)-2,3-dihydro-1H-imidazo[1,2-a]pyridin-5-one with 2-fluorobenzenesulfonyl chloride. The racemic mixture was purified by preparative HPLC. The mixture was then separated into enantiomers by dissolving in DMSO and injecting 33 mg quantities on to a preparative SFC (Daicel OD 3×25 cm 35% MeOH 70 ml/mn 220 nM). The second eluted compound was collected as example 87.

Example 88

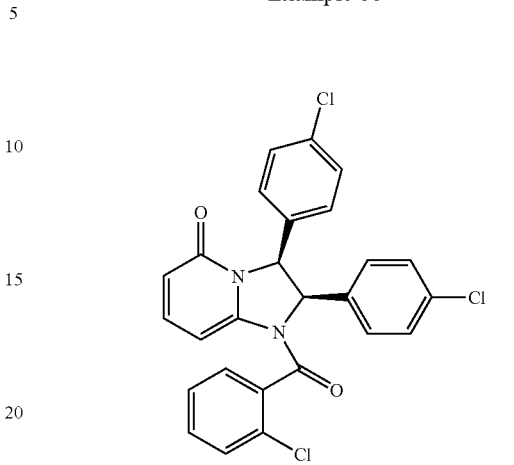

Single Enantiomer: 1st Eluted Compound of Racemic Mixture Derived from Example 8

1-(2-Chloro-benzoyl)2R*,3S*-bis-(4-chloro-phenyl)-2,3-dihydro-1H-imidazo[1,2-a]pyridin-5-one was prepared first according to general method A by reaction of rac-cis-bis-(4-chloro-phenyl)-2,3-dihydro-1H-imidazo[1,2-a]pyridin-5-one with 2-chlorobenzoyl chloride. The racemic mixture was purified by preparative HPLC. The mixture was then separated into enantiomers by dissolving in DMSO and injecting 33 mg quantities on to a preparative SFC (Daicel QD 3×25 cm 35% MeOH 70 ml/mn 220 nM). The first eluted compound was collected as example 88. $[\alpha]_D$ –80.6 (c 3.5 DMSO)

Example 89

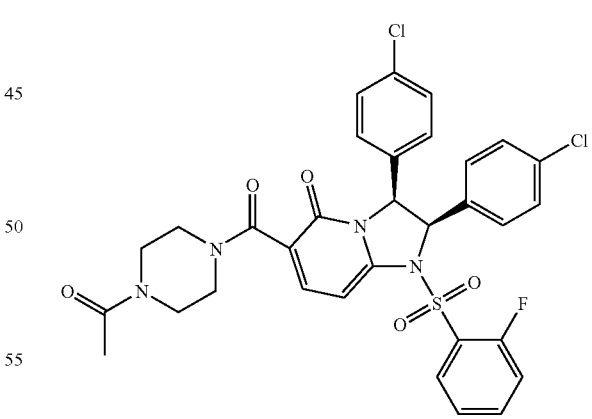

Single Enantiomer: 1st Eluted Compound of Racemic Mixture Derived from Example 50

6-(4-acetyl-piperazine-1-carbonyl)-2R*,3S*-bis-(4-chloro-phenyl)-1-(2-fluoro-benzenesulfonyl)-2,3-dihydro-1H-imidazo[1,2-a]pyridin-5-one was obtained by resolution of the enantiomeric mixture of example 45. The mixture was then separated into enantiomers by dissolving in DMSO and injecting 33 mg quantities on to a preparative SFC (Daicel OD 3×25 cm 35% MeOH 70 ml/mn 220 nM). The first eluted compound was collected as example 89.

Example 90

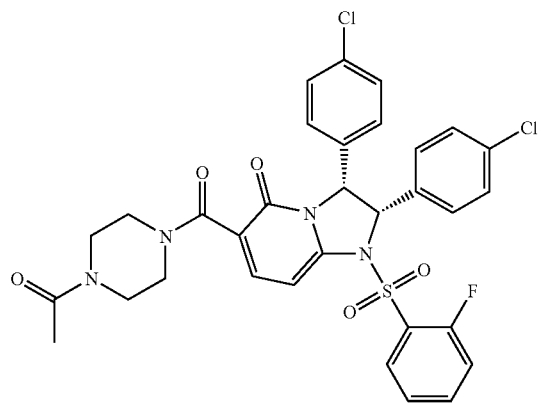

Single Enantiomer: 2$^{nd}$ Eluted Compound of Racemic Mixture Derived from Example 50

6-(4-Acetyl-piperazine-1-carbonyl)2R*,3S*-bis-(4-chloro-phenyl)-1-(2-fluoro-benzenesulfonyl)-2,3-dihydro-1H-imidazo[1,2-a]pyridin-5-one was obtained by SFC chromatography. The mixture of example 50 was separated into enantiomers by dissolving in DMSO and injecting 33 mg quantities on to a preparative SFC (Daicel OD 3×25 cm 35% MeOH 70 ml/mn 220 nM). The second eluted compound was collected as example 90.

Example 91

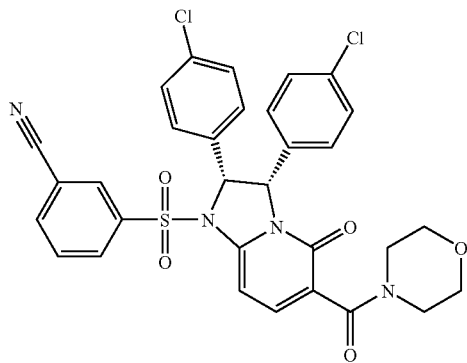

Single Enantiomer: 2$^{nd}$ Eluted Compound of Racemic Mixture Derived from Example 68

3-[2R*,3S*-bis-(4-chloro-phenyl)-6-(morpholine-4-carbonyl)-5-oxo-2,3-dihydro-5H-imidazo[1,2-a]pyridine-1-sulfonyl]-benzonitrile. The compound was isolated by dissolving the racemic mixture of example 68 in DMSO and injecting on to a preparative SFC (Daicel OD 3×25 cm 35% MeOH 70 ml/mn 220 nM). The second eluted product was collected as example 91. The expected product was characterized by LC/MS (M+H) where the mass was observed as 634.9; the expected mass is 634. LC/MS indicated a purity of 100% as measured by UV 214 nM. $[\alpha]_D$ –18.0 (c 1.0, DMSO)

Example 92

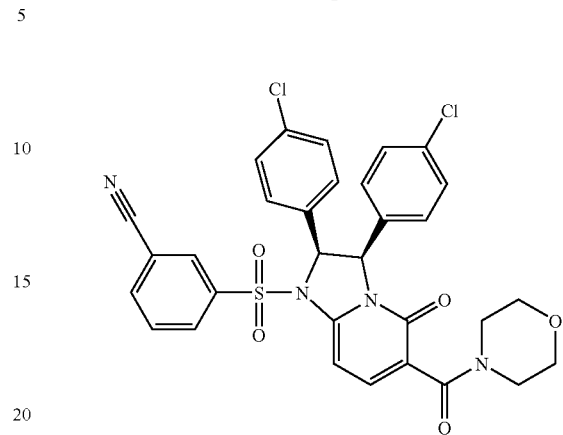

Single Enantiomer: 1$^{st}$ Eluted of Example 68

3-[2R*,3S*-bis-(4-chloro-phenyl)-6-morpholine-4-carbonyl)-5-oxo-2,3-dihydro-5H-imidazo[1,2-a]pyridine-1-sulfonyl]-benzonitrile. The compound was isolated by dissolving Example 68 in DMSO and injecting on to a preparative SFC (Daicel OD 3×25 cm 35% MeOH 70 ml/mn 220 nM). The first eluted product was collected as Example 92. The expected product was characterized by LC/MS (M+H) where the mass was observed as 634.9 the expected mass is 634. LC/MS indicated a purity of 100% as measured by UV 214 nM. No rotation was observed

Example 93

In Vitro Activity Assay

The ability of the compounds to inhibit the interaction between p53 and MDM2 proteins was measured by an HTRF (homogeneous time-resolved fluorescence) assay in which recombinant GST-tagged MDM2 binds to a peptide that resembles the MDM2-interacting region of p53 (Lane et al.). Binding of GST-MDM2 protein and p53-peptide (biotinylated on its N-terminal end) is registered by the FRET (fluorescence resonance energy transfer) between Europium (Eu)-labeled anti-GST antibody and streptavidin-conjugated Allophycocyanin (APC).

Test is performed in black flat-bottom 384-well plates (Costar) in a total volume of 40 µL containing: 90 nM biotinylated peptide, 160 ng/ml GST-MDM2, 20 nM streptavidin-APC (PerkinElmerWallac), 2 nM Eu-labeled anti-GST-antibody (PerkinElmerWallac) 0.2% bovine serum albumin (BSA), 1 mM dithiothreitol (DTT) and 20 mM Tris-borate saline (TBS) buffer as follows: Add 10 µL of GST-MDM2 (640 ng/ml working solution) in reaction buffer to each well. Add 10 µL diluted compounds (1:5 dilution in reaction buffer) to each well mix by shaking. Add 20 µL biotinylated p53 peptide (180 nM working solution) in reaction buffer to each well and mix on shaker. Incubate at 37° C. for 1 h. Add 20 µL streptavidin-APC and Eu-anti-GST antibody mixture (6 nM Eu-anti-GST and 60 nM streptavidin-APC working solution) in TBS buffer with 0.2% BSA, shake at room temperature for 30 minutes and read using a TRF-capable plate reader at 665 and 615 nm (Victor 5, Perkin ElmerWallac). If not specified, the reagents were purchased from Sigma Chemical Co.

IC$_{50}$s showing biological activity that applies to compounds of the subject matter of this invention ranges from about 0.400 µM to about 5 µM. Specific data for some examples are as follows:

| Example Number | Structure name | IC$_{50}$ Value (µM) |
|---|---|---|
| Example 62 | rac-3-{cis-2,3-Bis-(4-chloro-phenyl)-6-[4-(2-morpholin-4-yl-2-oxo-ethyl)-piperazine-1-carbonyl]-5-oxo-2,3-dihydro-5H-imidazo[1,2-a]pyridine-1-sulfonyl}-benzoic acid methyl ester | 0.47 |
| Example 63 | rac-3-[cis-2,3-Bis-(4-chloro-phenyl)-6-(4-methyl-piperazine-1-carbonyl)-5-oxo-2,3-dihydro-5H-imidazo[1,2-a]pyridine-1-sulfonyl]-benzoic acid methyl ester | 0.46 |
| Example 66 | rac-3-{cis-2,3-Bis-(4-chloro-phenyl)-6-[4-(2-imidazol-1-yl-ethyl)-piperazine-1-carbonyl]-5-oxo-2,3-dihydro-5H-imidazo[1,2-a]pyridine-1-sulfonyl}-benzoic acid methyl ester | 0.67 |
| Example 10 | rac-cis-2,3-Bis-(4-chloro-phenyl)-1-(thiophene-3-sulfonyl)-2,3-dihydro-1H-imidazo[1,2-a]pyridin-5-one | 0.71 |
| Example 51 | rac-cis-2,3-Bis-(4-chloro-phenyl)-1-(2-fluoro-benzenesulfonyl)-6-[4-(2-morpholin-4-yl-2-oxo-ethyl)-piperazine-1-carbonyl]-2,3-dihydro-1H-imidazo[1,2-a]pyridin-5-one | 0.71 |
| Example 82 | rac-3-[cis-2,3-Bis-(4-chloro-phenyl)-5-oxo-2,3-dihydro-5H-imidazo[1,2-a]pyridine-1-sulfonyl]-benzoic acid | 0.77 |
| Example 84 | 5-[(2R*,3S*)-2,3-Bis-(4-chloro-phenyl)-5-oxo-2,3-dihydro-5H-imidazo[1,2-a]pyridine-1-sulfonyl]-2-fluoro-benzonitrile(2$^{nd}$ eluted) | 0.5 |
| Example 85 | 5-[(2R*,3S*)-2,3-Bis-(4-chloro-phenyl)-5-oxo-2,3-dihydro-5H-imidazo[1,2-a]pyridine-1-sulfonyl]-2-fluoro-benzonitrile (1$^{st}$ eluted) | 0.22 |
| Example 91 | 3-[(2R*,3S*)-2,3-Bis-(4-chloro-phenyl)-6-(morpholine-4-carbonyl)-5-oxo-2,3-dihydro-5H-imidazo[1,2-a]pyridine-1-sulfonyl]-benzonitrile (2$^{nd}$ eluted) | 1.6 |
| Example 92 | 3-[(2R*,3S*)-2,3-Bis-(4-chloro-phenyl)-6-(morpholine-4-carbonyl)-5-oxo-2,3-dihydro-5H-imidazo[1,2-a]pyridine-1-sulfonyl]-benzonitrile (1$^{st}$ eluted) | 0.69 |

What is claimed:

1. A compound of the formula

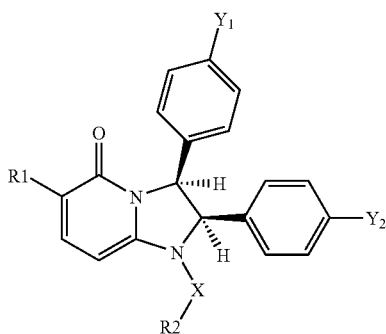

wherein $Y_1$ and $Y_2$ are independently selected from the group consisting of halogen, trifluoromethyl, —NO$_2$, —C≡N, and —C≡CH;

X is selected from the group consisting of —SO$_2$, —C=O and —C=OCH$_2$;

R1 is selected from the group consisting of hydrogen, halogen, aryl, substituted aryl, heterocycle, substituted heterocycle; alkenyl and C=OR3 wherein R3 is alkoxy, amino, cycloamino, heterocycle or substituted heterocycle;

R2 is selected from the group consisting of substituted or unsubstituted cycloalkyl, aryl, heteroaryl and heterocycle;

and the pharmaceutically acceptable salts and esters thereof.

2. The compound of claim 1 wherein $Y_1$ and $Y_2$ are —Cl or —Br and X is SO$_2$.

3. The compound of claim 2 wherein $R_2$ is aryl which is disubstituted by halogen and CN.

4. The compound of claim 2 wherein $R_2$ is aryl which is monosubstituted by carboxy alkoxy.

5. The compound of claim 3 wherein $R_1$ is hydrogen or —COR$_3$ where R$_3$ is a substituted or unsubstituted heterocycle.

6. The compound of claim 4 wherein $R_1$ is hydrogen or —COR$_3$ where R$_3$ is a substituted or unsubstituted heterocycle.

7. The compound of claim 3 wherein the two hydrogen atoms of the imidazoline ring are in a cis configuration to each other.

8. The compound of claim 4 wherein the two hydrogen atoms of the imidazoline ring are in a cis configuration to each other.

9. A compound of claim 1 selected from the group consisting of

5-[rac-cis-2,3-Bis-(4-chloro-phenyl)-5-oxo-2,3-dihydro-5H-imidazo[1,2-a]pyridine-1-sulfonyl]-2-fluoro-benzonitrile;

3-2R*,3S*-Bis-(4-chloro-phenyl)-5-oxo-2,3-dihydro-5H-imidazo[1,2-a]pyridine-1-sulfonyl]-benzonitrile;

5-[2R*,3S*-Bis-(4-chloro-phenyl)-5-oxo-2,3-dihydro-5H-imidazo[1,2-a]pyridine-1-sulfonyl]-2-fluoro-benzonitrile;

2R*,3S*-Bis-(4-chloro-phenyl)-1-(2-fluoro-benzenesulfonyl)-2,3-dihydro-1H-imidazo[1,2-a]pyridin-5-one;

rac-3-[cis-2,3-Bis-(4-chloro-phenyl)-5-oxo-2,3-dihydro-5H-imidazo[1,2-a]pyridine-1-sulfonyl]-benzonitrile;

rac4-[-cis-2,3-Bis-(4-chloro-phenyl)-5-oxo-2,3-dihydro-5H-imidazo[1,2-a]pyridine-1-sulfonyl]-benzonitrile;

rac-cis-2,3-Bis-(4-chloro-phenyl)-1-(2-fluoro-benzene-sulfonyl)-2,3-dihydro-1H-imidazo[1,2-a]pyridin-5-one;

rac-cis-2,3-Bis-(4-chloro-phenyl)-1-(2,4-difluoro-benzenesulfonyl)-2,3-dihydro-1H-imidazo[1,2-a]pyridin-5-one;

rac-cis-2,3-Bis-(4-chloro-phenyl)-1-(2,5-dimethoxy-benzenesulfonyl)-2,3-dihydro-1H-imidazo[1,2-a]pyridin-5-one and rac-cis-1-(2-Chloro-benzoyl)-2,3-bis-(4-chloro-phenyl)-2,3-dihydro-1H-imidazo[1,2-a]pyridin-5-one.

10. A compound of claim 1 selected from the group consisting of rac-cis-1-(2-Chloro-benzenesulfonyl)-2,3-bis-(4-chloro-phenyl)-2,3-dihydro-1H-imidazo[1,2-a]pyridin-5-one;

rac-cis-2,3-Bis-(4-chloro-phenyl)-1-(thiophene-3-sulfonyl)-2,3-dihydro-1H-imidazo[1,2-a]pyridin-5-one;

rac-cis-2,3-Bis-(4-chloro-phenyl)-1-(1-methyl-1H-imidazole-4-sulfonyl)-2,3-dihydro-1H-imidazo[1,2-a]pyridin-5-one;

rac-cis-2,3-Bis-(4-chloro-phenyl)-1-(4-fluoro-benzene-sulfonyl)-2,3-dihydro-1H-imidazo[1,2-a]pyridin-5-one;

rac-cis-1-Benzenesulfonyl-rac-cis-bis-(4-chloro-phenyl)-2,3-dihydro-1H-imidazo[1,2-a]pyridin-5-one;

rac-cis-2,3-Bis-(4-chloro-phenyl)-1-(2,6-difluoro-benzenesulfonyl)-2,3-dihydro-1H-imidazo[1,2-a]pyridin-5-one;

rac-cis-2,3-Bis-(4-chloro-phenyl)-1-(thiophene-2-sulfonyl)-2,3-dihydro-1H-imidazo[1,2-a]pyridin-5-one;

rac-cis-1-(3-Chloro-2-fluoro-benzenesulfonyl)-2,3-bis-(4-chloro-phenyl)-2,3-dihydro-1H-imidazo[1,2-a]pyridin-5-one;

rac-cis-2,3-Bis-(4-chloro-phenyl)-1-(2-fluoro-5-methyl-benzenesulfonyl)-2,3-dihydro-1H-imidazo[1,2-a]pyridin-5-one and rac-1-(2-Chloro-4-fluoro-benzenesulfonyl)-cis-2,3-bis-(4-chloro-phenyl)-2,3-dihydro-1H-imidazo[1,2-a]pyridin-5-one.

11. A compound of claim 1 selected from the group consisting of rac-cis-2,3-Bis-(4-chloro-phenyl)-1-(4-methoxy-benzenesulfonyl)-2,3-dihydro-1H-imidazo[1,2-a]pyridin-5-one;

rac-cis-2,3-Bis-(4-chloro-phenyl)-1-(toluene-3-sulfonyl)-2,3-dihydro-1H-imidazo[1,2-a]pyridin-5-one;

rac-cis-2,3-Bis-(4-chloro-phenyl)-1-(3-methoxy-benzenesulfonyl)-2,3-dihydro-1H-imidazo[1,2-a]pyridin-5-one;

rac-cis-1-(5-Chloro-2-fluoro-benzenesulfonyl)-2,3-bis-(4-chloro-phenyl)-2,3-dihydro-1H-imidazo[1,2-a]pyridin-5-one;

rac-cis-1-(4-Chloro-2-fluoro-benzenesulfonyl)-2,3-bis-(4-chloro-phenyl)-2,3-dihydro-1H-imidazo[1,2-a]pyridin-5-one;

rac-cis-2,3-Bis-(4-chloro-phenyl)-1-(3,4-difluoro-benzenesulfonyl)-2,3-dihydro-1H-imidazo[1,2-a]pyridin-5-one;

rac-3-[cis-2,3-Bis-(4-chloro-phenyl)-5-oxo-2,3-dihydro-5H-imidazo[1,2-a]pyridine-1-sulfonyl]-benzoic acid methyl ester;

rac-cis-1-(5-Chloro-2-methoxy-benzenesulfonyl)-2,3-bis-(4-chloro-phenyl)-2,3-dihydro-1H-imidazo1,2-a]pyridin-5-one;

rac-cis-1-(3-Chloro-benzenesulfonyl)-2,3-bis-(4-chloro-phenyl)-2,3-dihydro-1H-imidazo[1,2-a]pyridin-5-one and rac-cis-2,3-Bis-(4-chloro-phenyl)-1-(3-fluoro-benzene-sulfonyl)-2,3-dihydro-1H-imidazo[1,2-a]pyridin-5-one.

12. A compound of claim 1 selected from the group consisting of rac-cis-2,3-Bis-(4-chloro-phenyl)-1-(toluene-2-sulfonyl)-2,3-dihydro-1H-imidazo[1,2-a]pyridin-5-one;

rac-cis-1-(4-Chloro-benzenesulfonyl)-2,3-bis-(4-chloro-phenyl)-2,3-dihydro-1H-imidazo[1,2-a]pyridin-5-one;

rac-cis-2,3-Bis-(4-chloro-phenyl)-1-(2-fluoro-benzoyl)-2,3-dihydro-1H-imidazo[1,2-a]pyridin-5-one;

rac-cis-1-(3-Chloro-4-fluoro-benzenesulfonyl)-2,3-bis-(4-chloro-phenyl)-2,3-dihydro-1H-imidazo[1,2-a]pyridin-5-one;

rac-cis-2,3-Bis-(4-chloro-phenyl)-1-(4-fluoro-2-methyl-benzenesulfonyl)-2,3-dihydro-1H-imidazo[1,2-a]pyridin-5-one;

rac-cis-2,3-Bis-(4-chloro-phenyl)-1-(5-fluoro-2-methyl-benzenesulfonyl)-2,3-dihydro-1H-imidazo[1,2-a]pyridin-5-one;

rac-cis-2,3-Bis-(4-chloro-phenyl)-1-(3-methoxy-benzoyl)-2,3-dihydro-1H-imidazo[1,2-a]pyridin-5-one;

rac-cis-2,3-Bis-(4-chloro-phenyl)-1-(2-trifluoromethoxy-benzenesulfonyl)-2,3-dihydro-1H-imidazo[1,2-a]pyridin-5-one;

rac-cis-2,3-Bis-(4-chloro-phenyl)-1-isobutyryl-2,3-dihydro-1H-imidazo[1,2-a]pyridin-5-one and 2R*,3S*-Bis-(4-chloro-phenyl)-1-(2-fluoro-benzene-sulfonyl)-2,3-dihydro-1H-imidazo[1,2-a]pyridin-5-one.

13. A compound of claim 1 selected from the group consisting of rac-cis-2,3-Bis-(4-chloro-phenyl)-1-cyclopropanesulfo-nyl-2,3-dihydro-1H-imidazo[1,2-a]pyridin-5-one;

rac-cis-1-(3-Chloro-benzoyl)-2,3-bis-(4-chloro-phenyl)-2,3-dihydro-1H-imidazo[1,2-a]pyridin-5-one;

rac-cis-2,3-Bis-(4-chloro-phenyl)-1-(3-trifluoromethoxy-benzenesulfonyl)-2,3-dihydro-1H-imidazo[1,2-a]pyridin-5-one;

rac-cis-2,3-Bis-(4-chloro-phenyl)-1-(3-fluoro-benzoyl)-2,3-dihydro-1H-imidazo[1,2-a]pyridin-5-one;

rac-cis-2,3-Bis-(4-chloro-phenyl)-1-[2-(2,5-dimethoxy-phenyl)-acetyl]-2,3-dihydro-1H-imidazo[1,2-a]pyridin-5-one;

rac-cis-2,3-Bis-(4-chloro-phenyl)-1-(furan-2-carbonyl)-2,3-dihydro-1H-imidazo[1,2-a]pyridin-5-one;

rac-cis-2,3-Bis-(4-chloro-phenyl)-1-(2-methoxy-benzoyl)-2,3-dihydro-1H-imidazo[1,2-a]pyridin-5-one;

1-(2-Chloro-benzoyl)2R*,3S*-bis-(4-chloro-phenyl)-2,3-dihydro-1H-imidazo[1,2-a]pyridin-5-one;

rac-cis-2,3-Bis-(4-chloro-phenyl)-1-cyclopentanecarbo-nyl-2,3-dihydro-1H-imidazo[1,2-a]pyridin-5-one and rac-cis-1-(3-Chloro-2-methyl-benzenesulfonyl)-2,3-bis-(4-chloro-phenyl)-2,3-dihydro-1H-imidazo[1,2-a]pyridin-5-one.

14. A compound of claim 1 selected from the group consisting of rac-cis-2,3-Bis-(4-chloro-phenyl)-1-(2-fluoro-benzene-sulfonyl)-2,3-dihydro-6-iodo-1H-imidazo[1,2-a]pyridin-5-one;

rac-cis-6-(4-Acetyl-piperazine-1-carbonyl)-2,3-bis-(4-chloro-phenyl)-1-(2-fluoro-benzenesulfonyl)-2,3-dihydro-1H-imidazo[1,2-a]pyridin-5-one;

-6-(4-Acetyl-piperazine-1-carbonyl)-2R*,3S*-bis-(4-chloro-phenyl)-1-(2-fluoro-benzenesulfonyl)-2,3-dihydro-1H-imidazo[1,2-a]pyridin-5-one;

rac-cis-2,3-Bis-(4-chloro-phenyl)-1-(2-fluoro-benzenesulfonyl)-6-[4-(2-morpholin-4-yl-2-oxo-ethyl)-piperazine-1-carbonyl]-2,3-dihydro-1H-imidazo[1,2-a]pyridin-5-one;

rac-cis-2,3-Bis-(4-chloro-phenyl)-1-(2-fluoro-benzenesulfonyl)-6-(morpholine-4-carbonyl)-2,3-dihydro-1H-imidazo[1,2-a]pyridin-5-one;

N-(2-{4-[rac-cis-2,3-Bis-(4-chloro-phenyl)-1-(2-fluoro-benzenesulfonyl)-5-oxo-1,2,3,5-tetrahydro-imidazo[1,2-a]pyridine-6-carbonyl]-piperazin-1-yl}-ethyl)-methanesulfonamide;

rac-cis-2,3-Bis-(4-chloro-phenyl)-1-(2-fluoro-benzenesulfonyl)-6-[4-(2-morpholin-4-yl-ethyl)-piperazine-1-carbonyl]-2,3-dihydro-1H-imidazo[1,2-a]pyridin-5-one;

rac-cis-2,3-Bis-(4-chloro-phenyl)-1-(2-fluoro-benzenesulfonyl)-6-[4-(3-methanesulfonyl-propyl)-piperazine-1-carbonyl]-2,3-dihydro-1H-imidazo[1,2-a]pyridin-5-one;

rac-cis-2,3-Bis-(4-chloro-phenyl)-1-(2-fluoro-benzenesulfonyl)-6-(4-methyl-piperazine-1-carbonyl)-2,3-dihydro-1H-imidazo[1,2-a]pyridin-5-one and rac-cis-2,3-Bis-(4-chloro-phenyl)-6-(4-ethanesulfonyl-piperazine-1-carbonyl)-1-(2-fluoro-benzenesulfonyl)-2,3-dihydro-1H-imidazo[1,2-a]pyridin-5-one.

15. A compound of claim 1 selected from the group consisting of

1-[rac-cis-2,3-Bis-(4-chloro-phenyl)-1-(2-fluoro-benzenesulfonyl)-5-oxo-1,2,3,5-tetrahydro-imidazo[1,2-a]pyridin-6-yl]-2-[4-(3-methanesulfonyl-propyl)-piperazin-1-yl]-ethane-1,2-dione;

rac-cis-2,3-Bis-(4-chloro-phenyl)-1-(2-fluoro-benzenesulfonyl)-5-oxo-1,2,3,5-tetrahydro-imidazo[1,2-a]pyridine-6-carboxylic acid methyl ester;

rac-cis-2,3-Bis-(4-chloro-phenyl)-1-(2-fluoro-benzenesulfonyl)-5-oxo-1,2,3,5-tetrahydro-imidazo[1,2-a]pyridine-6-carboxylic acid methylamide;

6-(4-Acetyl-piperazine-1-carbonyl)2R*,3S*-bis-(4-chloro-phenyl)-1-(2-fluoro-benzenesulfonyl)-2,3-dihydro-1H-imidazo[1,2-a]pyridin-5-one;

rac-3-[cis-2,3-Bis-(4-chloro-phenyl)-6-(morpholine-4-carbonyl)-5-oxo-2,3-dihydro-5H-imidazo[1,2-a]pyridine-1-sulfonyl]-benzoic acid methyl ester;

rac-3-{cis-2,3-Bis-(4-chloro-phenyl)-6-[4-(2-morpholin-4-yl-2-oxo-ethyl)-piperazine-1-carbonyl]-5-oxo-2,3-dihydro-5H-imidazo[1,2-a]pyridine-1-sulfonyl}-benzoic acid methyl ester;

rac-3-[cis-2,3-Bis-(4-chloro-phenyl)-6-(4-methyl-piperazine-1-carbonyl)-5-oxo-2,3-dihydro-5H-imidazo[1,2-a]pyridine-1-sulfonyl]-benzoic acid methyl ester;

rac-3-[cis-6-(4-Acetyl-piperazine-1-carbonyl)-2,3-bis-(4-chloro-phenyl)-5-oxo-2,3-dihydro-5H-imidazo[1,2-a]pyridine-1-sulfonyl]-benzoic acid methyl ester;

rac-3-[cis-2,3-Bis-(4-chloro-phenyl)-6-(4-ethanesulfonyl-piperazine-1-carbonyl)-5-oxo-2,3-dihydro-5H-imidazo[1,2-a]pyridine-1-sulfonyl]-benzoic acid methyl ester and rac-3-{cis-2,3-Bis-(4-chloro-phenyl)-6-[4-(2-imidazol-1-yl-ethyl)-piperazine-1-carbonyl]-5-oxo-2,3-dihydro-5H-imidazo[1,2-a]pyridine-1-sulfonyl}-benzoic acid methyl ester.

16. A compound of claim 1 selected from the group consisting of

3-{(2R,3S)-2,3-Bis-(4-chloro-phenyl)-6-[4-(2-morpholin-4-yl-2-oxo-ethyl)-piperazin-1-ylmethyl]-5-oxo-2,3-dihydro-5H-imidazo[1,2-a]pyridine-1-sulfonyl}-benzonitrile;

rac-3-[cis-2,3-Bis-(4-chloro-phenyl)-6-(morpholine-4-carbonyl)-5-oxo-2,3-dihydro-5H-imidazo[1,2-a]pyridine-1-sulfonyl]-benzonitrile;

rac-3-[(6-(4-Acetyl-piperazine-1-carbonyl)-cis-2,3-bis-(4-chloro-phenyl)-5-oxo-2,3-dihydro-5H-imidazo[1,2-a]pyridine-1-sulfonyl]-benzonitrile;

rac-3-{cis-2,3-Bis-(4-chloro-phenyl)-5-oxo-6-[4-(3,3,3-trifluoro-propionyl)-piperazine-1-carbonyl]-2,3-dihydro-5H-imidazol[1,2-a]pyridine-1-sulfonyl}-benzonitrile;

3-[2R*,3S*-Bis-(4-chloro-phenyl)-6-(morpholine-4-carbonyl)-5-oxo-2,3-dihydro-5H-imidazo[1,2-a]pyridine-1-sulfonyl]-benzonitrile;

3-[2R*,3S*-Bis-(4-chloro-phenyl)-6-(morpholine-4-carbonyl)-5-oxo-2,3-dihydro-5H-imidazo[1,2-a]pyridine-1-sulfonyl]-benzonitrile;

rac-cis-1-Acetyl-2,3-bis-(4-chloro-phenyl)-6-(3,4-dimethoxy-phenyl)-2,3-dihydro-1H-imidazo[1,2-a]pyridin-5-one;

rac-cis-1-Acetyl-2,3-bis-(4-chloro-phenyl)-6-(4-methanesulfonyl-phenyl)-2,3-dihydro-1H-imidazo[1,2-a]pyridin-5-one;

rac-cis-1-Acetyl-2,3-bis-(4-chloro-phenyl)-6-(3-methanesulfonyl-phenyl)-2,3-dihydro-1H-imidazo[1,2-a]pyridin-5-one;

rac-cis-1-Acetyl-6-(1-benzyl-1H-pyrazol-4-yl)-2,3-bis-(4-chloro-phenyl)-2,3-dihydro-1H-imidazo[1,2-a]pyridin-5-one;

rac-cis-2,3-Bis-(4-chloro-phenyl)-1-(2-fluoro-benzenesulfonyl)-6-(3-methanesulfonyl-phenyl)-2,3-dihydro-1H-imidazo[1,2-a]pyridin-5-one;

rac-cis-2,3-Bis-(4-chloro-phenyl)-1-(2-fluoro-benzenesulfonyl)-6-(2-methyl-propenyl)-2,3-dihydro-1H-imidazo[1,2-a]pyridin-5-one;

rac-3-[cis-2,3-Bis-(4-chloro-phenyl)-6-morpholin-4-ylmethyl-5-oxo-2,3-dihydro-5H-imidazo[1,2-a]pyridine-1-sulfonyl]-benzonitrile;

rac-3-[cis-6-(4-Acetyl-piperazin-1-ylmethyl)-2,3-bis-(4-chloro-phenyl)-5-oxo-2,3-dihydro-5H-imidazo[1,2-a]pyridine-1-sulfonyl]-benzonitrile and rac-3-[cis-2,3-Bis-(4-chloro-phenyl)-5-oxo-2,3-dihydro-5H-imidazo[1,2-a]pyridine-1-sulfonyl]-benzoic acid.

17. A pharmaceutical formulation comprising a compound of the formula

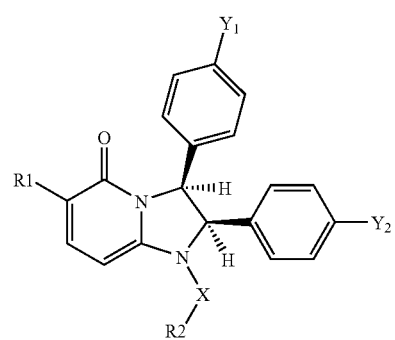

wherein $Y_1$ and $Y_2$ are independently selected from the group consisting of halogen, trifluoromethyl, —$NO_2$, —C≡N, and —C≡CH;

X is selected from the group consisting of —$SO_2$, —C═O and —C═$OCH_2$;

R1 is selected from the group consisting of hydrogen, halogen, aryl, substituted aryl, heterocycle, substituted heterocycle; alkenyl and C=OR3 wherein R3 is alkoxy, amino, cycloamino, heterocycle or substituted heterocycle;

R2 is selected from the group consisting of substituted or unsubstituted cycloalkyl, aryl, heteroaryl and heterocycle;

and the pharmaceutically acceptable salts and esters thereof together with a pharmaceutically acceptable carrier or excipient.

\* \* \* \* \*